(12) United States Patent
Blanchard et al.

(10) Patent No.: US 12,285,440 B2
(45) Date of Patent: Apr. 29, 2025

(54) APOE4 IMPAIRS MYELINATION VIA ALTERED CHOLESTEROL BIOSYNTHESIS AND TRANSPORT IN OLIGODENDROGLIA

(71) Applicant: Massachusetts Institute of Technology, Cambridge, MA (US)

(72) Inventors: Joel Blanchard, Arlington, MA (US); Manolis Kellis, Boston, MA (US); Li-Huei Tsai, Cambridge, MA (US); Jose Davila Velderrain, Saltillo (MX); Leyla Akay, Cambridge, MA (US); Djuna Von Maydell, Somerville, MA (US); Audrey Effenberger, Cambridge, MA (US); Matheus Victor, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/694,630

(22) Filed: Mar. 14, 2022

(65) Prior Publication Data
US 2022/0288104 A1  Sep. 15, 2022

Related U.S. Application Data

(60) Provisional application No. 63/160,877, filed on Mar. 14, 2021.

(51) Int. Cl.
*A61K 31/724* (2006.01)
*A61P 25/28* (2006.01)

(52) U.S. Cl.
CPC ............ *A61K 31/724* (2013.01); *A61P 25/28* (2018.01)

(58) Field of Classification Search
None
See application file for complete search history.

(56) References Cited

U.S. PATENT DOCUMENTS

| | | |
|---|---|---|
| 2005/0031651 A1 | 2/2005 | Gervais et al. |
| 2005/0059634 A1 | 3/2005 | Venton et al. |
| 2020/0000480 A1* | 1/2020 | Alambeigi ......... A61B 17/1642 |
| 2020/0000840 A1* | 1/2020 | Wittkowski ............ A61P 25/28 |
| 2020/0268788 A1 | 8/2020 | Wittkowski |
| 2020/0276225 A1* | 9/2020 | Wittkowski ........... A61K 45/06 |

FOREIGN PATENT DOCUMENTS

| | | |
|---|---|---|
| CN | 112220936 A | 1/2021 |
| WO | WO 2020/092107 A1 | 5/2020 |
| WO | WO 2020/146632 A1 | 7/2020 |

OTHER PUBLICATIONS

Cho et al., Distribution and clinical impact of apolipoprotein E4 in subjective memory impairment and early mild cognitive impairment. Sci Rep. Aug. 7, 2020;10(1):13365. doi: 10.1038/s41598-020-69603-w. PMID: 32770103; PMCID: PMC7414226.

Sienski et al., APOE4 disrupts intracellular lipid homeostasis in human iPSC-derived glia. Sci Transl Med. Mar. 3, 2021;13(583):eaaz4564. doi: 10.1126/scitranslmed.aaz4564. PMID: 33658354; PMCID: PMC8218593.

International Search Report and Written Opinion mailed Jun. 22, 2022, for Application No. PCT/US2022/020271.

Chomiak et al., What is the optimal value of the g-ratio for myelinated fibers in the rat CNS? A theoretical approach. PLoS One. Nov. 13, 2009;4(11):e7754.

Chu et al., Use of statins and the risk of dementia and mild cognitive impairment: A systematic review and meta-analysis. Sci Rep. Apr. 11, 2018;8(1):5804. doi: 10.1038/s41598-018-24248-8.

Feringa et al., Cholesterol and Alzheimer's Disease; From Risk Genes to Pathological Effects. Front Aging Neurosci. Jun. 24, 2021;13:690372. doi: 10.3389/fnagi.2021.690372.

He et al., NEBULA is a fast negative binomial mixed model for differential or co-expression analysis of large-scale multi-subject single-cell data. Commun Biol. May 26, 2021;4(1):629. doi: 10.1038/s42003-021-02146-6.

Huang et al., ApoE2, ApoE3, and ApoE4 Differentially Stimulate APP Transcription and Aβ Secretion. Cell. Jan. 26, 2017;168(3):427-441.e21. doi: 10.1016/j.cell.2016.12.044. Epub Jan. 19, 2017.

Jeong et al., ApoE4-Induced Cholesterol Dysregulation and Its Brain Cell Type-Specific Implications in the Pathogenesis of Alzheimer's Disease. Mol Cells. Nov. 30, 2019;42(11):739-746. doi: 10.14348/molcells.2019.0200.

Kamphorst et al., Liquid chromatography-high resolution mass spectrometry analysis of fatty acid metabolism. Anal Chem. Dec. 1, 2011;83(23):9114-22. doi: 10.1021/ac202220b. Epub Nov. 4, 2011.

Kunkle et al., Genetic meta-analysis of diagnosed Alzheimer's disease identifies new risk loci and implicates AB, tau, immunity and lipid processing. Nat Genet. Mar. 2019;51(3):414-430. doi: 10.1038/s41588-019-0358-2. Epub Feb. 28, 2019. Erratum in: Nat Genet. Sep. 2019;51(9):1423- 1424.

Lambert et al., Meta-analysis of 74,046 individuals identifies 11 new susceptibility loci for Alzheimer's disease. Nat Genet. Dec. 2013;45(12):1452-8. doi: 10.1038/ng.2802. Epub Oct. 27, 2013.

Law et al., An Updated Review of Lysophosphatidylcholine Metabolism in Human Diseases. Int J Mol Sci. Mar. 6, 2019;20(5):1149. doi: 10.3390/ijms20051149.

(Continued)

*Primary Examiner* — Traviss C McIntosh, III
(74) *Attorney, Agent, or Firm* — Wolf, Greenfield & Sacks, P.C.

(57) ABSTRACT

The present disclosure provides methods of inhibiting amyloid synthesis in a subject using cyclodextrin and analogs thereof. Small molecules (cyclodextrin) reverse APOE4-associated cholesterol phenotypes and lead to significantly improved myelination both human in vitro cultures and APOE4 targeted replacement mice. This demonstrates that APOE4 alters cholesterol synthesis and transport in oligodendrocytes which impairs myelination. Collectively, this work uncovers a pathogenic role of APOE4 in oligodendrocytes and myelination and enables therapeutic opportunities for Alzheimer's Disease.

15 Claims, 43 Drawing Sheets

(56) References Cited

OTHER PUBLICATIONS

Liu et al., Cholesterol involvement in the pathogenesis of neurodegenerative diseases. Mol Cell Neurosci. Jan. 2010;43(1):33-42. doi: 10.1016/j.mcn.2009.07.013. Epub Aug. 4, 2009.

Lund et al., cDNA cloning of cholesterol 24-hydroxylase, a mediator of cholesterol homeostasis in the brain. Proc Natl Acad Sci U S A. Jun. 22, 1999;96(13):7238-43. doi: 10.1073/pnas.96.13.7238.

Mathys et al., Single-cell transcriptomic analysis of Alzheimer's disease. Nature. Jun. 2019;570(7761):332-337. doi: 10.1038/s41586-019-1195-2. Epub May 1, 2019. Erratum in: Nature. Jun. 17, 2019.

Moll et al., Disrupted glycosylation of lipids and proteins is a cause of neurodegeneration. Brain. May 1, 2020;143(5):1332-1340. doi: 10.1093/brain/awz358.

Olzmann et al., Dynamics and functions of lipid droplets. Nat Rev Mol Cell Biol. Mar. 2019;20(3):137-155. doi: 10.1038/s41580-018-0085-z.

Ottinger et al., Collaborative development of 2-hydroxypropyl-β-cyclodextrin for the treatment of Niemann-Pick type C1 disease. Curr Top Med Chem. 2014;14(3):330-9. doi: 10.2174/1568026613666131127160118. Author Manuscript. 20 pages.

Qi et al., ApoE4 Impairs Neuron-Astrocyte Coupling of Fatty Acid Metabolism. Cell Rep. Jan. 5, 2021;34(1):108572 and Supplemental Information. doi: 10.1016/j.celrep.2020.108572. 32 pages.

Rauch et al., LRP1 is a master regulator of tau uptake and spread. Nature. Apr. 2020;580(7803):381-385. doi: 10.1038/s41586-020-2156-5. Epub Apr. 1, 2020.

Schultz et al., The role of statins in both cognitive impairment and protection against dementia: a tale of two mechanisms. Transl Neurodegener. Feb. 27, 2018;7:5. doi: 10.1186/s40035-018-0110-3.

Shi et al., ApoE4 markedly exacerbates tau-mediated neurodegeneration in a mouse model of tauopathy. Nature. Sep. 28, 2017;549(7673):523-527. doi: 10.1038/nature24016. Epub Sep. 20, 2017.

Strittmatter et al., Apolipoprotein E: high-avidity binding to beta-amyloid and increased frequency of type 4 allele in late-onset familial Alzheimer disease. Proc Natl Acad Sci U S A. Mar. 1, 1993;90(5):1977-81. doi: 10.1073/pnas.90.5.1977.

Tachibana et al., APOE4-mediated amyloid-β pathology depends on its neuronal receptor LRP1. J Clin Invest. Mar. 1, 2019;129(3):1272-1277. doi: 10.1172/JCI124853. Epub Feb. 11, 2019.

Traag et al., From Louvain to Leiden: guaranteeing well-connected communities. Sci Rep. Mar. 26, 2019;9(1):5233. doi: 10.1038/s41598-019-41695-z.

Van Der Kant et al., Cholesterol Metabolism Is a Druggable Axis that Independently Regulates Tau and Amyloid-β in iPSC-Derived Alzheimer's Disease Neurons. Cell Stem Cell. Mar. 7, 2019;24(3):363-375.e9 and Supplemental Information. doi: 10.1016/j.stem.2018.12.013. Epub Jan. 24, 2019. 39 pages.

Xin et al., Myelin plasticity: sculpting circuits in learning and memory. Nat Rev Neurosci. Dec. 2020;21(12):682-694. doi: 10.1038/s41583-020-00379-8. Epub Oct. 12, 2020.

Ye et al., Apolipoprotein (apo) E4 enhances amyloid beta peptide production in cultured neuronal cells: apoE structure as a potential therapeutic target. Proc Natl Acad Sci U S A. Dec. 20, 2005;102(51):18700-5. doi: 10.1073/pnas.0508693102. Epub Dec. 12, 2005.

Bennett et al., Neuropathology of older persons without cognitive impairment from two community-based studies. Neurology. Jun. 27, 2006;66(12):1837-44.

Corder et al., Gene dose of apolipoprotein E type 4 allele and the risk of Alzheimer's disease in late onset families. Science. Aug. 13, 1993;261(5123):921-3.

Englund et al., White matter changes in dementia of Alzheimer's type. Biochemical and neuropathological correlates. Brain. Dec. 1988;111 ( Pt 6):1425-39.

Liu et al., Cholesterol involvement in the pathogenesis of neurodegenerative diseases. Mol Cell Neurosci. Jan. 2010;43(1):33-42.

Plemel et al., Mechanisms of lysophosphatidylcholine-induced demyelination: A primary lipid disrupting myelinopathy. Glia. Feb. 2018;66(2):327-347. doi: 10.1002/glia.23245. Epub Oct. 27, 2017.

Saher et al., Cholesterol: a novel regulatory role in myelin formation. Neuroscientist. Feb. 2011;17(1):79-93.

Segatto et al., Analysis of the protein network of cholesterol homeostasis in different brain regions: an age and sex dependent perspective. J Cell Physiol. Jul. 2013;228(7):1561-7.

Svennerholm et al., Membrane lipids, selectively diminished in Alzheimer brains, suggest synapse loss as a primary event in early-onset form (type I) and demyelination in late-onset form (type II). J Neurochem. Mar. 1994;62(3):1039-47.

Vlkolinsky et al., Decreased brain levels of 2',3'-cyclic nucleotide-3'-phosphodiesterase in Down syndrome and Alzheimer's disease. Neurobiol Aging. Jul.-Aug. 2001;22(4):547-53.

* cited by examiner

FIG. 9A     FIG. 9B

APOE4 IMPAIRS MYELINATION VIA ALTERED CHOLESTEROL BIOSYNTHESIS AND TRANSPORT IN OLIGODENDROGLIA

RELATED APPLICATIONS

This application claims priority under 35 U.S.C. § 119(e) to U.S. Provisional Patent Application No. 63/160,877 filed Mar. 14, 2021, which is hereby incorporated by reference in its entirety.

GOVERNMENT SUPPORT

This invention was made with Government support under Grant No. AG062377, R01 AG058002, AG054012, U01 NS110453 awarded by the National Institutes of Health (NIH), and under Grant No. DMS1407562 awarded by the National Science Foundation (NSF). The Government has certain rights in the invention.

BACKGROUND

Alzheimer's disease is a chronic neurodegenerative disease having symptoms most commonly including memory loss, difficulties with language, and cognitive impairment. Despite the present and looming toll on society, we have no effective therapies for AD or related dementias. The complexity of AD pathology presents a major challenge to development of therapeutics. AD pathogenesis proceeds over the course of several decades and arises through diverse genetic etiologies. Our understanding of the mechanisms has largely been limited to the effects of early-onset familial AD (fAD). Despite this growing genetic awareness, the next steps are currently missing. Even for the strongest risk factor for sAD, APOE4, the mechanisms underlying its association with AD or related pathologies is largely unclear. Therefore, there are currently no therapeutic or lifestyle interventions to mitigate genetic and nongenetic risk for developing AD.

SUMMARY

Oligodendrocytes (OLs) are specialized brain cells that insulate and protect neurons and thereby support vital processes such as learning and memory. A single-cell transcriptomic analysis of post-mortem human brains revealed that oligodendrocytes and myelination are one of the most prominently dysregulated cell-types and processes in the brain of a patient with Alzheimer's Disease (AD). However, the role of myelin degeneration in the etiology of AD and the underlying pathological mechanisms remain largely unknown. Using multiple complementary in vitro and in vivo approaches, the underlying factors influencing AD and the relation to the strongest genetic risk factor for AD, APOE4, on myelination and oligodendrocytes, was examined. Single-cell transcriptomic and biochemical studies of post-mortem human brains revealed that APOE4-carriers have significant downregulation in myelin-associated genes and proteins compared to non-carriers. Young and aged mice harboring human APOE4 exhibited significantly reduced axonal myelination compared to APOE3 mice. It was discovered herein that cholesterol biosynthesis and transport are dramatically altered in oligodendrocytes from APOE4-carriers. Using iPSC-derived oligodendroglia disrupted cholesterol biosynthesis and transport was found to be a cell autonomous feature that does not require extrinsic signals from the environment or other cell-types. An in vitro model of human myelination was developed and tested in combinatorial experiments mixing and matching isogenic APOE3 and APOE4 cell-types to demonstrate that APOE4 oligodendroglia are sufficient to mediate hypomyelination and that cholesterol biosynthesis and transport are rate-limiting steps in axonal myelination. Thus, altered cholesterol pathways in APOE4 oligodendrocytes have been demonstrated herein to impair myelination.

In some aspects methods of improving myelination, and thus, treating disease such as AD using compounds that deplete cholesterol are provided. For instance, small molecules such as cyclodextrins have been shown to reverse APOE4-associated cholesterol phenotypes and lead to significantly improved myelination.

APOE4 alters cholesterol synthesis and transport in oligodendrocytes which impairs myelination. In some aspects, a method for promoting myelination in a subject is provided and comprises administering to the subject a compound comprising a cyclodextrin or analogs thereof including the pharmaceutically acceptable salts thereof in an effective amount to promote myelination in the subject.

In some embodiments, the subject has Alzheimer's disease. In some embodiments, the subject has CAA. In some embodiments, the subject has been diagnosed with Alzheimer's disease. In some embodiments, the method further comprises determining whether a subject has or is at risk of developing hypomyelination by identifying the subject as APOE4 positive.

In some embodiments, the daily dose administered to the patient is between 1 and 50 mg and the dose is administered once daily. In some embodiments, the method comprises a pharmaceutically acceptable salt that is a hydrochloride.

In some embodiments, the compound is administered as an immediate release formulation. In some embodiments, the compound is administered as a sustained release formulation. In some embodiments, the Alzheimer's disease is mild to moderate Alzheimer's disease. In some embodiments, the Alzheimer's disease is moderate to severe Alzheimer's disease. In some embodiments, the method further comprises administering another therapeutic agent.

In some aspects the invention is a method of treating Alzheimer's Disease in a subject by administering to the subject an effective amount of an ACSL1 inhibitor to restore purinergic signaling and treat Alzheimer's disease in the subject. In some embodiments the ACSL1 inhibitor is selected from the group consisting of Triacsin C, 2-Fluoropalmitic acid and Adenosine 5'-hexadecylphosphate. In some embodiments the ACSL1 inhibitor is administered orally.

In other aspects, a method of treating Alzheimer's Disease in a APOE4 positive subject by administering to the subject an effective amount of a cholesterol inhibitor to treat Alzheimer's disease in the subject is provided. In some embodiments the subject is identified as APOE4 positive prior to treatment. In some embodiments the subject is homozygous for APOE4. In some embodiments the subject is not otherwise in need of treatment with a cholesterol inhibitor.

The details of one or more embodiments of the invention are set forth in the description below. Other features or advantages of the present invention will be apparent from the following drawings and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIG. 1A: Study cohort description by AD pathology groups: APOE3/3 carriers (grey), APOE3/4 carriers (pink), APOE4/4 carriers (red) are balanced according to positive pathological diagnosis (black outline) and negative diagnosis (no outline). The APOE4/4 group comprised 3 male and 4 female subjects, all with an AD diagnosis. AD status was defined based on both a positive pathological diagnosis (high amyloid and tau pathology) and cognitive diagnosis of Alzheimer's dementia (final consensus cognitive diagnosis, cogdx=4). FIG. 1B: Schematic depiction of APOE-associated pathway database curation process. FIG. 1C: Top APOE-associated pathways with expression changes associated with APOE4 (nominal p-value<0.05, linear model). Top 10 pathways are shown by cell type in order of APOE4 effect size. The APOE4 effect indicates the direction and strength of E4-associated expression changes, controlling for multiple potential confounders. Numeric values indicate significant absolute APOE4 effects at nominal p-value<0.05. Positive (negative) E4 effect values indicate increase (decrease) in expression. FIG. 1D: Overrepresentation analysis of lipid-related terms within top pathways altered by APOE4. P-values were computed per cell type using a hypergeometric test. Dotted line indicates p-value=0.05. FIG. 1E: Overrepresentation analysis of cholesterol/sterol-related terms within lipid-associated pathways altered by APOE4. Cholesterol pathways are recurrently altered only in oligodendrocytes.

FIG. 2A: Dose-dependent correlation of cholesterol biosynthesis gene activity in oligodendrocytes by APOE4 allele (p-value<0.05, linear model). FIG. 2B: Individual-level correlation between global end-stage cognitive scores and cholesterol biosynthesis gene activity in post-mortem oligodendrocytes (pathway activity score computed by GSVA on genes shown in FIG. 2A). The Pearson correlation coefficient was collectively computed on all APOE3/3, APOE3/4, and APOE4/4 subjects in this study. APOE4 carriers (3/4 and 4/4) are denoted. FIG. 2C: Representative images of cholesterol and myelin basic protein (MBP) staining in prefrontal cortex from APOE4 carriers and non-carriers. Cholesterol localization was analyzed across 4-7 individuals for each genotype. Total bodipy-cholesterol and percent of bodipy-cholesterol signal within 1 um of an MBP-positive axon were quantified using Imaris software. Scale bar 10 μm. Dots represent individuals. Bars depict means from all individuals per genotype. P values calculated using a student's t test. FIG. 2D: Representative images of cholesterol staining, with markers for microglia (IBA1), astrocytes (GFAP) and oligodendrocytes (OLIG2) in human prefrontal cortex of APOE4-carriers, Bodipy-cholesterol staining was quantified for cell type based on localization with each cell specific markers. Scale bar 10 μm. Bars depict means from different biological replicates. P values calculated using a student's t test. Outline in OLIG2 panel depicts 2 μm silhouette around nucleus that was quantified for the presence of bodipy-cholesterol FIG. 2E: Representative images of Fillipin and WGA-membrane staining in APOE3/3 and APOE4/4 iPS-derived oligodendroglia, having altered cholesterol localization in APOE4/4 iPS-derived oligodendroglia. Fillipin intensity was quantified for the cell membrane (localized with WGA) and intracellular compartment (in between membrane and nucleus) (n=6 replicates from independent experiments). Scale bar 50 μm. Bars depict means from independent biological replicates. P values calculated using a student t's test. FIG. 2F: Representative Bodipy staining for lipid droplets. Scale bar=10 μm. Lipid droplets were quantified in two different isogenic sets of APOE3/3 and APOE4/4 oligodendroglia that were generated from different individuals. Dots represent biological replicates and bars show means. P-values are from student's t test. FIG. 2G: Volcano plot summarizing all of the results from mass spectrometry-based lipidomic profiling of iPS-derived APOE3/3 and APOE4/4 oligodendroglia. Cholesteryl ester were the most differentially altered class of lipids with 15 species of cholesteryl esters upregulated in APOE4 oligodendroglia. Cholesteryl esters are highlighted in red. FIG. 2H: Barplot depicting the number of differentially (p<0.01) detected lipid species for each lipid class, showing that cholesteryl esters are the most frequently differentially expressed class of lipids in APOE4/4 oligodendroglia. FIG. 2I: Box plots depicting the levels of all four detected cholesteryl esters in post-mortem human corpus callosum from APOE3 (APOE3/3, females, n=3) and APOE4 carriers (APOE4/4, females, n=3), as detected by mass-spectrometry. Detected cholesteryl ester species are represented on the y-axis and corresponding abundancy per individual on the x-axis. Numbers along the y-axis encode the specific cholesteryl ester. The first number indicates the carboxylate position, which connects the fatty acid to the cholesterol hydroxyl group. The second number indicates the frequency of unsaturated fatty acid bonds. Log FC values (p-values, linear model) in order of y-axis from top to bottom=0.61 (0.53), 0.93 (0.38), 0.33 (0.33), 0.19 (0.46).

FIG. 3A: Log 2 fold changes for differentially expressed (p-adj<0.05, Wilcoxon rank sum test) myelin-associated or cholesterol-associated genes in human post-mortem oligodendrocytes from APOE3/4-carrier relative to APOE3/3-carriers. FIG. 3B: staining for myelin basic protein (MBP) and neurofilament in prefrontal cortex from APOE4-carriers and non-carriers (n=6 individuals per genotype) reveals a decrease in immunoreactivity against MBP in APOE4-carriers. MBP immunoreactivity quantified using ImageJ software. Bars represent means from different mice. P value calculated using a student's t test. FIG. 3C: TEM on sections from human corpus callosum of APOE4-carriers (n=3) and non-carriers (n=3), revealing an increase in g-ratio in APOE4-carriers. Scale bar 500 μm. g-ratio quantified using ImageJ software. Violin plot with dots representing g-ratios of axons from each genotype. P value calculated using Wilcoxon test. FIG. 3D: TEM on corpus callosum from APOE3 (n=3) and APOE4 (n=3) knock-in mice at 6 months of age, revealing an increase in g-ratio in APOE4KI mice. g-ratio quantified using ImageJ software. Scale bar 500 μm. Violin plot with dots representing g-ratios for axons from each genotype. P value calculated using Wilcoxon test. FIG. 3E: Representative images of co-cultures of isogenic iPS-derived APOE4/4 and APOE3/3 oligodendroglia/iNeuron after six weeks in culture, Mbp staining that localized within 1 μm of neurofilament was quantified and presented in the graph on the right. In vitro co-cultures were performed using two different isogenic iPSC sets with reciprocal editing strategies that were derived from different individuals. Scale bar 50 μm. Dots represent means from independent experiments. Mbp localization with neurofilament was quantified using ImageJ. P value calculated using a student's t test. FIG. 3F: Co-culture of APOE3/3 oligodendrocytes and APOE4/4 neurons, and APOE4/4 oligodendrocytes and APOE3/3 neurons, and quantification of percent MBP staining that localizes within 1 μm of neurofilament staining. Representative images showing staining for MBP, neurofilament, and DAPI. Scale bar 50 μm. Dots represent means from independent experiments. Axonal MBP quantified using ImageJ. P value calculated using a student's t test. FIG. 3G: Diagram summarizing results of in vitro experiments.

FIG. 4A: Representative images showing APOE4/4 iPSC-derived oligodendroglia treated with simvastatin, atorvastatin, Total bodipy-cholesterol was quantified for each condition and normalized to number of nuclei using ImageJ software. Bars represent means from biological replicates. P values calculated using one-way ANOVA with Bonferroni post-hoc analysis. Scale bar 50 μm. FIG. 4B: Bodipy-cholesterol and cell WGA-membrane staining on control and cyclodextrin-treated iPS-derived APOE4/4 oligodendrocyte cultures. The number of intracellular droplets was quantified and normalized to the number of nuclei for each sample. Bars represent means from biological replicates. P value calculated using student's t test. FIG. 4C: MBP and neurofilament immunohistochemistry on cyclodextrin-treated co-cultures of iPS-derived APOE4/4 oligodendroglia and neurons relative to APOE3 co-cultures. Scale bar 10 μm. Axonal MBP expression quantified using Imaris software. Bars represent means. P values calculated using ANOVA with Bonferroni post-hoc analysis. FIG. 4D: Bodipy-cholesterol and Olig2 staining in cyclodextrin-treated APOE4 mouse brain, and quantification showing reduction of bodipy-cholesterol staining in cyclodextrin-treated mice. N=4 and 5 mice per treatment condition. Bars represent means from different mice. P-value calculated using student's t-test. Scale bar 50 μm. FIG. 4E: Mbp and bodipy-cholesterol staining in cyclodextrin-treated APOE4KI mouse brain. Quantification showing an increase in cholesterol-myelin colocalization, and overall increase in Mbp, in cyclodextrin-treated APOE4KI female mice. Mbp-cholesterol colocalization quantified using Imaris software. Mbp staining quantified using Image J software. Bars represent means. P-value calculated using student's t test. Scale bar 50 μm. FIG. 4F: TEM on corpus callosum from control and cyclodextrin-treated APOE4KI mouse brain (n=4 and 5 per condition), showing a decrease in g-ratio in cyclodextrin-treated APOE4KI mice. g-ratio calculated using Image J software. P-value calculated using student's t-test. FIG. 4G: Novel object recognition task with control and cyclodextrin-treated APOE4 female mice (n=12 and 14, respectively), showing cyclodextrin-treated APOE4KI mice have a significantly increased preference for novel object compared to control APOE4KI mice. Preference calculated by dividing time the animal used its nose to interact with the novel object, over the total time it spent interacting with either object. Dots represent individual mice. Bars represent means. P value calculated using student's t test.

FIG. 5A: Distribution of pathology variables in cohort. FIG. 5B: Distribution of PMI and age at death variables in cohort. FIG. 5C: Experimental and computational workflow of the single-cell analysis involves single nuclei isolation and sequencing, followed by computational analysis for sub-clustering and cell type annotation. FIG. 5D: Expanded view of immune and vascular cell types. FIG. 5E: Cell-type-specific marker gene expression projected onto two-dimensional representation of cell space. FIG. 5F: Enrichment of markers from two independent datasets (columns) within genes with preferential gene expression across annotated cell groups (rows). FIG. 5G: Pair-wise correlations of cell-type-specific individual-level transcriptomic profiles (average expression values across cells of a given type). FIG. 5H: Distribution of inter-subject correlation values by cell type. FIG. 5I: Median number of cells per subject by cell type. FIG. 5J: Fraction of subjects lacking cells of a given type. FIG. 5K: Individual distributions across cell types. FIG. 5L: Individual cell-type fractions organized by pathological diagnosis and APOE genotype.

FIG. 6A: Overview of the top APOE4 dysregulated pathways (p-value<0.05, linear model, top 50 largest effect sizes in at least one cell type), when controlling for multiple confounders. Pathways are split into unique and shared based on whether the pathway is significantly dysregulated (p-value<0.05, linear model) in a single (unique) or more (shared) cell types. Bold pathways are discussed in results. FIG. 6B: Overview of APOE4-perturbed genes by cell type. Annotated genes correspond to differentially expressed (p-value<0.05, negative binomial mixed model) representative members of bold pathways shown in FIG. 6A.

FIG. 7A: GSVA transcriptional activity scores of APOE-associated pathways that show cell-type-specific patterns. FIG. 7B: Distribution of APOE-associated pathway activity by cell type. FIG. 7C: Frequency with which different annotated pathway categories are dysregulated by APOE4 (related to FIG. 1C). FIG. 7D: Cell-type-specific enrichment of lipid processes among top 10 dysregulated pathways shown in FIG. 1C. FIG. 7E: Frequency with which different lipid categories are dysregulated by APOE4 (related to FIG. 1D). FIG. 7F: Cell-type-specific enrichment of cholesterol processes among dysregulated pathways shown in FIG. 1D. FIG. 7G: Overrepresentation of APOE-related pathways within genes differentially expressed in APOE4 relative to APOE3 in human post-mortem oligodendrocytes as estimated by a negative binomial mixed model. FIG. 7H: Transcriptional activity of cholesterol-related pathways across cell types as estimated by GSVA. FIG. 7I: Evaluation of transcriptional activity score computation by estimating cell type marker scores. Observed cell type scores values (top) are contrasted with activity scores of same-sized randomly chosen gene sets (bottom). FIG. 7J: Transcriptional activity scores estimated for randomly chosen gene sets of same size and number as those observed in APOE-associated pathways shown in FIG. 7A and FIG. 7B. Unlike patterns observed for APOE-associated pathways in FIG. 7A, no pattern of cell type preferential expression is observed under random expectation.

FIG. 8A: Comparison of the relative expression of myelination genes (MYRF, MOG, PLP1, PLLP, MAG, OPALIN) in iPSC-derived brain cell types and aggregated cell type gene expression profiles from post-mortem human brain single-nucleus data. FIG. 8B: Staining of MBP, MYRF, and MOG in iPS-derived oligodendroglia. Scale bar 10 um. FIG. 8C: Principal component analysis of relative gene expression for in vivo post-mortem brain cells and iPSC-derived counter parts. iPSC-derived oligodendroglia cluster with human brain oligodendrocytes, OPCs, and astrocytes in the lower right quadrant. FIG. 8D: iPS-derived oligodendroglia exhibits a high degree of similarity to post-mortem human OPCs and oligodendrocytes (Wilcoxon test p-values shown). Distributions represent distances between each post-mortem cell type (x-axis) and iPSC oligodendroglia in scaled gene space. FIGS. 8E-8F: iPS-derived oligodendroglia, and post-mortem human oligodendrocytes, express high levels of myelination (FIG. 8E) and cholesterol (FIG. 8F) associated genes relative to other cell types (gene set activity scores by GSVA on scaled expression values using genes show in FIG. 8A or FIG. 8G, Wilcoxon test p-values shown). FIG. 8G: Heatmap comparing expression of cholesterol associated genes in iPS-derived oligodendroglia, and post-mortem human brain oligodendrocytes relative to other cell types. FIG. 8H: Differential expression (post-mortem: Wilcoxon rank sum test, iPSC: DESeq2, p-adj<0.05) of cholesterol-associated genes in APOE4 vs APOE3. APOE4 is associated with similar dysregulation in iPS-derived oligodendroglia and post-mortem human oligodendrocytes. FIG. 8I: Perturbed cholesterol/sterol-associated pathways in APOE4 iPSC oligodendroglia (linear model, p-value<0.05). FIG. 8J: Gene expression levels of ACAT2 and CYP46A1 genes from bulk sequencing of iPS-derived APOE3/3 and APOE4/4 oligodendroglia (n=3 biological replicates per genotype). Bars depict means from different biological samples. P values calculated using a student's t test. FIG. 8K: Cholesterol and lysosome (Lysotracker-Red) staining in isogenic iPS-derived APOE3/3 and APOE4/4 oligodendroglia. FIG. 8L: Cholesterol staining, percent cholesterol in lysosome, and lysosomal area quantification in two isogenic pairs of iPS-derived APOE3/3 and APOE4/4 oligodendroglia. Quantification performed using ImageJ software. Bars represent means. P value calculated using Student's t test.

FIGS. 9A-9C: Cyclodextrin treatment in APOE4 knock-in mice. FIG. 9A: Bodipy (neutral lipid) staining in control and cyclodextrin-treated iPS-derived APOE4 oligodendrocytes. The number of droplets was normalized to total cell number for each image. Bars represent mean number of droplets per a cell for each condition. P value calculated using Student's t test. FIG. 9B: CYP46A1 gene expression in APOE4 oligodendroglia treated with control, cyclodextrin, atorvastatin, or simvastatin for two weeks. Bars represent means. P value calculated using Student's t test. FIG. 9C: Activity traces and quantification of distance moved, velocity, and duration in center of control and cyclodextrin-treated APOE4 animals during open field test. FIG. 10A: Myelin-associated gene expression changes in APOE3 vs APOE4 post-mortem oligodendrocytes for individuals with and without AD pathology (Wilcoxon rank sum test, p-adj<0.05). FIG. 10B: Western blot for Mbp protein in APOE3KI (n=4) and APOE4KI (n=4) mouse cortex at six months of age. Total area and intensity of bands normalized to GAPDH was quantified. Bars represent means. P value calculated using Student's t-test. FIG. 10C: Immunohistochemistry for Mbp in APOE3KI and APOE4KI mouse hippocampus at nine months of age, and quantification. Quantification performed using ImageJ software. Bars represent means. P value calculated using Student's t test. Scale bar 200 μm. FIG. 10D: Diagram of co-culture of iPS-derived neurons and oligodendroglia. Created with BioRender.com FIG. 10E: MBP and 04 expression in iPS-derived oligodendroglia at two and six weeks after co culture with NGN2 induced neurons in a 3-dimensional extracellular matrix. Far right image depicts TEM of in vitro myelination cultures at 6 weeks showing the presence of structures consistent with axonal myelination. Scale bar 10 μm. FIG. 10F: MBP and neurofilament expression in APOE3/3, APOE4/4 and APOEKO co-cultures after three weeks in culture. Scale bar 10 um. FIG. 10G: Axon area in APOE3/3, APOE4/4 and APOEKO co-cultures. Bars represent means. P value calculated using Student's t test. Scale bar 10 μm.

DETAILED DESCRIPTION

Figure 1A:
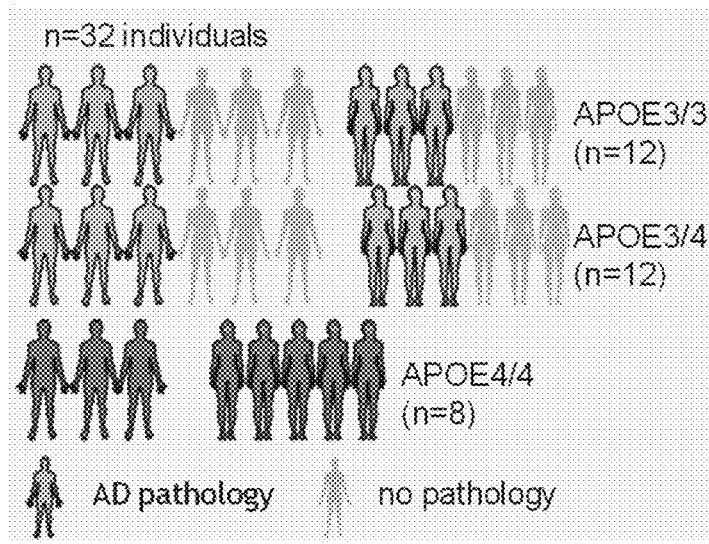
FIGS. 1A-1E: Human PFC snRNA-seq profiling and dysregulation of APOE4-associated pathways.

APOE4 is a strong genetic risk factor for late-onset Alzheimer's disease (AD), However, the cellular and molecular mechanisms by which APOE4 contributes to AD risk remain largely unknown. It has been discovered that regulation of a cholesterol pathway in oligodendrocytes and other related cells plays an important role in the myelination process in subjects, in particular in APOE4 positive individuals. The ability to regulate this pathway has important implications for the treatment of disorders such as myelination hyporesponsive disorders, learning disorders and memory disorders. As shown in the Examples presented herein the pathogenic mechanisms of APOE4, were analyzed by performing single-nucleus RNA-sequencing of the post-mortem human prefrontal cortex from multiple individuals. Differential expression and pathway analysis revealed that APOE4 is strongly associated with dysregulation of cholesterol homeostasis across multiple cell types, with oligodendrocytes being the most impacted. Strikingly, in human and mouse brains, APOE4 oligodendrocytes contained aberrant intracellular accumulations of cholesterol, whereas in non-carriers, cholesterol preferentially localized to the oligodendrocyte cell membrane along myelinated neuronal tracts. Mass-spectrometry-based lipidomic analysis further revealed that APOE4 oligodendrocytes and APOE4 human post-mortem brain tissue had elevated levels of cholesteryl esters, associated with intracellular storage of cholesterol as lipid droplets.

Cholesterol transport and bioavailability are rate-limiting steps in axonal myelination. It is further demonstrated that both APOE4 human and mouse brains were hypomyelinated relative to non-carriers. In order to identify compounds useful for addressing disease associated with hypomyelination, small molecules known to facilitate cholesterol transport were tested and found to reduce cholesterol accumulation in APOE4 oligodendrocytes, increased axonal myelination, and improved memory in APOE4 mice. It has been demonstrated herein that cholesterol homeostasis in APOE4 oligodendrocytes is highly dysregulated and hypomyelination is a key APOE4-associated phenotype.

Further, in some aspects the disclosure presents the manipulation of transcription factors to treat neurodegenerative disease by regulating an immune checkpoint. It is shown herein that neuronal media induced expression in APOE3 iMGLs of the proto-oncogene CBL which has been shown to repress pro-inflammatory activation pathways in immune cells, and also PRDM1 (Positive Regulatory Domain 1, also known as BLIMP1) which was identified as a repressor of interferon gene expression, with depletion of PRDM1 being associated with aberrant and exacerbated activation of inflammatory reactions. The induction of these inflammatory repressors by APOE3 iMGLs (i.e. CBL, PRDM1 and ELKS) in response to spheroid conditioned media may act as an immune checkpoint to mitigate downstream inflammatory responses despite the induction of immune master regulators. Failure to evoke these inducible-TFs suggests that this immune checkpoint is left unchecked in APOE4 iMGLs, which may lead to overactivation of downstream immune effectors.

Thus, it was discovered, quite unexpectedly, that therapeutic compounds that disrupt intracellular cholesterol levels such as cyclodextrins or analogs thereof were capable of modulating axonal myelination and are thus useful for treating diseases associated with cognitive decline and memory deficits. In some aspects the invention is a method for reversing APOE4-associated cholesterol phenotype such as hypomyelination pathologies in a subject, by administering to the subject a compound comprising cyclodextrin or analogs thereof including the pharmaceutically acceptable salts thereof in an effective amount to treat the disorder in the subject. The APOE4-associated cholesterol phenotype may be myelination degeneration such as Alzheimer's Disease.

The terms reduce, interfere, inhibit, and suppress refer to a partial or complete decrease in activity levels relative to an activity level typical of the absence of the inhibitor. For instance, the decrease may be by at least 20%, 50%, 70%, 85%, 90%, 100%, 150%, 200%, 300%, or 500%, or by 10-fold, 20-fold, 50-fold, 100-fold, 1000-fold, or 104-fold.

The small molecules can be administered using any means known in the art, including inhalation, intraperitoneally, intravenously, intramuscularly, subcutaneously, intrathecally, intraventricularly, orally, enterally, parenterally, intranasally, or dermally.

In some embodiments the subjects are identified as having or at risk of developing myelination degeneration based on genotype, whether they are APOE4 positive and successfully treated with the compounds described herein. If the subject is APOE4 positive, those subjects are at risk of developing disorders such as CAA or Alzheimer's disease.

The compounds useful herein, in some aspects, are cyclodextrins or analogs thereof. In some embodiments an analog is structural analog such as sulfonated cyclodextrins alpha-cyclodextrins, beta-cyclodextrins, gamma cyclodextrins, methyl-beta-cyclodextrins, hydroxypropyl beta-cyclodextrins, and sulfobutylether beta-cyclodextrins.

In other aspects the invention is a method of treating Alzheimer's Disease in a subject by administering to the subject an effective amount of an ACSL1 inhibitor to restore purinergic signaling and treat Alzheimer's disease in the subject. Acyl CoA synthetases (ACSL), particularly ACSL1, are major enzymes responsible for converting free fatty acids taken in through diet into several lipid subclasses usable as energy sources, cellular building blocks or cellular communication means. Free fatty acids, such as SFA, can only be utilized by the body after their activation or catalyzation by Acyl-CoA. The use of ACSL inhibitors was also shown to stop TNF signaling, and thus stopping inflammatory responses in vitro. In some embodiments the ACSL1 inhibitor is Triacsin C, 2-Fluoropalmitic acid or Adenosine 5'-hexadecylphosphate. In some embodiments the ACSL1 inhibitor is administered orally.

In other aspects, a method of treating Alzheimer's Disease in a APOE4 positive subject by administering to the subject an effective amount of a cholesterol inhibitor to treat Alzheimer's disease in the subject is provided.

Cellular pathways that govern the regulation of lipid and cholesterol homeostasis have been explored in the pathogenesis of AD. However, brain cholesterol is synthesized locally and independent of circulating plasma cholesterol pool due to its impermeability through the blood-brain-barrier (BBB). Inconsistent results regarding the ability of cholesterol-lowering statins to act as neuroprotective agents have been reported. High intracellular levels of cholesterol due to its poor export by APOE4 may lead to incorporation of cholesterol at the mitochondrial membrane. Whether deficits in mitochondrial metabolic function is the cause or the effect of lipid accumulation in APOE4 microglia remains unresolved. We have observed here that in microglia and in astrocytes derived from APOE4 iPSCs cholesterol accumulates extracellularly. Although the mechanism by which cholesterol and other lipids may accumulate extracellularly in APOE4 glia is not clear, astrocytes activated with pro-inflammatory stimuli have recently been reported to secrete saturated lipids contained within APOE and APOJ lipoproteins that are toxic to neurons. Based on the data disclosed herein demonstrating that the metabolic profile of microglia is associated with its pro-inflammatory state, therapies aimed at reprogramming microglial metabolism may prove to be imperative in curbing inflammation and halting neurodegeneration in AD. The use of systemic or local cholesterol inhibition to treat Alzheimer's disease and other neurodegenerative disease is disclosed herein.

A cholesterol inhibitor is any organic substance or an inorganic substance that inhibits cholesterol synthesis and/or accumulation in circulation. The organic substance may be for instance, a low-molecular-weight compound, a nucleic acid, a peptide, or a protein. In some embodiments the cholesterol inhibitor is a cholesterol synthesis inhibitor which may inhibit cholesterol synthesis by targeting at least one factor selected from the group consisting of an acetyl-CoA acetyltransferase, an HMG-CoA synthase, and an HMG-CoA reductase. Examples of cholesterol synthesis inhibitors that inhibits cholesterol synthesis by targeting the HMG-CoA reductase include Pravastatin, Simvastatin, Fluvastatin, Atorvastatin, Pitavastatin, Rosuvastatin, Cerivastatin, Lovastatin, and Mevastatin. Pravastatin, Simvastatin, Fluvastatin, Atorvastatin, Pitavastatin, and Rosuvastatin, are commercially available products. The cholesterol synthesis inhibitor may be a salt or a derivative of these compounds as well.

Cholesterol absorption inhibitors such as ezetimbe impair the intestinal reabsorption of both dietary and hepatically-excreted biliary cholesterol. Ezetimbe, for example, may be used for reducing low density lipoprotein cholesterol in patients.

In some embodiments the subject is identified as APOE4 positive prior to treatment. In some embodiments the subject is homozygous for APOE4. In some embodiments the subject is not otherwise in need of treatment with a cholesterol inhibitor.

Any of the compounds described herein may be used as salts. As used herein, the term "salt" refers to any and all salts and encompasses pharmaceutically acceptable salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In some embodiments, the methods are directed to treating or managing neurodegenerative diseases or disorders in which abnormal cholesterol synthesis and/or intracellular accumulation results in myelination degeneration and thus diseases, such as those diseases associated with learning and/or memory or Alzheimer's disease. In a non-limiting example, the compounds disclosed herein are administered to a patient diagnosed as having or at risk for developing an myelination degeneration or a disorder such as Alzheimer's disease, cerebral amyloid angiopathy (CAA), mild cognitive impairment, moderate cognitive impairment, and combinations thereof.

The term "myelination degeneration," as used herein, refers to a reduction in axonal myelination relative to normal levels of myelination. Myelination degeneration is associated with a group of diseases and disorders caused by or associated with loss of axonal myelination resulting from excessive cholesterol intracellular accumulation, in particular in oligodendrocytes. Such diseases include, but are not limited to, neurological disorders such as Alzheimer's Disease, diseases or conditions characterized by a loss of cognitive memory capacity such as, for example, mild cognitive impairment (MCI), Lewy body dementia, Down's syndrome, hereditary cerebral hemorrhage with amyloidosis (Dutch type), the Guam Parkinson-Demential complex and other diseases which are based on or associated with amyloid-like proteins such as progressive supranuclear palsy, multiple sclerosis, Creutzfeld Jacob disease, Parkinson's disease, HIV-related dementia, ALS (amyotropic lateral sclerosis), inclusion-body myositis, adult onset diabetes, endocrine tumor and senile cardiac amyloidosis, and various eye diseases including macular degeneration, drusen-related optic neuropathy, glaucoma, and cataract due to beta-amyloid deposition.

The subject may have been the subject has been diagnosed with the disease, such as Alzheimer's disease. In some embodiments the subject can be treated following diagnosis, at varying stage of the disease, or as a prophylactic measure in instances where genetic traits, family history, or other factors put the patient at risk for the neurodegenerative disease or disorder. Successful dosage amounts and schedules may be established and monitored by metrics indicative of effective treatment, for example the extent of inhibition, delay, prevention or reduction of symptoms such as cognitive decline, loss of myelination in the brain, and neurodegeneration which are detected following the initiation of treatment.

In some embodiments the subject is determined to be APOE4 positive. A number of genetic factors in early- and late-onset familial Alzheimer's disease have been documented. The ApoE4 allele is strongly associated with late-onset familial and sporadic Alzheimer's disease, with a reported allele frequency of 50%-65% in patients with Alzheimer's disease, which is approximately three times that in the general population and for other neurologic disorders. In addition to Alzheimer's disease, the ApoE4 allele has been implicated in other amyloid-forming disorders, including CAA.

Thus, in some embodiments the methods disclosed herein are useful for treating Alzheimer's disease. The methods of treatment may alleviate the pathological symptoms of Alzheimer's disease, including and not limited to amyloidβ accumulation or aggregation, brain cell aging, and (3) synapse loss. As used herein, the inhibiting accumulation and/or aggregation encompasses inhibiting aggregation by suppressing the production or synthesis of amyloid β and/or inhibiting accumulation by degrading already produced amyloidβ.

The deposition of extracellular amyloid plaques in the brain is a hallmark pathologic finding in Alzheimer's disease. These amyloid plaques are primarily composed of Abeta peptides generated by the sequential cleavage of amyloid precursor protein ("APP") via β and γ-secretase activity. Techniques and tools have been developed to visualize the presence of plaques in patients. For example, position emission tomography ("PET") scans using imaging agents, such $^{18}$F-florbetapir, that detect amyloid-beta can be used to detect the presence of amyloid in the brain.

A "subject" herein is typically a human. In certain embodiments, a subject is a non-human mammal. Exemplary non-human mammals include laboratory, domestic, pet, sport, and stock animals, e.g., mice, cats, dogs, horses, and cows. Typically, such subject or patient is eligible for treatment for amyloidosis. In one embodiment, such eligible subject or patient is one that is experiencing or has experienced one or more signs, symptoms, or other indicators of an amyloid disease or has been diagnosed with a disease, whether, for example, newly diagnosed, previously diagnosed or at risk for developing a disease such as Alzheimer's disease. Diagnosis of disease may be made based on clinical history, clinical examination, and established imaging modalities. A "patient" or "subject" herein includes any single human subject eligible for treatment who is experiencing or has experienced one or more signs, symptoms, or other indicators of disease. Intended to be included as a subject are any subjects involved in clinical research trials, or subjects involved in epidemiological studies, or subjects once used as controls.

The methods of treatment provided herein can be applied to subjects suffering from Alzheimer's disease. The subject may, in some embodiments have mild to moderate Alzheimer's disease. In other embodiments the subject may have moderate to severe Alzheimer's disease. The severity of the disease can be assessed using a number of diagnostic criteria known in the art, such as biomarkers. For instance, mild Alzheimer's disease or Stage 1 disease may be an asymptomatic patient characterized by PET or CSF positive for amyloid β, a Stage 2 disease may show downstream neurodegeneration biomarkers such as tau, FDG-PET, or structural MRI, and Stage 3 disease may present as amyloidosis plus neuronal injury and cognitive/behavioral decline.

In some aspects, the methods provided herein are methods of reducing or slowing decline due to Alzheimer's disease in patients suffering from early, mild, or mild to moderate Alzheimer's disease. In some embodiments, the decline is one or more of: clinical decline, cognitive decline, and functional decline. In some embodiments, the decline is a decline in cognitive capacity or cognitive decline. In some embodiments, the decline comprises a decline in functional capacity or functional decline. Various tests and scales have been developed to measure cognitive capacity (including memory) and/or function. In various embodiments, one or more test is used to measure clinical, functional, or cognitive decline. A standard measurement of cognitive capacity is the Alzheimer's Disease Assessment Scale Cognitive (ADAS-Cog) test, for example, the 12-item ADAS-Cog or ADAS-Cog12, or the 13-item ADAS-Cog or ADAS-Cog-13. Thus, in some embodiments, the reduction or slowing in decline in cognitive capacity (or cognitive decline) in patients being treated with the compounds of the invention is determined using the ADAS-Cog12 test. An increase in ADAS-Cog12 score is indicative of worsening in a patient's condition. In some embodiments, the reduction or slowing in cognitive decline in patients being treated with the compounds of the invention is determined by a Clinical Dementia Rating Scale/Sum of Boxes (CDR-SB) score. In some embodiments, reduction or slowing in functional decline (or decline in functional ability) in patients being treated with the compounds of the invention is determined using the Instrumental Activities of Daily Living (iADL) scale. In some embodiments, decline of one or more types is assessed and one or more of the foregoing tests or scales is used to measure reduction or slowing in decline.

Amyloid-positive subjects or patients may have brain amyloid load consistent with that seen in patients diagnosed with Alzheimer's disease. A subject suffering from mild cognitive impairment or Alzheimer's disease or having preclinical Alzheimer's disease, prodromal Alzheimer's disease, early or mild Alzheimer's disease, are typically subjects with an MMSE score of 20 or above (e.g., 20-30, 20-26, 24-30, 21-26, 22-26, 22-28, 23-26, 24-26, or 25-26) or with a Clinical Dementia Rating-Global Score (CDR-GS) of 0.5 or 1.0, and subjects with a Free and Cued Selective Reminding Test-Immediate Recall (FCSRT-IR) Cueing Index of 0.67 or above and a total free recall score of 27 or greater.

Several Alzheimer's disease-risk genes are expressed in cells that constitute the brain and may directly influence the accumulation and clearance of Aβ. In particular, Apolipoprotein E (APOE) protein is highly expressed in astrocytes and microglia of the brain. In humans, there are three genetic polymorphisms of APOE, E2, E3, and E4. The E4 isoform of APOE (APOE4) is the most significant known risk factor for CAA and sporadic Alzheimer's disease. In some embodiments, subjects are carriers of at least one ApoE4 allele ("ApoE4 carriers").

Alleviating a neurodegenerative disease includes delaying the development or progression of the disease or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a neurodegenerative disease includes initial onset and/or recurrence.

The compound is administered to the brain of the patient, either directly or indirectly by administration to other regions of the body. The compound may be administered directly by intracerebroventricular injection. The compound may be administered indirectly to the brain by administration through any route that delivers a compound to a body of a subject. In some embodiments the compound is administered as an immediate release formulation. In some embodiments the compound is administered as a sustained release formulation.

In some embodiments the subject is treated with another therapeutic agent. In one embodiment, the pharmacological agents that would, in combination with the compounds of the present invention, be most effective in treating or ameliorating one or more symptoms of amyloid disorders include, but are not limited to, Razadyne, Exelon, Aricept, Cognex, and Namenda, Parcopa, Mirapex, Requip, Apokyn, Eldepryl, Zelapar, Azilect, Comtan, Tasmar, Cogentin, Sinemet, Neupro, Symmetrel, Selegiline, Rasagilene, Stalevo, Apokyn, Parlodel, and Artane. In one embodiment, the pharmacological agents that would, in combination with the compounds of the present invention, be most effective in treating or ameliorating one or more symptoms of neurodegenerative disorders include, but are not limited to, Zarontin, Felbatol, Gabitril, Keppra, Lamictal, Lyrica, Neurontin, Dilantin, Topamax, Trileptal, Depakene, Depakote, Zonegran, Valium, Ativan, Klonopin, Fycompa, and Oxtellar XR. In one embodiment, the pharmacological agents that would, in combination with the compounds of the present invention, be most effective in treating or ameliorating one or more symptoms of neurodegenerative disorders include, but are not limited to, Xenazine, Haldol, Clozaril, Klonopin, Valium, Lexapro, Prozac, Sarafem, Zoloft, Lithobid, Depakene, Depakote, and Lamictal. In one embodiment, the pharmacological agents that would, in combination with the compounds of the present invention, be most effective in treating or ameliorating one or more symptoms of neurodegenerative disorders include, but are not limited to, Aricept, Reminyl, Exelon, Namenda, Risperdal, Zyprexa, and selective serotonin reuptake inhibitors (SSRIs). In one embodiment, the SSRIs are selected from the group consisting of Zimelidine, Celexa (citalopram), Lexapro, Luvox, Paxil (paroxetine), Prozac (fluoxetine), and Zoloft (sertraline).

Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. The pharmaceutical compositions to be used in the present methods can comprise pharmaceutically acceptable carriers, excipients, or stabilizers in the form of lyophilized formulations or aqueous solutions. (Remington: The Science and Practice of Pharmacy $20^{th}$ Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ (polysorbate), PLURONICS™ (poloxamers) or polyethylene glycol (PEG).

In one embodiment, the pharmaceutical formulations include those suitable for oral, parenteral (including subcutaneous, intradermal, intramuscular, intravenous, and intraarticular), inhalation (including fine particle dusts or mists which may be generated by means of various types of metered doses, pressurized aerosols, nebulizers or insufflators), rectal and topical (including dermal, transdermal, transmucosal, buccal, sublingual, and intraocular) administration, although the most suitable route may depend upon, for example, the condition and disorder of the recipient. Pharmaceutically acceptable excipients and salts are further described herein. In some embodiments the pharmaceutically acceptable salt is a hydrochloride.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compound or pharmaceutically acceptable salts thereof can also be delivered through the oral cavity by sublingual and/or buccal administration. Molded tablets, compressed tablets or freeze-dried tablets are exemplary forms which may be used. Exemplary compositions include those formulating the present compounds with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents, thickening agents and P-glycoprotein (P-gp) inhibitors. The formulations may be presented in unit-dose or multi-dose containers, for example sealed ampoules and vials, and may be stored in a freeze-dried (lyophilized) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremapnor. In one embodiment, compositions for parenteral administration comprise up to 15% Cremaphor and up to 85% alcohol. In one embodiment, compositions for parenteral administration comprise up to 50% Cremaphor and up to 50% alcohol. In one embodiment, compositions for parenteral administration comprise up to 15% Cremaphor and up to 85% ethanol. In one embodiment, compositions for parenteral administration comprise up to 50% Cremaphor and up to 50% ethanol. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers.

Excipients that can be included are, for instance, non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included.

Formulations for rectal administration may be presented as a retention enema or a suppository with the usual carriers such as cocoa butter, synthetic glyceride esters or polyethylene glycol. Such carriers are typically solid at ordinary temperatures but liquefy and/or dissolve in the rectal cavity to release the drug.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as disclosed herein. It should be understood that in addition to the ingredients particularly mentioned above, the formulations of this invention may include other agents conventional in the art having regard to the type of formulation in question, for example those suitable for oral administration may include flavoring agents.

The compound and/or pharmaceutically acceptable salts thereof are also suitably administered as sustained-release systems. Suitable examples of sustained-release systems of the invention include suitable polymeric materials, for example semi-permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracisternally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compounds and/or pharmaceutically acceptable salts thereof. These compositions exhibit certain biocompatibility features which allow a controlled release of the active substance.

The compounds/or pharmaceutically acceptable salts thereof may be delivered by way of a pump or by continuous subcutaneous infusions, for example, using a mini-pump. An intravenous bag solution may also be employed. The key factor in selecting an appropriate dose is the result obtained, as measured by improvements in one or more symptoms of neurodegenerative disorders of interest, or by other criteria for measuring control or prevention of one or more symptoms of neurodegenerative disorders of interest, as are deemed appropriate by the practitioner. In another aspect of the disclosure, compound and/or pharmaceutically acceptable salts thereof are delivered by way of an implanted pump.

Implantable drug infusion devices are used to provide patients with a constant and long term dosage or infusion of a drug or any other therapeutic agent. Essentially such device may be categorized as either active or passive. The compound and/or pharmaceutically acceptable salts thereof may be formulated as a depot preparation. Such a long acting depot formulation can be administered by implantation, for example subcutaneously or intramuscularly; or by intramuscular injection. Thus, for example, the compound and/or pharmaceutically acceptable salts thereof can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of the compound and/or pharmaceutically acceptable salts thereof may be administered as a single pulse dose, as a bolus dose, or as pulse doses administered over time. Thus, in pulse doses, a bolus administration of a compound of the invention is provided, followed by a time period wherein no compound of the invention is administered to the subject, followed by a second bolus administration. In specific, non-limiting examples, pulse doses of a compound of the invention are administered during the course of a day, during the course of a week, or during the course of a month.

In some embodiments the daily dose administered to the patient is between 1 and 50 mg and the dose is administered once daily. Therapeutically effective amount of the compound and/or pharmaceutically acceptable salts thereof will be dependent on the molecule utilized, the subject being treated, the severity and type of the affliction, and the manner and route of administration. For example, a therapeutically effective amount of the compound and/or pharmaceutically acceptable salts thereof may vary from about 0.001 mg/Kg to about 2000 mg/Kg body weight. In one embodiment, a therapeutically effective amount of the compound and/or pharmaceutically acceptable salts thereof may vary from about 0.01 mg/Kg to about 1 mg/Kg body weight. In one embodiment, a therapeutically effective amount of the compound and/or pharmaceutically acceptable salts thereof may vary from about 0.001 mg/Kg to about 0.9 mg/Kg body weight, about 0.8 mg/Kg body weight, about 0.001 mg/Kg to 0.7 mg/Kg body weight, about 0.001 mg/Kg to 0.6 mg/Kg body weight, about 0.001 mg/Kg to 0.5 mg/Kg body weight, about 0.001 mg/Kg to 0.4 mg/Kg body weight, about 0.001 mg/Kg to 0.3 mg/Kg body weight, about 0.001 mg/Kg to 0.2 mg/Kg body weight, about 0.001 mg/Kg to 0.1 mg/Kg body weight, about 0.001 mg/Kg to 0.09 mg/Kg body weight, about 0.001 mg/Kg to 0.08 mg/Kg body weight, about 0.001 mg/Kg to 0.07 mg/Kg body weight, about 0.001 mg/Kg to 0.06 mg/Kg body weight, about 0.001 mg/Kg to 0.05 mg/Kg body weight, about 0.001 mg/Kg to 0.04 mg/Kg body weight, about 0.001 mg/Kg to 0.03 mg/Kg body weight, about 0.001 mg/Kg to 0.02 mg/Kg body weight. 0.01 mg/Kg body weight, about 0.001 mg/Kg to 0.009 mg/Kg body weight, about 0.001 mg/Kg to 0.008 mg/Kg body weight, about 0.001 mg/Kg to 0.007 mg/Kg body, about 0.001 mg/Kg to 0.006 mg/Kg body, about 0.001 mg/Kg to 0.005 mg/Kg body weight, about 0.001 mg/Kg to 0.004 mg/Kg body weight, about 0.001 mg/Kg to 0.003 mg/Kg body weight, and about 0.001 mg/Kg to about 0.002 mg/Kg body weight. In one embodiment, a therapeutically effective amount of the compound and/or pharmaceutically acceptable salts thereof may vary from about 0.001 mg/Kg to about 20 mg/Kg body weight. In one embodiment, a therapeutically effective amount of the compound and/or pharmaceutically acceptable salts thereof may vary from about 0.001 mg/Kg to about 10 mg/Kg body weight. In one embodiment, a therapeutically effective amount of the compound and/or pharmaceutically acceptable salts thereof may vary from about 0.001 mg/Kg to about 5 mg/Kg body weight. In one embodiment, a therapeutically effective amount of the compound and/or pharmaceutically acceptable salts thereof may vary from about 0.001 mg/Kg to about 3 mg/Kg body weight. In one embodiment, a therapeutically effective amount of the compound and/or pharmaceutically acceptable salts thereof may vary from 0.001 mg/Kg to about 2 mg/Kg body weight. In one embodiment, a therapeutically effective amount of the compound and/or pharmaceutically acceptable salts thereof may vary from about 0.001 mg/Kg to about 30 mg/Kg body weight. In one embodiment, a therapeutically effective amount of the compound and/or pharmaceutically acceptable salts thereof may vary from about 0.001 mg/Kg to about 40 mg/Kg body weight. In one embodiment, a therapeutically effective amount of the compound and/or pharmaceutically acceptable salts thereof may vary from about 0.001 mg/Kg to about 50 mg/Kg body weight. In one embodiment, a therapeutically effective amount of the compound and/or pharmaceutically acceptable salts thereof may vary in a range selected from the group consisting of about 0.001 mg/kg body weight, about 0.002 mg/kg body weight, about 0.003 mg/kg body weight, about 0.004 mg/kg body weight, about 0.005 mg/kg body weight, about 0.006 mg/kg body weight, about 0.007 mg/kg body weight, about 0.008 mg/kg body weight, about 0.009 mg/kg body weight, about 0.010 mg/kg body weight, about 0.011 mg/kg body weight, about 0.012 mg/kg body weight, about 0.013 mg/kg body weight, about 0.014 mg/kg body weight, about 0.015 mg/kg body weight, about 0.016 mg/kg body weight, about 0.017 mg/kg body weight, about 0.018 mg/kg body weight, about 0.019 mg/kg body weight, about 0.20 mg/kg body weight, about 0.030 mg/kg body weight, about 0.040 mg/kg body weight, about 0.050 mg/kg body weight, about 0.060 mg/kg body weight, about 0.070 mg/kg body weight, about 0.080 mg/kg body weight, about 0.090 mg/kg body weight, about 0.010 mg/kg body weight, about 0.02 mg/kg body weight, about 0.03 mg/kg body weight, about 0.04 mg/kg body weight, about 0.05 mg/kg body weight, about 0.06 mg/kg body weight, about 0.07 mg/kg body weight, about 0.08 mg/kg body weight, about 0.09 mg/kg body weight, about 0.10 mg/kg body weight, about 0.2 mg/kg body weight, about 0.3 mg/kg body weight, about 0.4 mg/kg body weight, about 0.5 mg/kg body weight, about 0.6 mg/kg body weight, about 0.7 mg/kg body weight, about 0.8 mg/kg body weight, about 0.9 mg/kg body weight, about 1 mg/kg body weight, about 2 mg/kg body weight, about 3 mg/kg body weight, about 4 mg/kg body weight, about 5 mg/kg body weight, about 6 mg/kg body weight, about 7 mg/kg body weight, about 8 mg/kg body weight, about 9 mg/kg body weight, about 10 mg/kg body weight, about 11 mg/kg body weight, about 12 mg/kg body weight, about 13 mg/kg body weight, about 14 mg/kg body weight, about 15 mg/kg body weight, about 16 mg/kg body weight, about 17 mg/kg body weight, about 18 mg/kg body weight, about 19 mg/kg body weight, about 20 mg/kg body weight, about 21 mg/kg body weight, 22 mg/kg body weight, 23 mg/kg body weight, 24 mg/kg body weight, 25 mg/Kg body weight, about 50 mg/Kg body weight, about 75 mg/Kg body weight, about 100 mg/Kg body weight, about 125 mg/Kg body weight, about 150 mg/Kg body weight, about 175 mg/Kg body weight, about 200 mg/Kg body weight, about 225 mg/Kg body weight, about 250 mg/Kg body weight, about 275 mg/Kg body weight, about 300 mg/Kg body weight, about 325 mg/Kg body weight, about 350 mg/Kg body weight, about 375 mg/Kg body weight, about 400 mg/Kg body weight, about 425 mg/Kg body weight, about 450 mg/Kg body weight, about 475 mg/Kg body weight, about 500 mg/Kg body weight, about 525 mg/Kg body weight, about 550 mg/Kg body weight, about 575 mg/Kg body weight, about 600 mg/Kg body weight, about 625 mg/Kg body weight, about 650 mg/Kg body weight, about 675 mg/Kg body weight, about 700 mg/Kg body weight, about 725 mg/Kg body weight, about 750 mg/Kg body weight, about 775 mg/Kg body weight, about 800 mg/Kg body weight, about 825 mg/Kg body weight, about 850 mg/Kg body weight, about 875 mg/Kg body weight, about 900 mg/Kg body weight, about 925 mg/Kg body weight, about 950 mg/Kg body weight, about 975 mg/Kg body weight, and about 1000 mg/Kg body weight.

In some embodiments, a therapeutically effective amount of the compound and/or pharmaceutically acceptable salts thereof is selected from the group consisting of about 0.01 mg/m$^2$, about 0.02 mg/m$^2$, about 0.03 mg/m$^2$, about 0.04 mg/m$^2$, about 0.05 mg/m$^2$, about 0.06 mg/m$^2$, about 0.07 mg/m$^2$, about 0.08 mg/m$^2$, about 0.09 mg/m$^2$, and about 0.1 mg/m$^2$.

In some embodiments, a therapeutically effective amount of the compound and/or pharmaceutically acceptable salts thereof is selected from the group consisting of about 0.1 mg/m$^2$, about 0.2 mg/m$^2$, about 0.3 mg/m$^2$, about 0.4 mg/m$^2$, about 0.5 mg/m$^2$, about 0.6 mg/m$^2$, about 0.7 mg/m$^2$, about 0.8 mg/m$^2$, about 0.9 mg/m$^2$, about 1 mg/m$^2$, about 1.1 mg/m$^2$, about 1.2 mg/m$^2$, about 1.3 mg/m$^2$, about 1.4 mg/m$^2$, about 1.5 mg/m$^2$, about 1.6 mg/m$^2$, about 1.7 mg/m$^2$, about 1.8 mg/m$^2$, about 1.9 mg/m$^2$, about 2 mg/m$^2$, about 2.1 mg/m$^2$, about 2.2 mg/m$^2$, about 2.3 mg/m$^2$, about 2.4 mg/m$^2$, about 2.5 mg/m$^2$, about 2.6 mg/m$^2$, about 2.7 mg/m$^2$, about 2.8 mg/m$^2$, about 2.9 mg/m$^2$, and about 3 mg/m$^2$.

In some embodiments, a therapeutically effective amount of the compound and/or pharmaceutically acceptable salts thereof is selected from the group consisting of about 4 mg/m$^2$, about 5 mg/m$^2$, about 6 mg/m$^2$, about 7 mg/m$^2$, about 8 mg/m$^2$, about 9 mg/m$^2$, about 10 mg/m$^2$, about 11 mg/m$^2$, about 12 mg/m$^2$, about 13 mg/m$^2$, about 14 mg/m$^2$, about 15 mg/m$^2$, about 16 mg/m$^2$, about 17 mg/m$^2$, about 18 mg/m$^2$, about 19 mg/m$^2$, about 20 mg/m$^2$, about 21 mg/m$^2$, about 22 mg/m$^2$, about 23 mg/m$^2$, about 24 mg/m$^2$, and about 25 mg/m$^2$.

The practice of the present invention will employ, unless otherwise indicated, conventional techniques of molecular biology (including recombinant techniques), microbiology, cell biology, biochemistry and immunology, which are within the skill of the art.

EXAMPLES

In order that the invention described herein may be more fully understood, the following examples are set forth. The examples described in this application are offered to illustrate the methods, compositions, and systems provided herein and are not to be construed in any way as limiting their scope.

Example 1. APOE4 Impairs Myelination Via Cholesterol Dysregulation in Oligodendrocytes Introduction Late onset Alzheimer's disease (AD) accounts for more than 95% of the disease, with approximately 50 million cases worldwide[1]. The heritability of AD is estimated between 50 and 80%, suggesting that after age, genetics is the dominant risk factor for AD[2]. Several genome-wide association studies (GWAS) have identified genetic variants associated with increased risk of AD[3,4]. Among these variants, single nucleotide polymorphisms in the APOE gene show the strongest association with AD[3-6]. Across the human population, there are three alleles of the APOE gene (E2, E3, and E4). APOE3 is the most frequent allele (79%) and is not associated with increased AD risk. The APOE4 allele differs from APOE3 by a single amino acid (Cys112 to Arg112); however, one copy of APOE4 increases the risk of AD 3 to 4 times, and homozygous APOE4/APOE4 carriers have an 8 to 12 fold increased risk of developing AD[5,8]. The APOE4 allele is present in approximately 14% of the general population[9], but is enriched in the AD population by 40-50%[10-14], suggesting a substantial causal connection to AD. Therefore, elucidating the molecular and cellular pathways underlying APOE4-associated pathogenesis could reveal therapeutic opportunities for a large portion of the AD population.

APOE4 is associated with increased amyloid-β deposition, hyperphosphorylation of tau, regulation of tau uptake, and accelerated cognitive decline[15-20], but the mechanisms by which APOE4 mediates these effects are not fully understood. APOE primarily functions as a lipid and cholesterol transporter. The APOE4 polymorphism alters accessibility of the lipid binding region, which interferes with its cholesterol and lipid transport capacity[21-24]. When Alois Alzheimer first described AD, he noted lipid inclusions in glial cells[25]. Consistent with this, recent in vitro studies have found that APOE4 causes accumulation of unsaturated triglycerides and lipid droplets in iPSC-derived astrocytes[26]. Despite this long-standing association, the mechanistic connection between lipid and cholesterol abnormalities, APOE4, and AD pathogenesis have remained unclear[27].

Insight into APOE4-mediated pathogenesis is complicated by the fact that APOE is differentially expressed across nearly all cell-types of the human brain and leads to widespread cell-autonomous and non-autonomous dysregulation of biological processes[28-33]. To resolve this complexity, the prefrontal cortex (BA10) was profiled from APOE4-carriers and non-carriers using single-nucleus RNA-sequencing, generating a comprehensive reference of the biological processes dysregulated in the post-mortem APOE4 brain. This transcriptomic approach was complemented with phenotypic analysis of isogenic (iPSC) models and humanized APOE knock-in mouse studies. Through this integrated computational and genetic-experimental approach, key molecular and cellular pathways affected by APOE4 in the human brain were discovered and validated. These results reveal that APOE4 profoundly alters cholesterol homeostasis in human and mouse oligodendrocytes, impairs myelination, and correlates with cognitive impairments. It was established that pharmacological manipulation of cholesterol transport reverses cholesterol defects and improves myelination and behavioral outcomes in mice, thus providing new insight into the mechanistic connection between APOE4, cholesterol, and AD pathogenesis.

Results

Single-Cell Transcriptomic Profiling of APOE4 Post-Mortem Brains

Figure 5A:
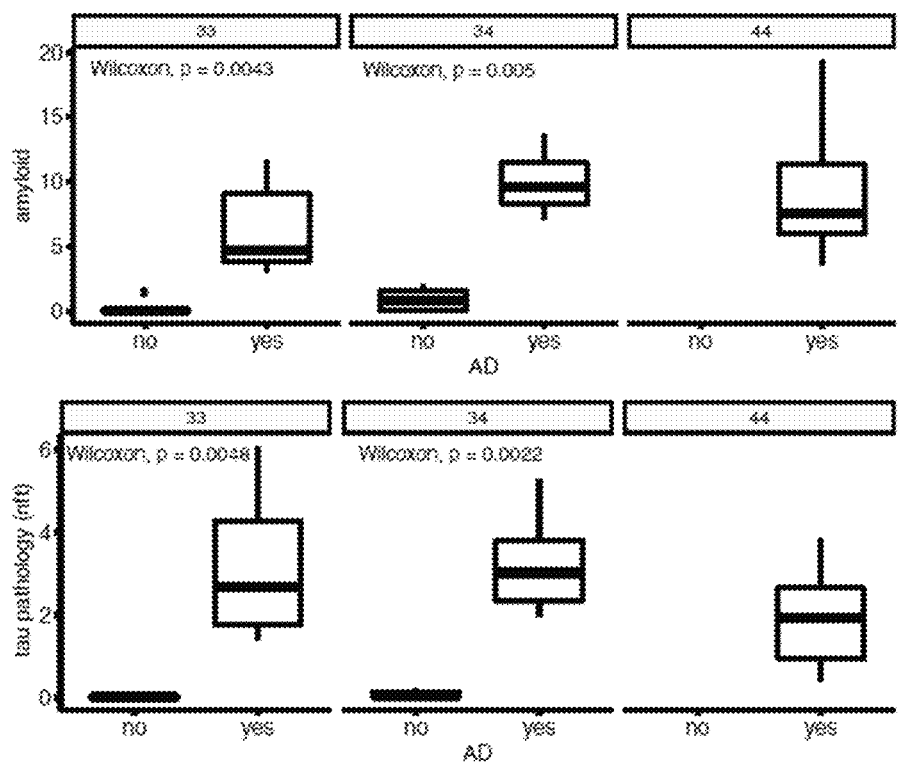
FIGS. 5A-5L: Subject-level metadata and single-cell annotation quality control.
Figure 5B:
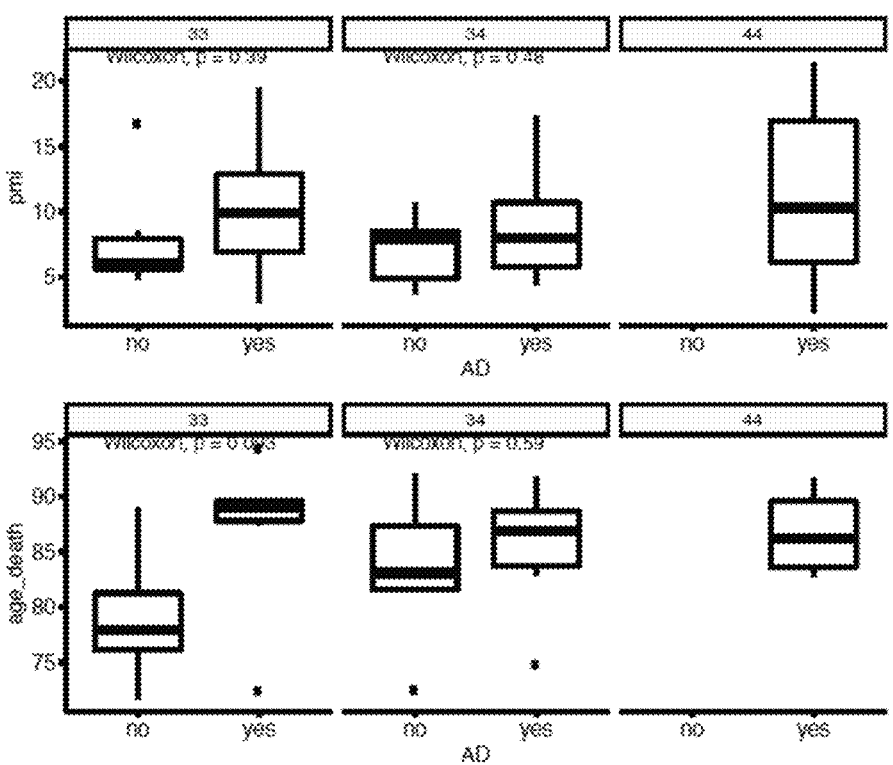
Figure 5C:
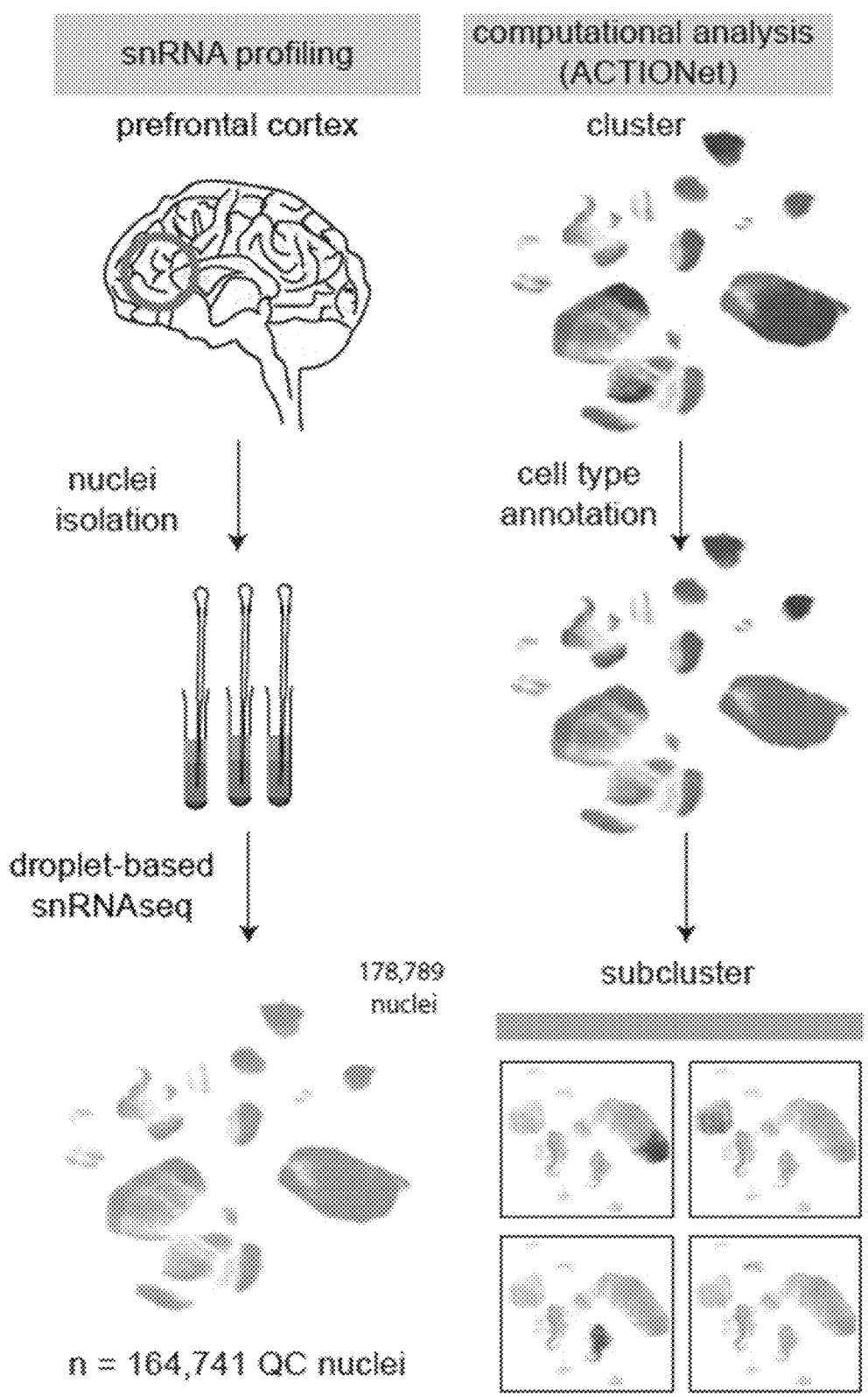

It was first sought to determine the effect of APOE4 on gene expression in the aged human brain. A sample of 32 subjects was selected from the Religious Order Study (ROS) or the Rush Memory and Aging Project (MAP), collectively known as ROSMAP[34], including two subgroups with 12 APOE3/3 and 12 APOE3/4 carriers each, and one subgroup with 8 APOE4/4 carriers. Given APOE4-carriers have higher rates of AD, the APOE3/3 and APOE3/4 subgroups were balanced by AD diagnosis (n=6 each for positive and negative diagnoses of AD), and gender (3 male and 3 female each) (FIG. 1A). All AD subjects presented high levels of both amyloid and neurofibrillary tangle (Tau) pathology and there were no significant differences in age or post-mortem intervals between APOE3/3, and APOE3/4 groups (FIGS. 5A-5B). For each individual, post-mortem tissue samples extracted from the prefrontal cortex were obtained, region BA10, and performed single-nucleus RNA sequencing (snRNAseq) using the 10× Genomics Chromium platform, producing a total of 178,789 (164,741 after quality control) single-nucleus transcriptomes (FIG. 5C).

Cellular Diversity of the Human Prefrontal Cortex

Figure 5D:
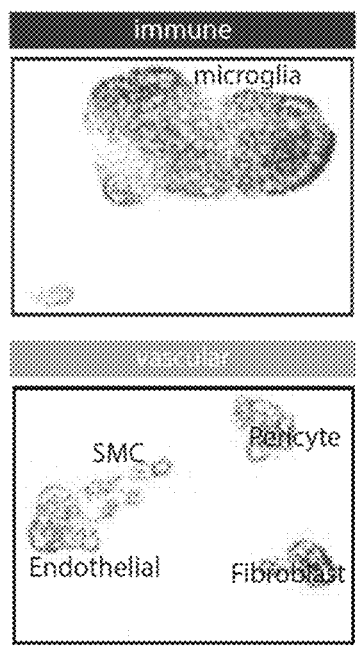
Figure 5E:
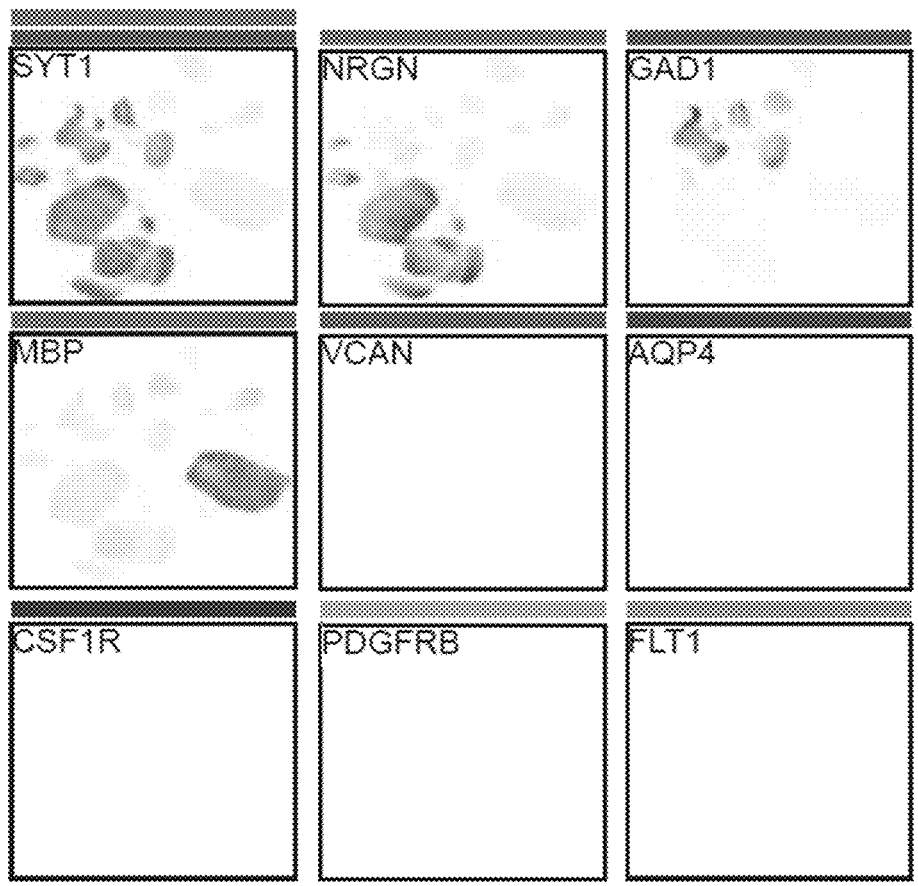
Figure 5F:
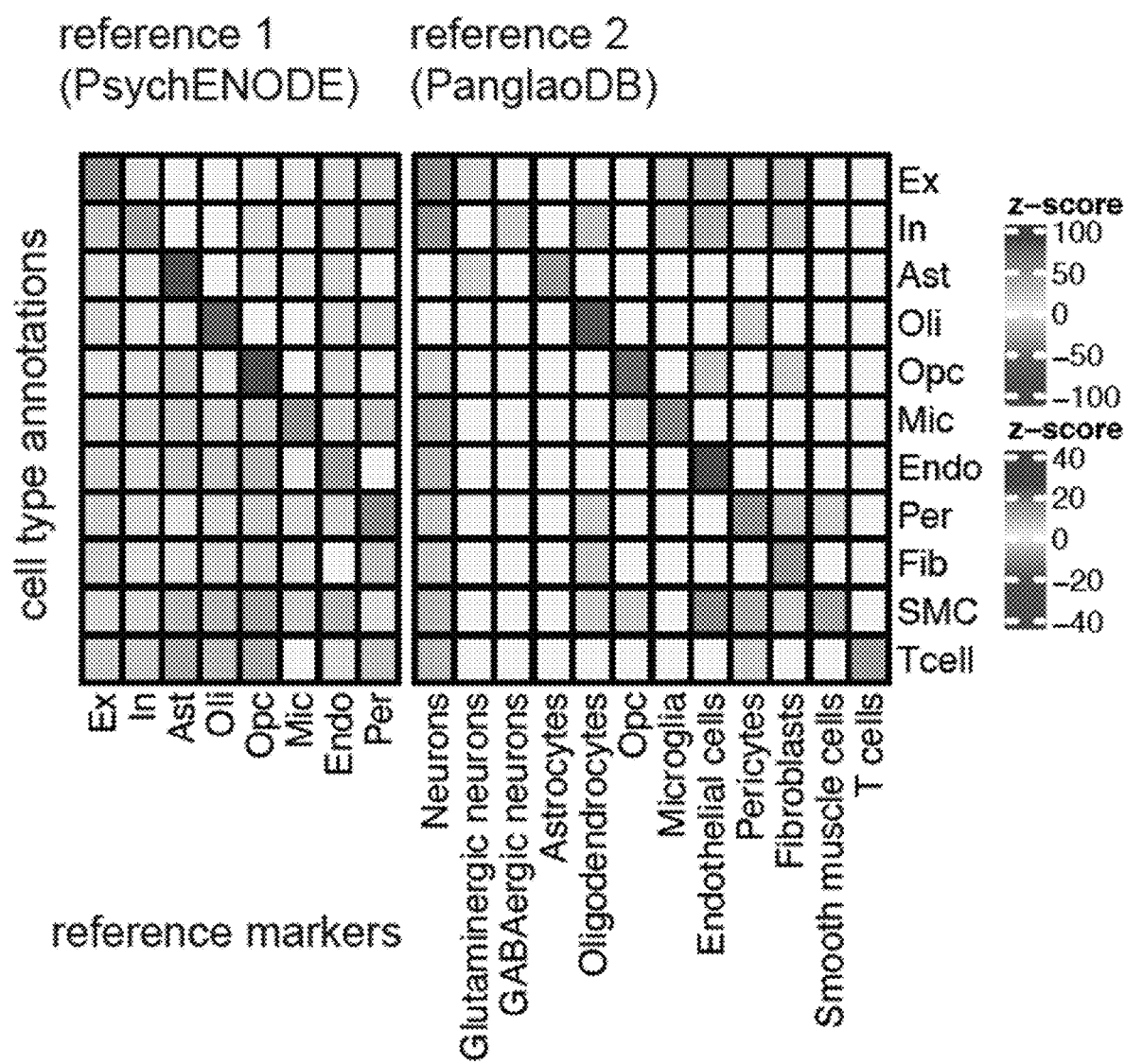
Figure 5G:
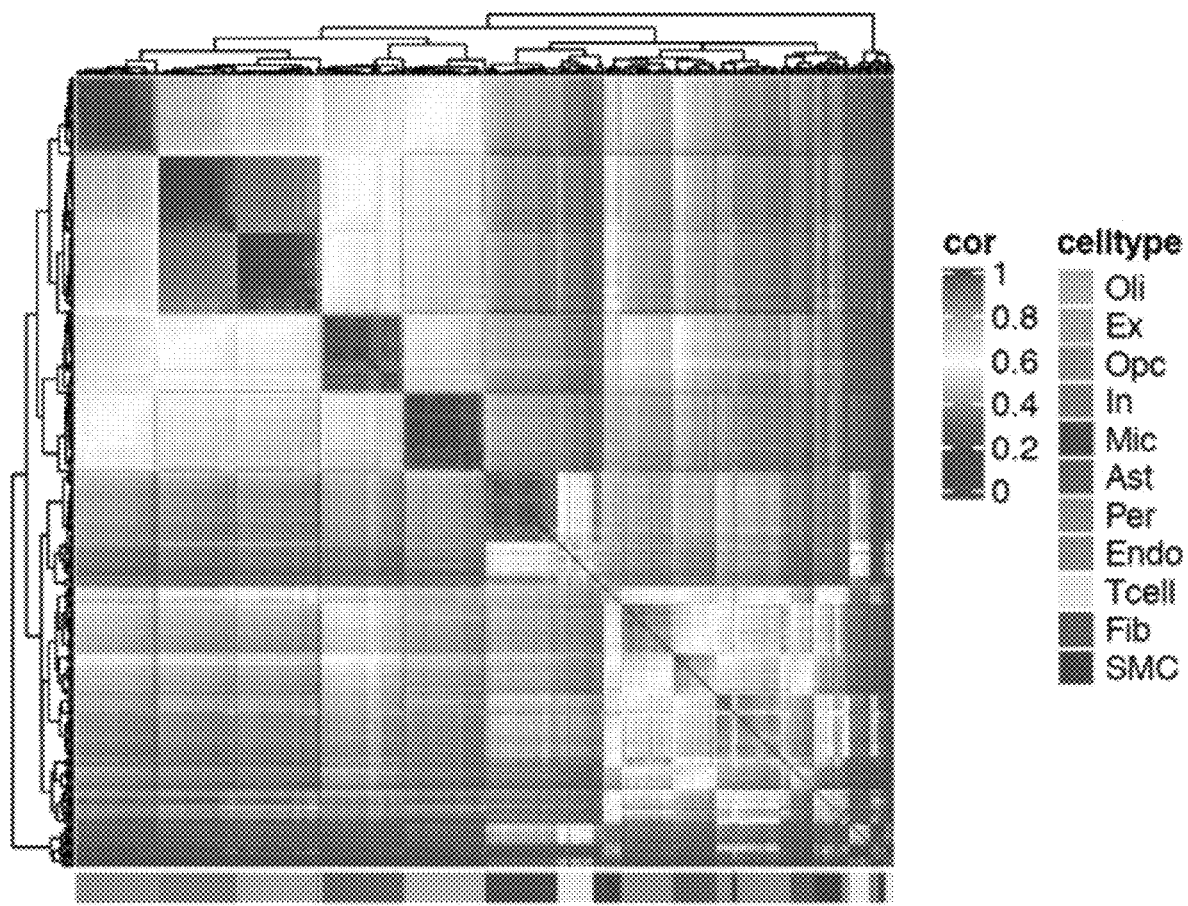
Figure 5H:
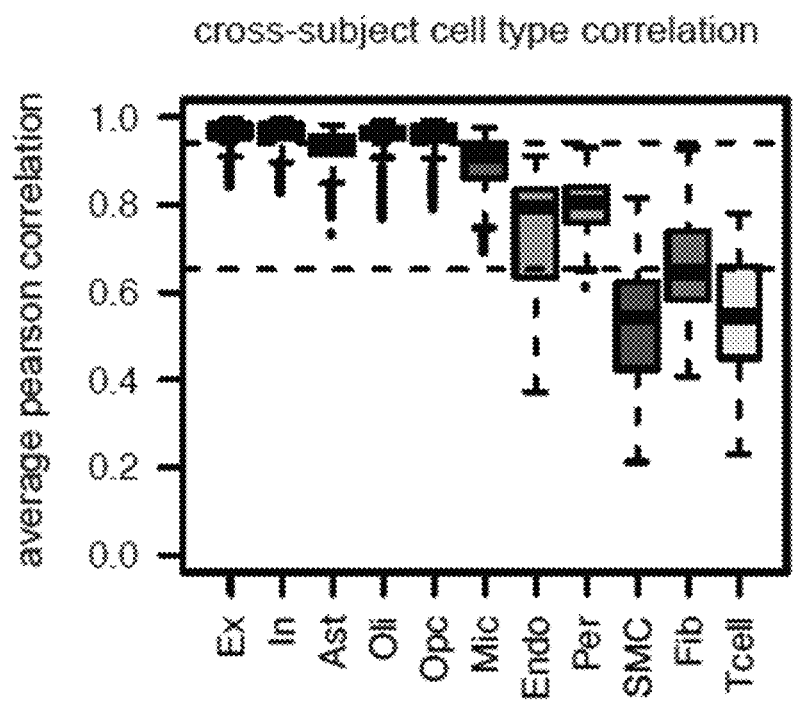
Figure 5I:
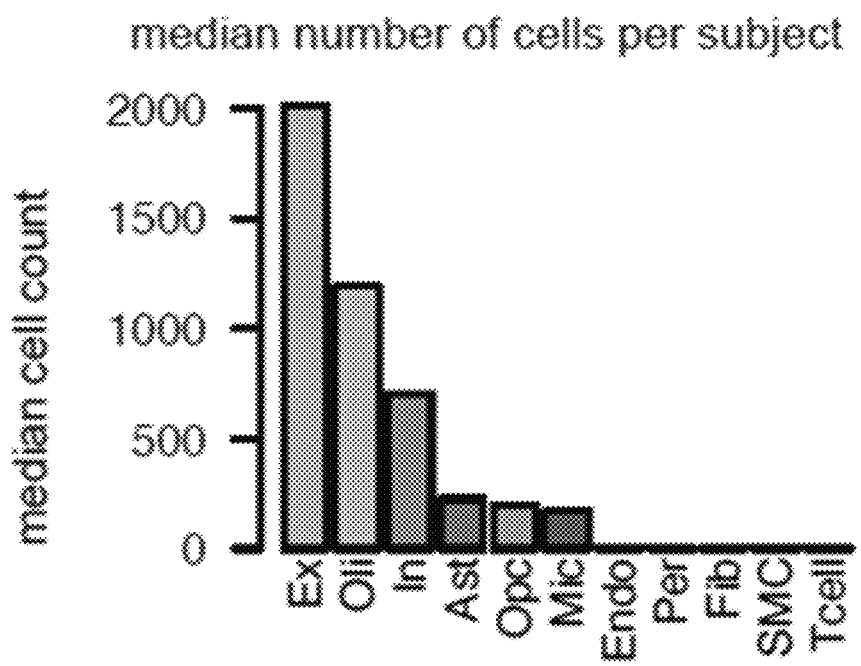
Figure 5J:
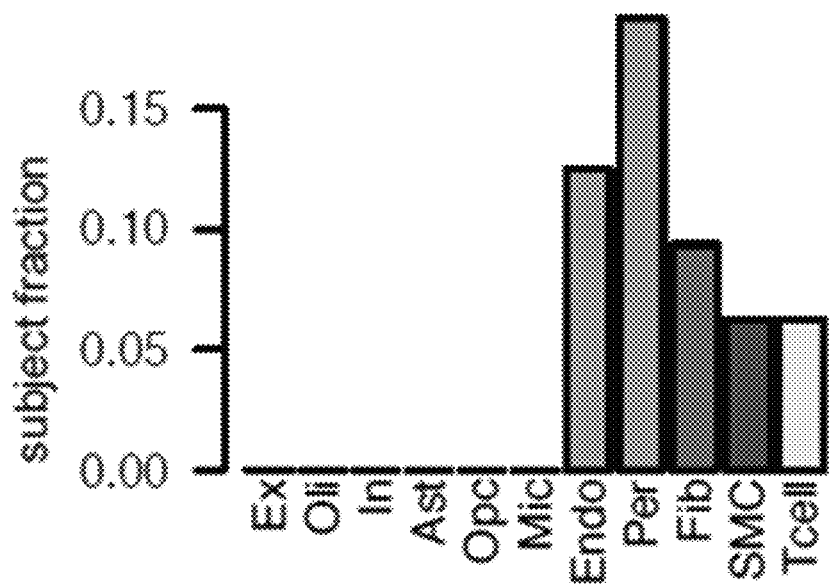
Figure 5K:
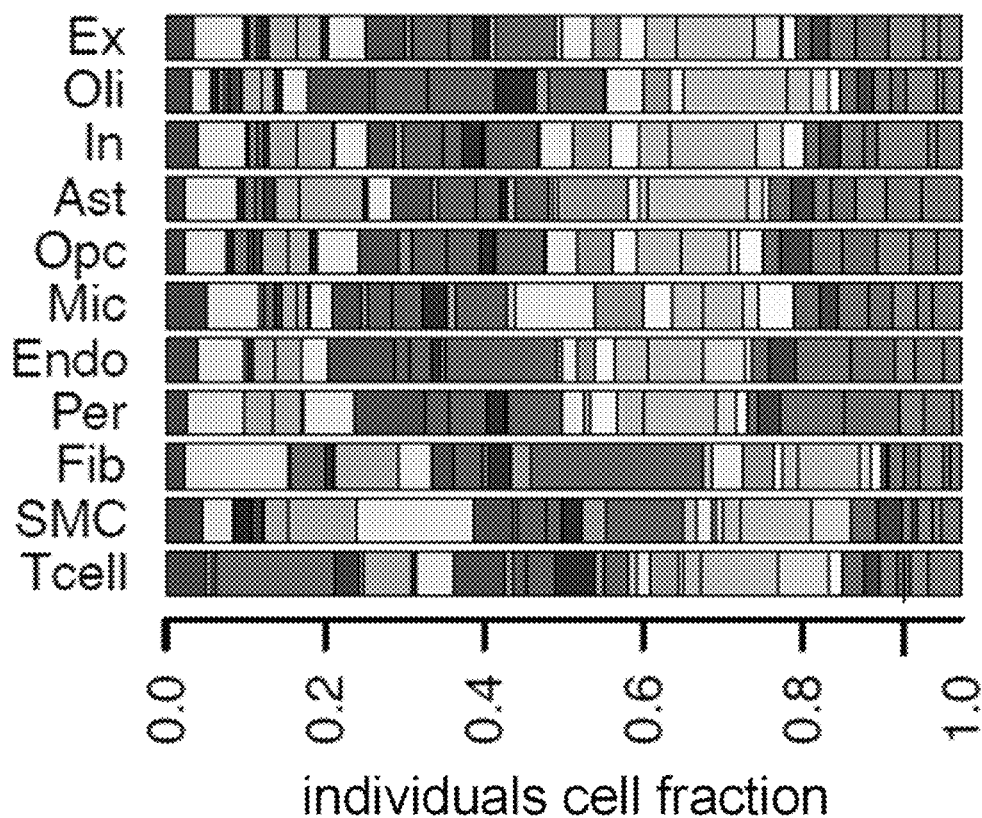
Figure 5L:
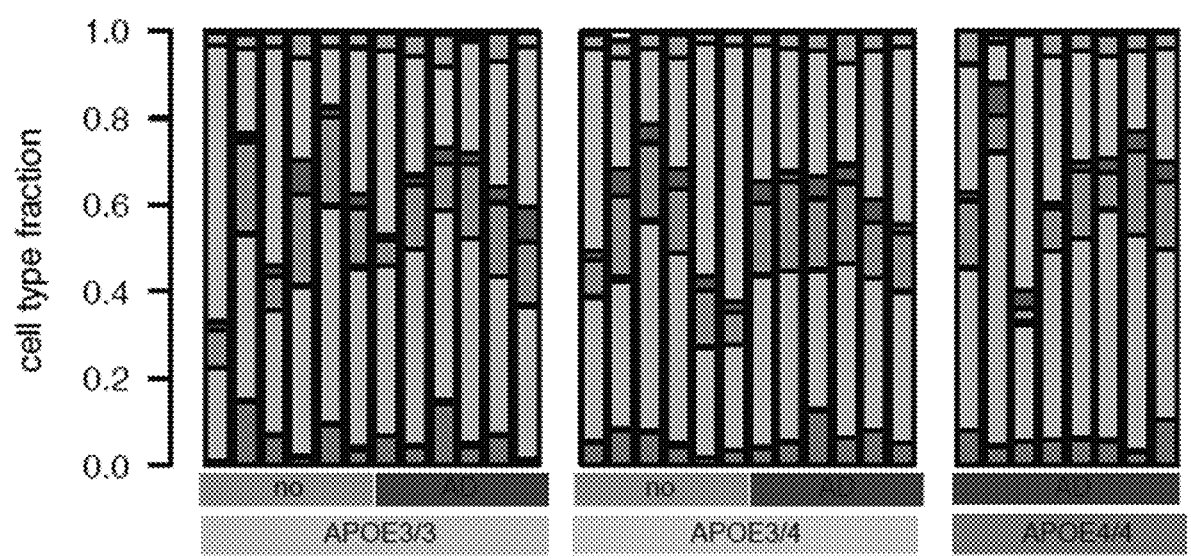

To investigate the cell-type specific effects of APOE4, the cellular diversity across all subjects were first characterized. The major cell types and subtypes were identified and annotated through two rounds of graph-based clustering analysis (FIG. 5C). The first round identified both excitatory (Ex, NRGN+) and inhibitory (In, GAD1+) neurons (SYT1+), astrocytes (Ast, AQP4+), oligodendrocytes (Oli, MBP+), oligodendrocyte progenitor cells (OPC, VCAN+), microglia (Mic, CSF1R+), and a heterogeneous population of vascular cell types (FIGS. 5D-5E). All annotations were reproducibly supported by expression patterns of curated marker genes[35,36] (FIG. 5E S2). To dissect cellular heterogeneity at higher resolution, each cell type population was sub-clustered, which identified multiple subgroups for each type, including T-cell (Tcell, CD247+), Pericyte (Per, PDGFRB+), Endothelial cells (End, FLT1+), Smooth muscle cell (SMC, CALD1+), and Fibroblast (Fib, ABCA9+) (FIG. 5D). Integrating annotations at both levels, labels were defined for 11 cell types supported by both individual gene marker expression and significant enrichment (FDR<0.01, permutation test) of curated marker sets (FIG. 5F). Cell type expression profiles were strongly correlated between individual donors (average Pearson r=0.94 and r=0.65 for high and low-abundant cell types, respectively) (FIGS. 5G-5H). Low-abundant cells (Tcell, End, Per, Fib, SMC) were not detected in a small fraction of subjects (average fraction across cell types=0.1), and had relatively low cell counts when detected (9.3 vs 850.2 cells on average across cell types and subjects for low-, high-abundant; respectively) (FIGS. 5I-5J). Therefore, lowly abundant cell types were not considered in downstream analyses. Highly abundant cell types were well-represented across donors, irrespective of AD or genotypic background, with reproducible proportions in most cases (FIGS. 5J-5L).

APOE4 Influences a Wide Range of Molecular Processes Across Cell Types

Figure 6A:
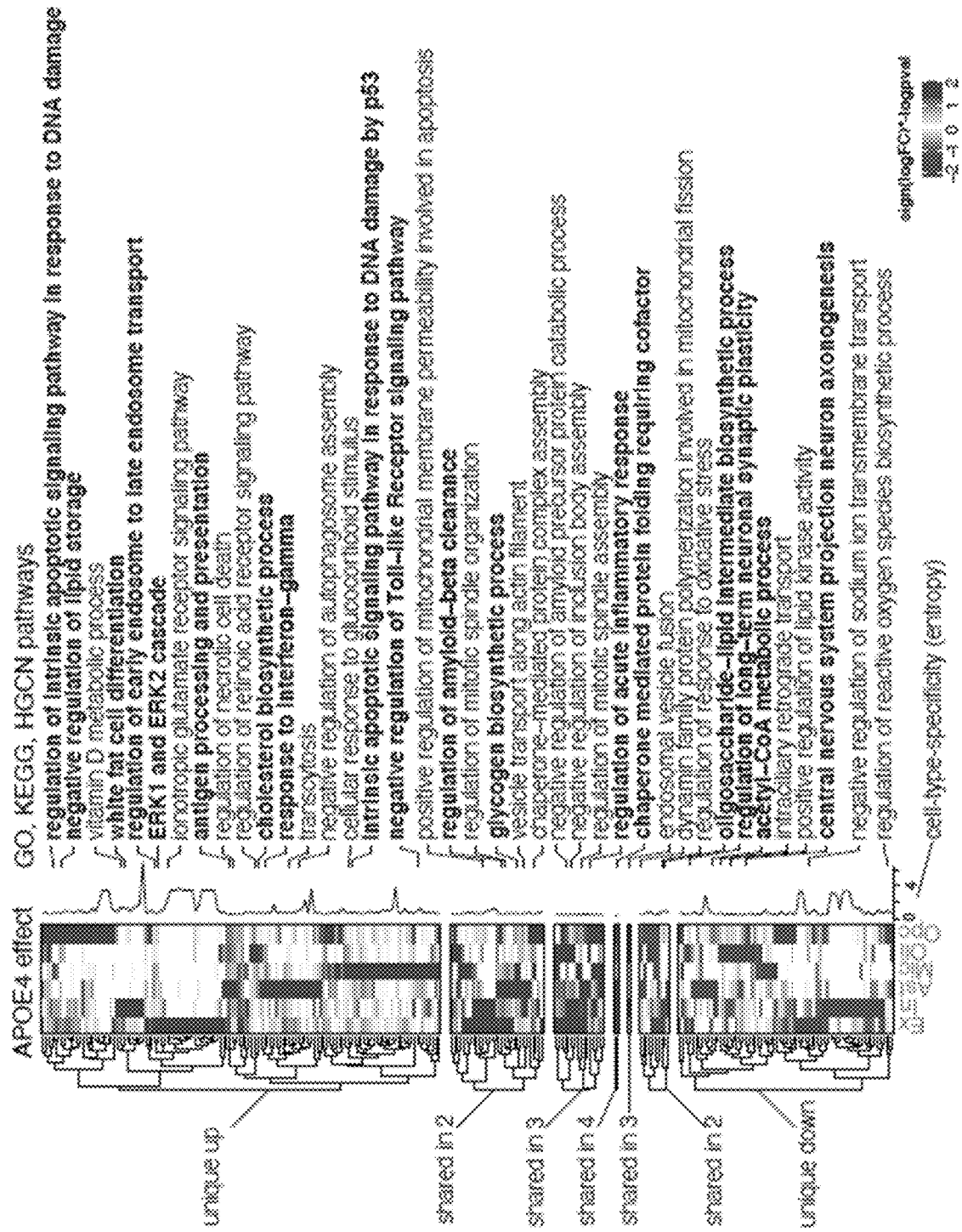
FIGS. 6A-6B: Cell-type-specific and broadly dysregulated pathways and genes in APOE4 human post-mortem cells.

APOE has diverse biological functions that influence molecular pathways across multiple cell types. Therefore, it was first sought to assess the transcriptional effects of APOE4 on each cell type. To determine the effect of APOE4 on molecular processes, an extensive collection of curated molecular pathways were leveraged (N=5,400, including GO, KEGG, and HGCN databases). For each cell type, gene expression values were aggregated into pathway activity scores, and the effect of APOE4 on each score was estimated while controlling for sex, PMI, pathology, and additional covariates using a multivariate linear model (Methods). A total of 253 APOE4-perturbed molecular processes were identified (p-value<0.05, top 50 largest effect sizes in at least one cell type) (FIG. 6A). A subset of these processes was affected only in one cell type (cell-type specific, unique), while others were more broadly dysregulated across multiple cell types (broad, at least 2 cell types).

This analysis revealed that APOE4 dysregulated biological processes in nearly every cell type. For example, regulation of acute inflammatory response (e.g. C1R, C5AR1) was upregulated across multiple cell types including oligodendrocytes, OPCs, and astrocytes. Other inflammatory processes were also upregulated in several APOE4 cell types, such as response to interferon-gamma in astrocytes and negative regulation of Toll-like receptor signaling in microglia. This demonstrates that APOE4 is broadly associated with regulation of inflammatory phenotypes across multiple cell types (FIGS. 6A-6B), consistent with previous reports[37,38 39].

Figure 6B:
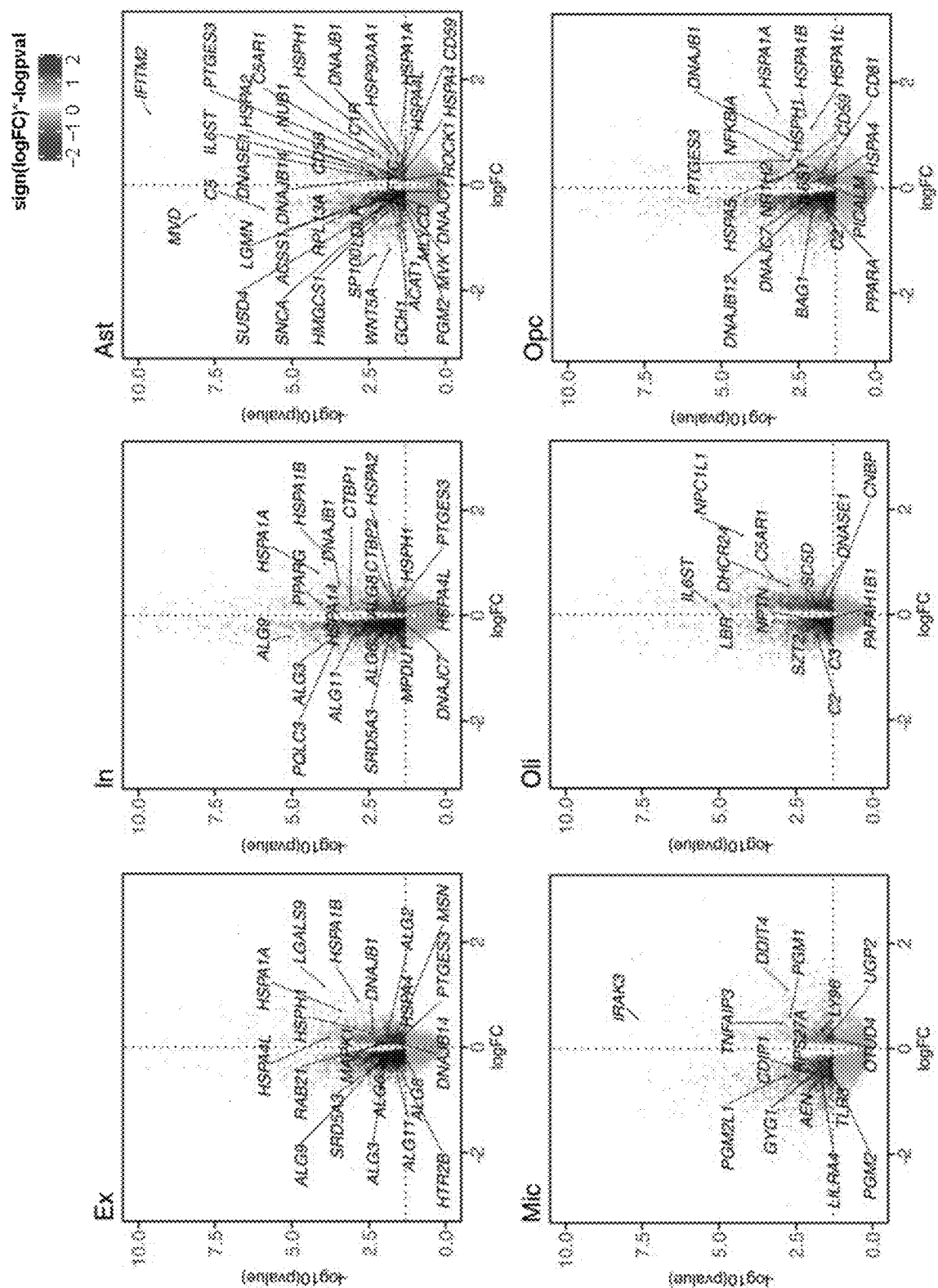

In neurons, APOE4 has previously been observed to increase MAPK1 signaling and downstream APP transcription[40]; in agreement with this, ERK1/2 signaling (e.g. MAPK1) was increased in APOE4 excitatory neurons (FIGS. 6A-6B). APOE4 excitatory neurons also showed increased transcription of endosomal-related transport genes ('regulation of early endosome to late endosome transport', e.g. RAB21, MSN) consistent with reports of increased early endosomes in iPSC-derived APOE4 neurons relative to APOE3[33]. Glycosyltransferase activity ('oligosaccharide-lipid intermediate biosynthetic process', e.g. ALG6, ALG3) was decreased in APOE4 excitatory and inhibitory neurons. Deficient glycosylation of lipids and proteins has been previously linked to neurodegeneration[41], suggesting another avenue by which APOE4 might exert a pathogenic role (FIGS. 6A-6B). Interestingly, APOE4 oligodendrocytes showed decreased neuronal-associated processes, including regulation of synaptic plasticity and axonogenesis ('regulation of long-term neuronal synaptic plasticity' and 'central nervous system projection neuron axonogenesis', e.g. NPTN) (FIGS. 6A-6B).

Among the broadly dysregulated processes, APOE4 was associated with increased chaperone-mediated protein folding in the majority of cell types (e.g. DNAJB14, HSPA1A), indicating widespread cellular stress in APOE4. Multiple studies have associated altered amyloid processing and DNA damage with APOE4, APOE expression, and AD[42-46]. Consistent with this, APOE4 caused widespread alterations to amyloid metabolism genes in astrocytes, excitatory neurons, and OPCs ('regulation of amyloid-beta clearance', e.g. PICALM, ROCK1) (FIGS. 6A-6B). APOE4 microglia and OPCs both exhibited elevated levels of DNA damage response and DNA-damage-associated cell death (e.g. DDIT4), suggesting APOE4 may cause or increase the sensitivity of specific cell types to DNA damage (FIGS. 6A-6B).

APOE4 also altered energy metabolism across multiple cell types. APOE4-mediated metabolic alterations included increased cholesterol biosynthesis in oligodendrocytes (e.g. DHCR24, LBR), white fat cell-related genes in inhibitory neurons (e.g. PPARG, CTBP1), negative regulation of lipid storage in OPCs (e.g. NR1H2) (FIGS. 6A-6B), altered expression of glycogen metabolism genes in microglia and astrocytes ('glycogen biosynthetic process', e.g. UGP2, PGM1) (FIGS. 6A-6B), and decreased acetyl-CoA metabolism gene expression in astrocytes (e.g. ACAT1, ACSS1) (FIGS. 6A-6B). This demonstrates that APOE4 has a pronounced effect on metabolism, implying that dysregulation of energy production, transport, or utilization could be a central pathogenic mechanism of APOE4.

Collectively, these APOE4 effects in the post-mortem human brain align with established signatures and hallmarks of APOE4. This analysis provides a comprehensive molecular atlas elucidating the effects of APOE4 in the aged human brain, which, as we will demonstrate, facilitates the discovery of new biological mechanisms and therapeutic opportunities for AD.

APOE4 Alters Lipid Homeostasis in Multiple Cell Types in the Human PFC

Figure 1B:
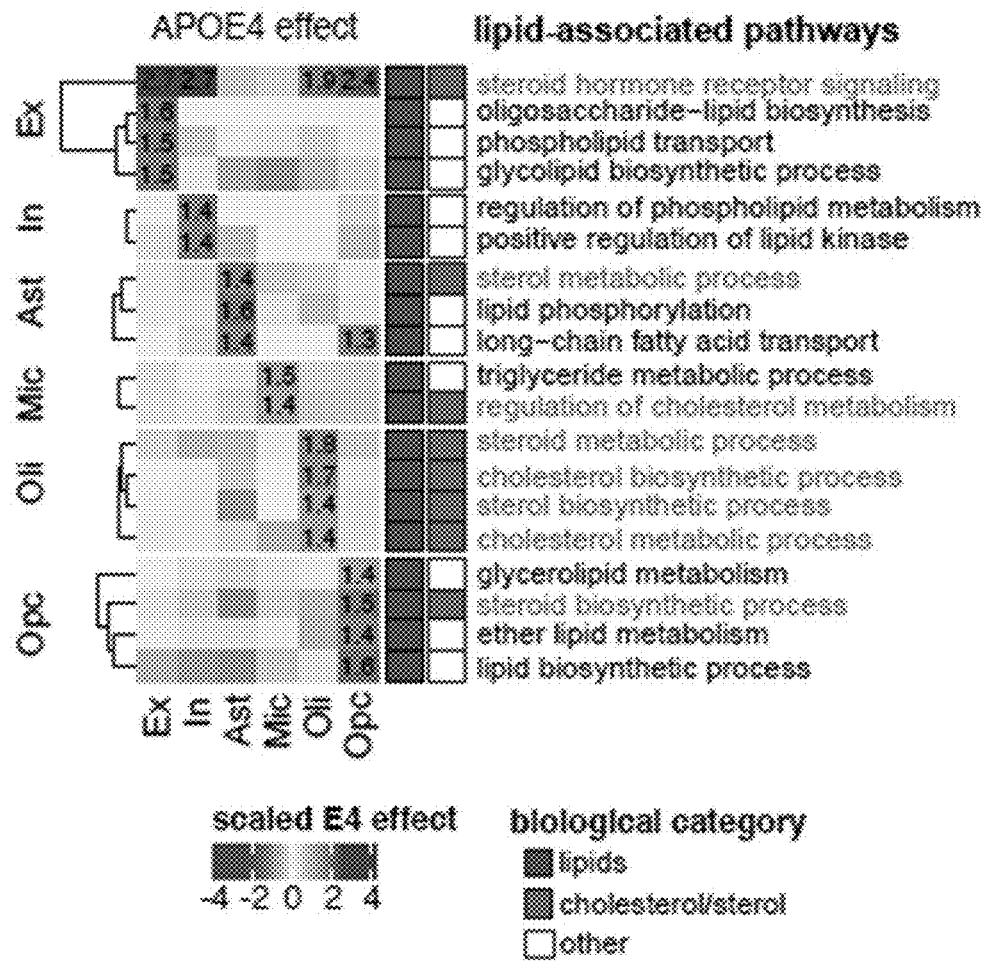
Figure 1C:
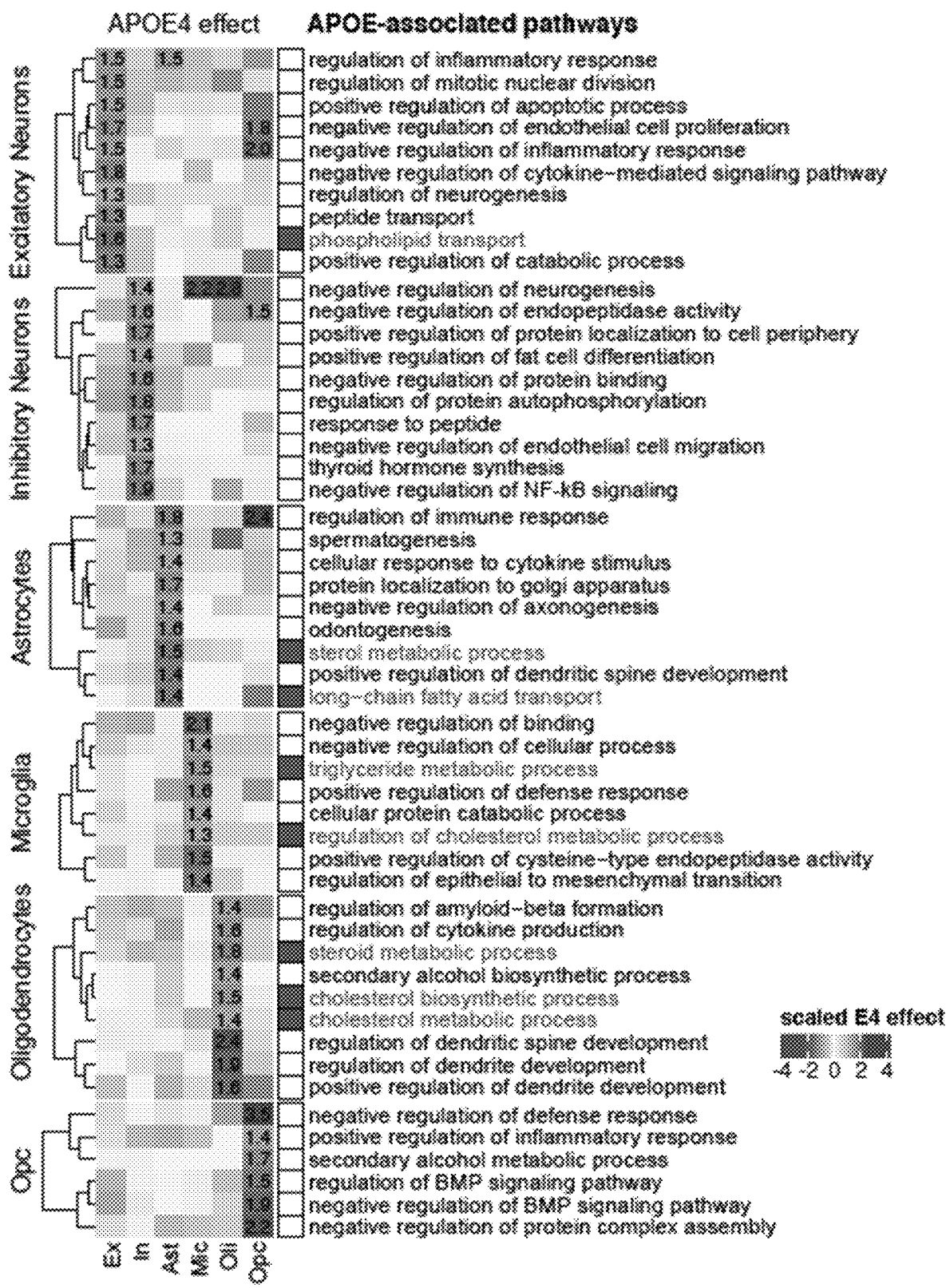
Figure 7A:
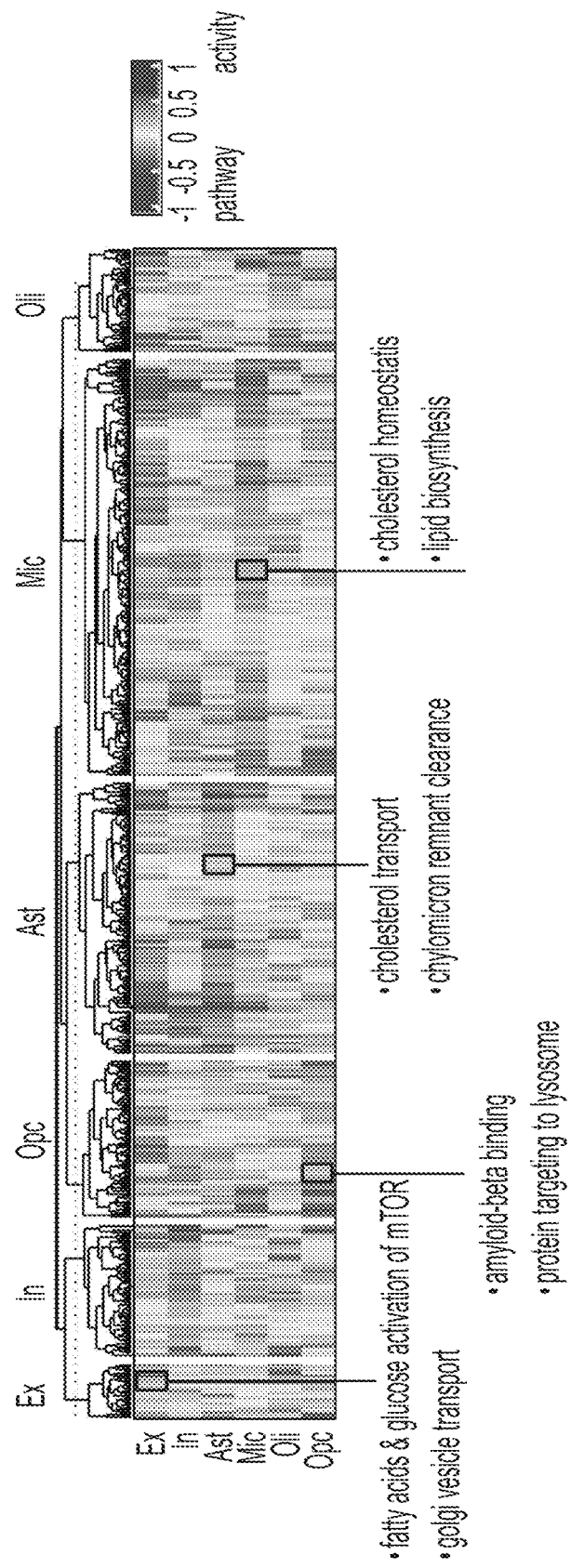
FIGS. 7A-7J: APOE-associates pathway activity and lipid associations.
Figure 7C:
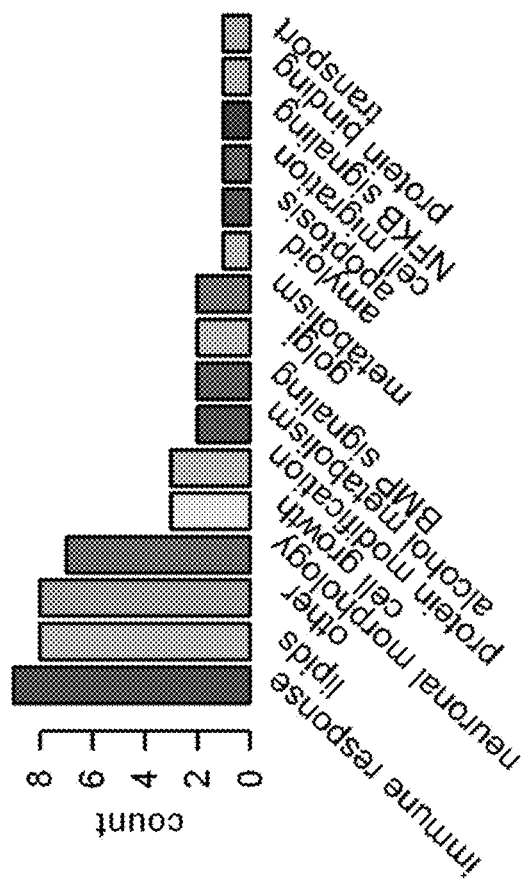
Figure 7B:
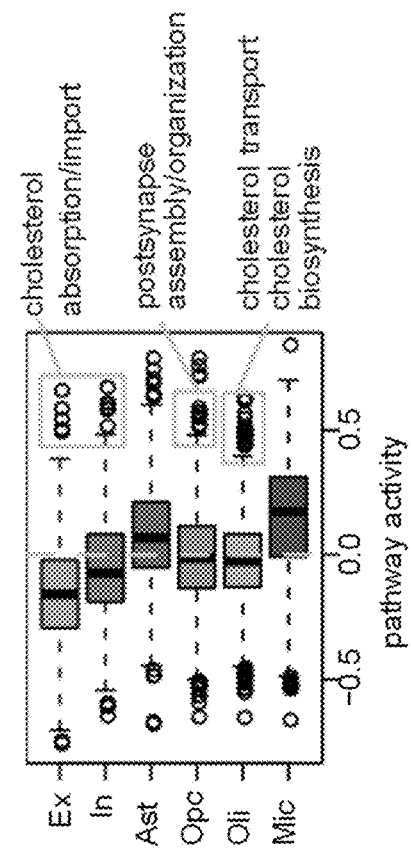

Next, molecular pathways known to directly involve APOE and/or APOE receptor genes (N=556) were specifically analyzed (Methods). A subset of APOE-associated pathways was active across all major cell types (FIGS. 7A-7B). Some APOE-related pathways exhibited high cell-type-specific activity, such as cholesterol transport in oligodendrocytes and synapse processes in OPCs (FIG. 7B). To facilitate interpretation, perturbed pathways of the largest APOE4 effect size were grouped into 16 major themes. These groups include amyloid processing, BMP and NFκB signaling, cell growth, golgi-associated processes, neuronal morphology, immune response, and lipids (FIG. 1C; FIG. 7C). Lipid homeostasis constituted one of the most frequently APOE4-dysregulated functional categories among APOE-associated processes (FIG. 7C). Gene expression patterns associated with specific lipid processes, such as fatty acid and phospholipid transport, triacylglycerol metabolism, and cholesterol/sterol homeostasis, were recurrently perturbed in APOE4 oligodendrocytes, astrocytes, microglia, and neurons (FIG. 1C).

Figure 7E:
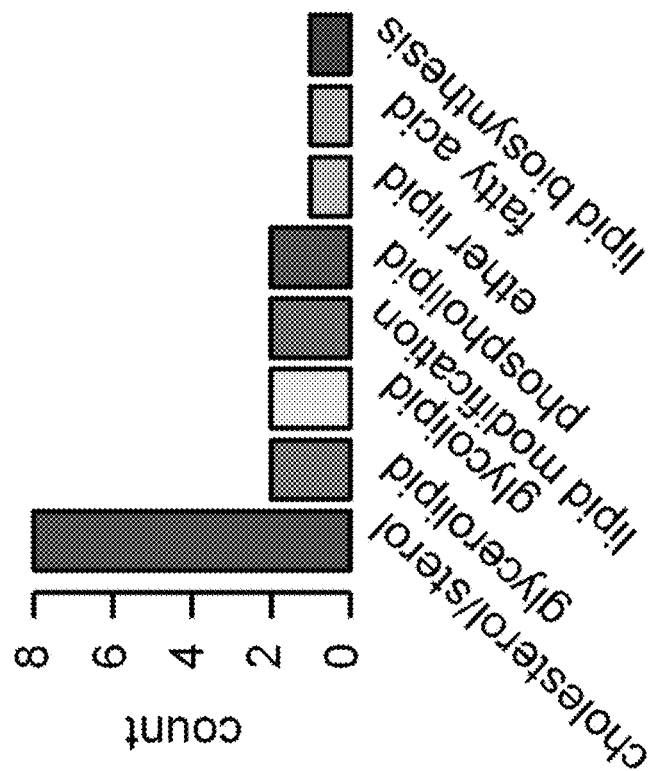

To further investigate APOE4's effect on lipid homeostasis in the human brain additional analysis of a subset of lipid-related pathways was performed (Methods; FIG. 1B). This analysis revealed 19 dysregulated lipid-associated pathways across all major cell types with significant alterations in cholesterol, phospholipid, glycolipid, fatty acid, and triglyceride metabolism (FIG. 1B; FIG. 7E). Consistent with previous reports, decreased fatty acid transport and sterol metabolism gene expression was observed in APOE4 astrocytes[47,33]. While APOE4 neurons, astrocytes, and OPCs were characterized predominantly by down-regulated lipid processes, APOE4 microglia and oligodendrocytes showed up-regulated lipid processes relative to APOE3, including triacylglycerol metabolism (microglia) and cholesterol metabolism (oligodendrocytes and microglia) (FIG. 1B). Together these data show lipid-associated pathways are highly perturbed in APOE4, suggesting that lipid dysregulation in specific cell types may play a key role in APOE4-mediated pathogenesis.

Figure 1D:
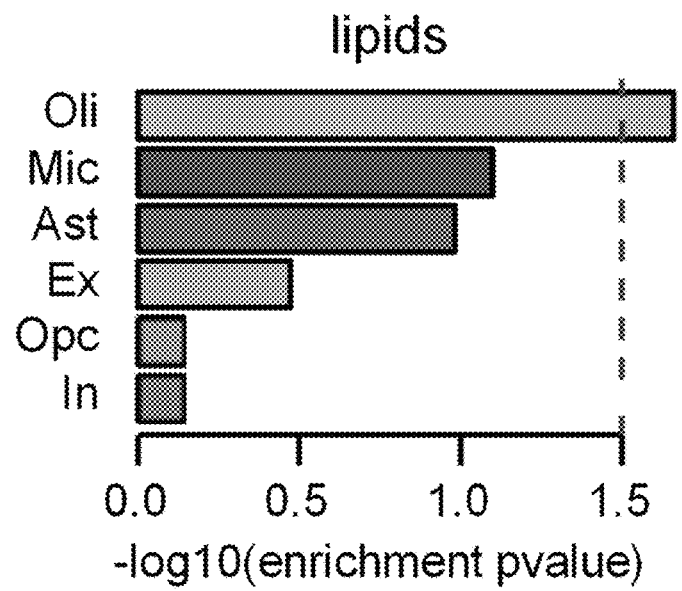
Figure 1E:
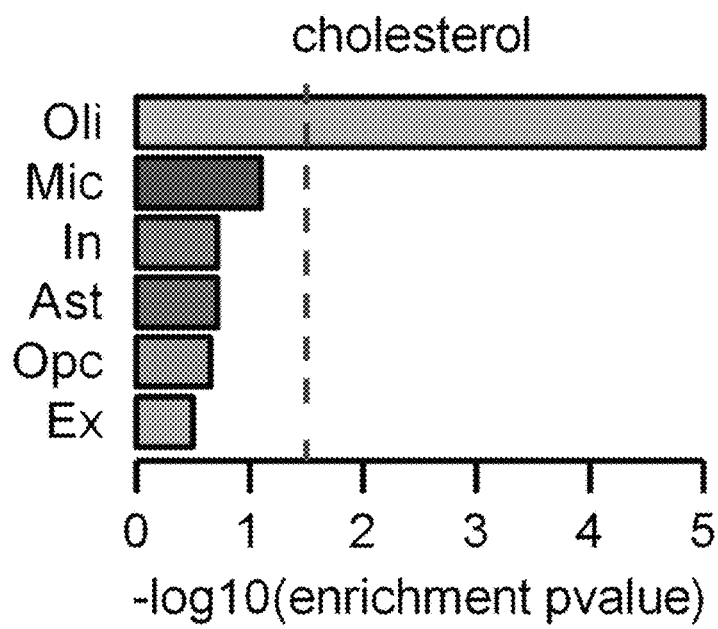
Figure 7D:
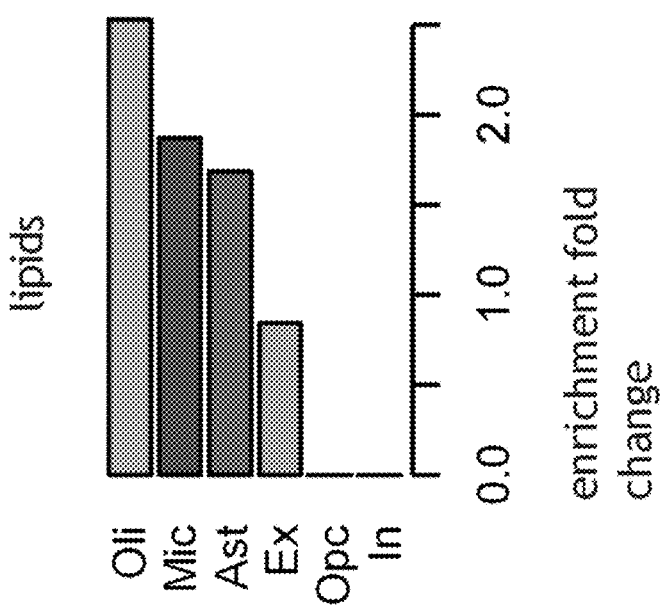
Figures 7F, 7G:
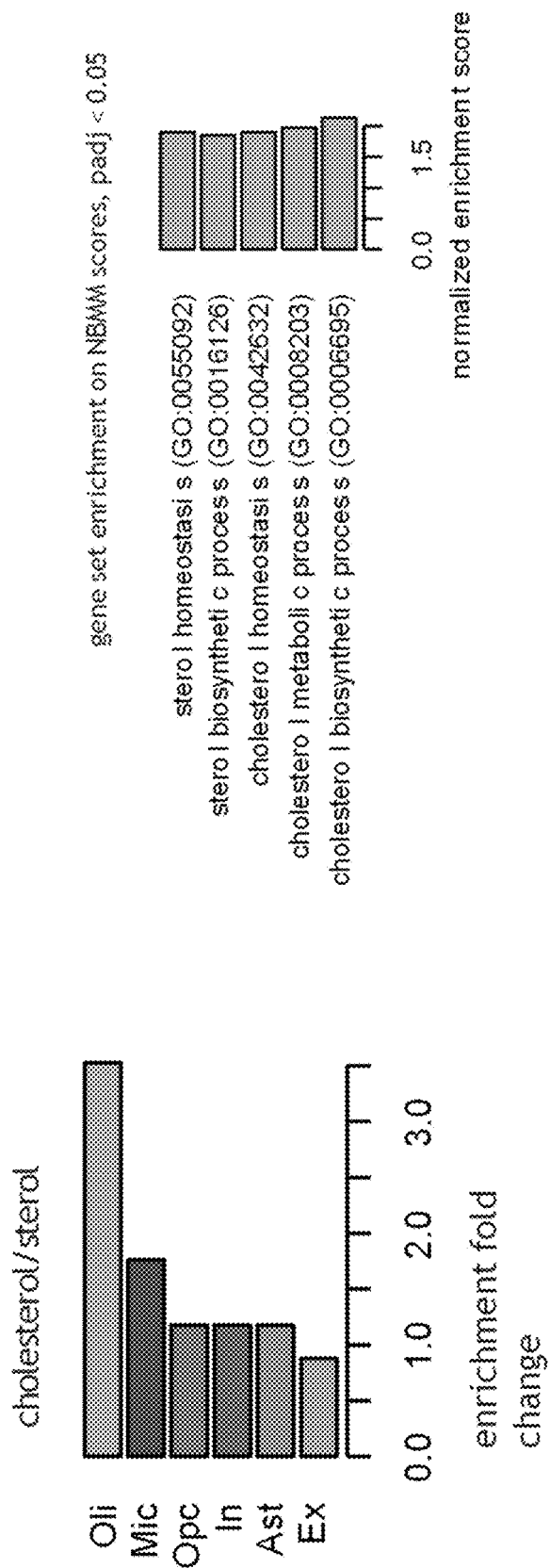
Figure 7I:
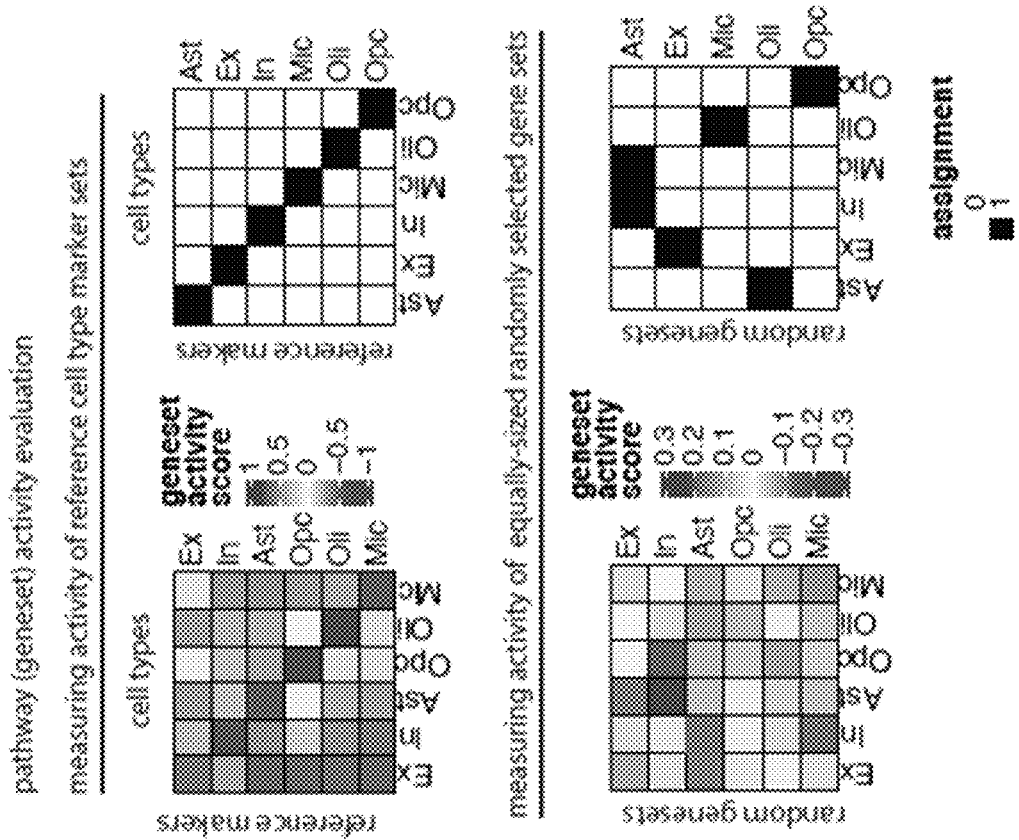
Figure 7H:
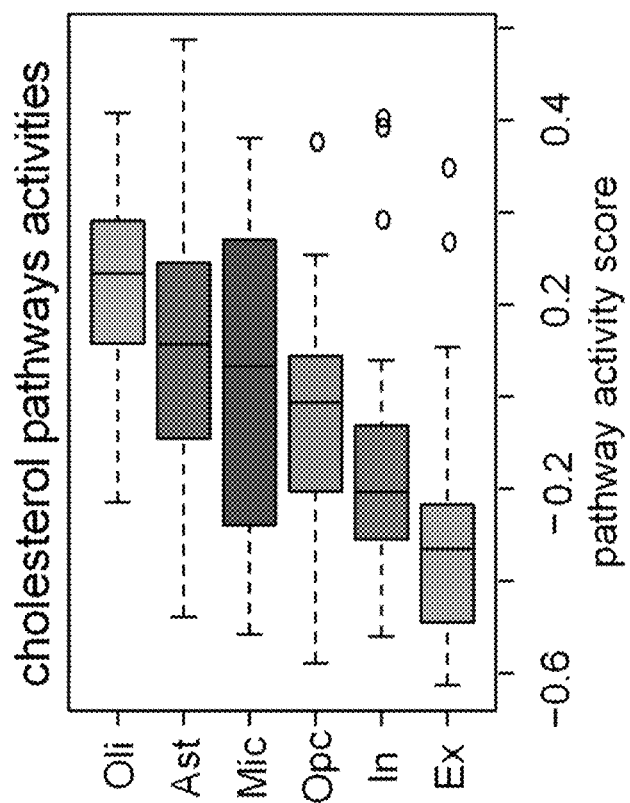
Figure 7J:
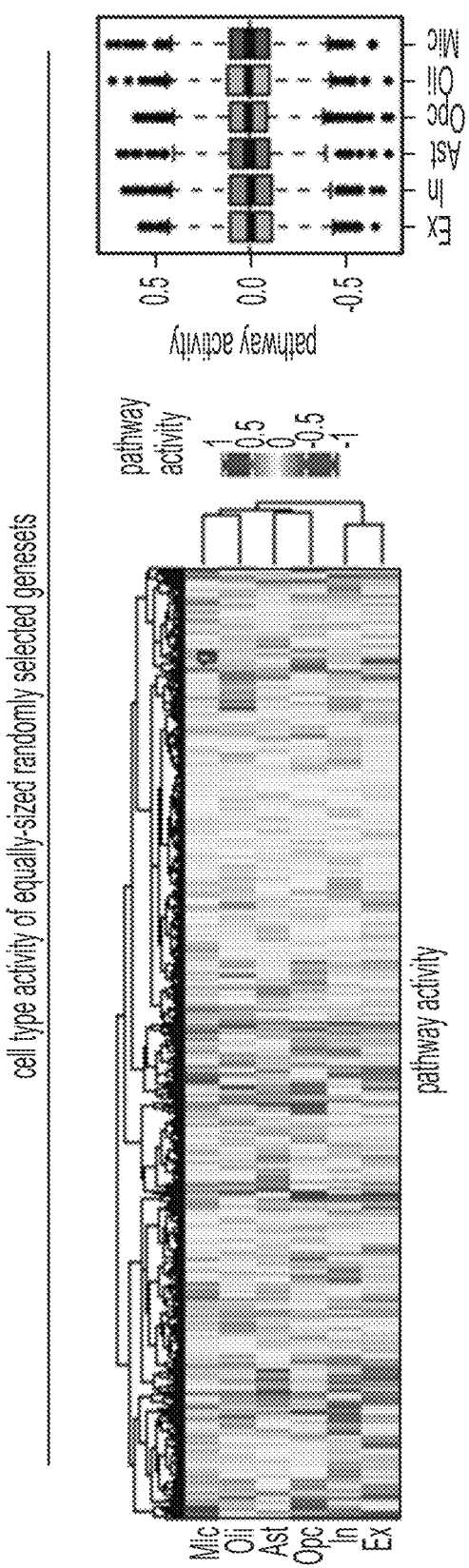

Oligodendrocytes were the cell type with the most frequent alterations of lipid processes in APOE4. Specifically, lipid-associated terms were significantly enriched among the top pathways associated with APOE4 in oligodendrocytes (fold enrichment=2.5, p-value=0.02, hypergeometric test) (FIG. 1D; FIG. 7D). Cholesterol/sterol was the most frequently dysregulated lipid-class across all major cell types (FIG. 7E), and it was particularly enriched among perturbed lipid pathways in oligodendrocytes (p-value<0.05, hypergeometric test) (fold change=3.5, p-value=1e-05) (FIG. 1E; FIG. 7F). Cholesterol dysregulation was confirmed in APOE4 oligodendrocytes by differential expression (negative binomial mixed model) and gene set enrichment analysis as an orthogonal approach (FIG. 7G). Overall, cholesterol-associated pathways were also most active in oligodendrocytes compared to other cell types, in line with oligodendrocytes' role in myelination (FIG. 7H).

APOE4 Increases Cholesterol Accumulation in Oligodendrocytes

Figure 2A:
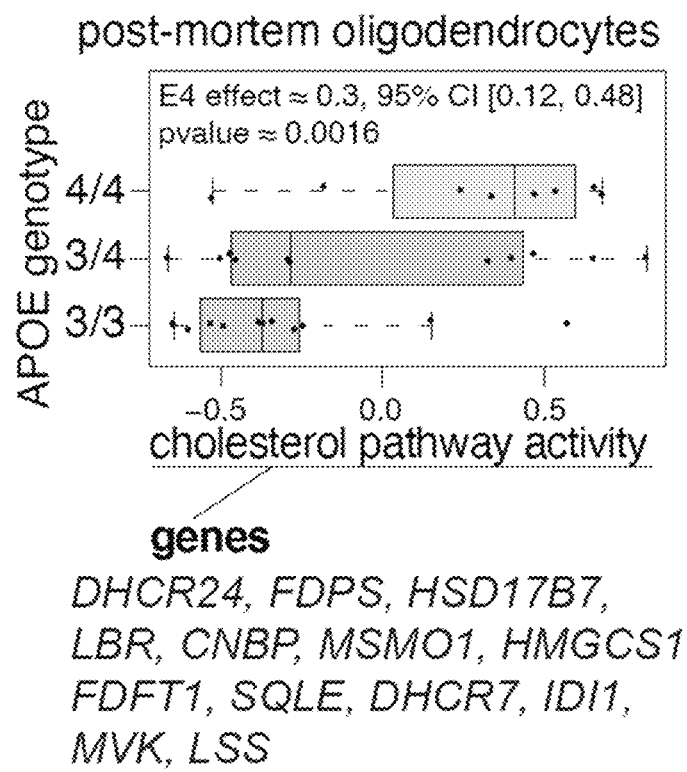
FIGS. 2A-2I: APOE4 perturbs cholesterol homeostasis in oligodendrocytes.
Figure 2B:
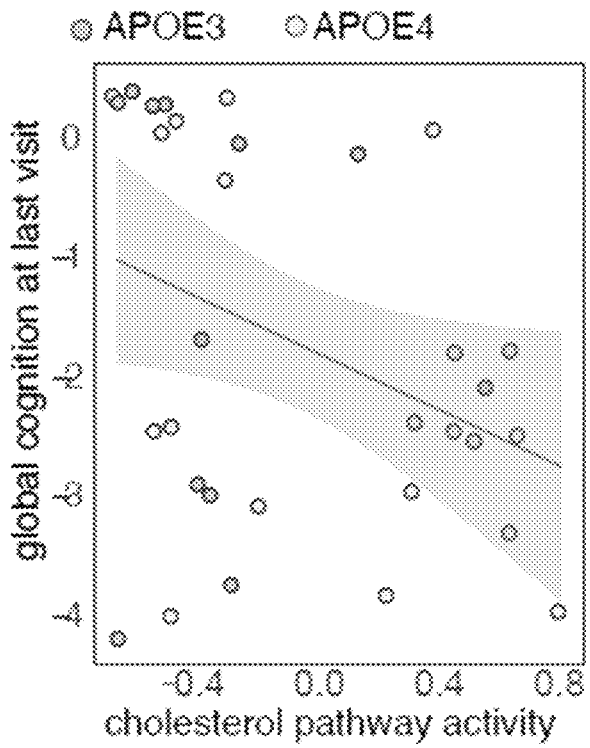

APOE4 has a dose-dependent effect on the probability of developing AD. Similarly, APOE4 was associated with significantly increased (p-value=0.0016) cholesterol pathway activity in oligodendrocytes in a dose-dependent manner, suggesting that APOE4 modulation of these pathways may influence the risk of developing AD (FIG. 2A). To further assess the functional relationship between altered cholesterol homeostasis in APOE4 oligodendrocytes and cognitive outcomes in AD, it was asked whether there was a significant correlation between the collective activity of cholesterol homeostasis genes and end-stage global cognition (cogn_global_lv, as reported by ROSMAP). Interestingly, increased transcriptional activity of cholesterol genes in oligodendrocytes correlated with reduced end-stage cognition (correlation≈−0.36, 95% confidence interval [−0.63, −0.01], p-value≈0.0433), suggesting cholesterol dysregulation in oligodendrocytes may impact cognition (FIG. 2B). Collectively, this data demonstrates that APOE4 is associated with widespread dysregulation of lipid metabolism in human brain cells and profound cholesterol dyshomeostasis in oligodendrocytes, which significantly correlates with end-stage cognition in humans.

Figure 2C:
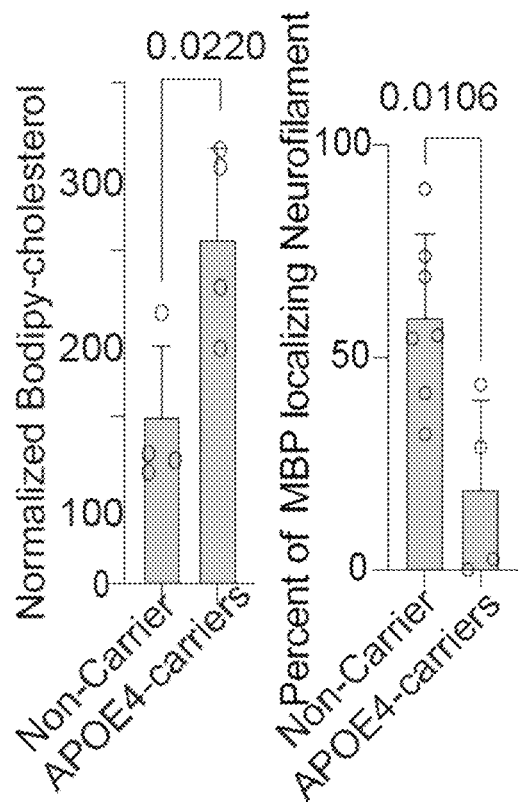
Figure 2D:
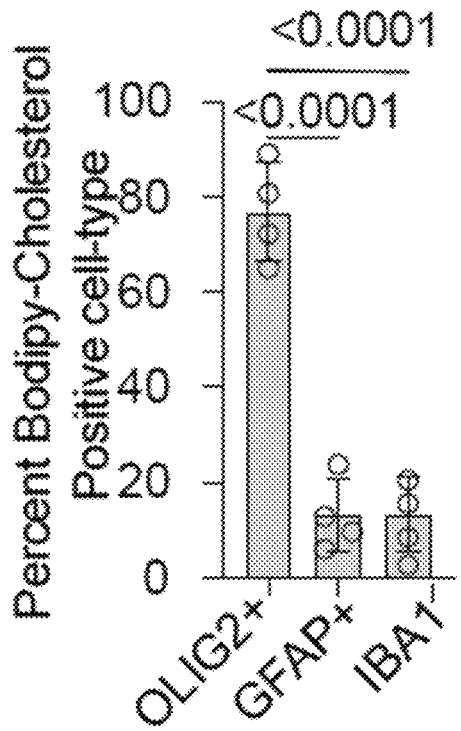

To further investigate the effects of APOE4-mediated cholesterol dysregulation in the human brain, post-mortem prefrontal cortex samples from APOE4 carriers (APOE3/4) (n=4) and non-carriers (APOE3/3) (n=7) were stained with the fluorescent dye bodipy-cholesterol. In APOE3/3 PFC tissue, bodipy-cholesterol staining was most intense along neurofilament tracts, where it formed ribbon-like staining patterns adjacent to neurofilament and Mbp staining (FIG. 2C). In the white matter tracts from APOE3 PFCs, 59.34% of bodipy-cholesterol was within 1 μm of neurofilament staining. Across multiple PFC sections, APOE4-carriers exhibited a significantly (p=0.0220) higher mean intensity of bodipy-cholesterol staining, indicating an increase in overall cholesterol; however, bodipy-cholesterol staining and localization in PFC white matter tracts differed between APOE3- and APOE4-carriers (FIG. 2C). In particular, in APOE4 carriers, the localization bodipy-cholesterol along neurofilaments was significantly (p=0.0106) decreased from 57.47% to only 18.76% of the total bodipy-cholesterol signal (FIG. 2C). Instead, in APOE4-carriers, bodipy-cholesterol staining appeared most prominently in intracellular accumulations around distinct nuclei, suggesting that specific cell types in APOE4-carriers could be aberrantly accumulating cholesterol (FIG. 2C). This single-cell transcriptomic data suggested that cholesterol homeostasis was prominently dysregulated in APOE4 oligodendrocytes and to a lesser extent in microglia and astrocytes. To determine whether these were the same cell-types in which bodipy-cholesterol was accumulating PFC white matter from APOE4-carriers was co-stained with bodipy-cholesterol and cell-type-specific markers (OLIG2 for oligodendrocytes, GFAP for astrocytes, and IBA1 for microglia). IBA1-positive microglia and GFAP-positive astrocytes exhibited minimal (<15% of cells) bodipy-cholesterol accumulation (FIG. 2D). In contrast, the area surrounding (within 2 μm radius) OLIG2-positive nuclei exhibited significantly (p<0.0001) more bodipy-cholesterol staining with 76.8% of Olig2-positive nuclei surrounded by intense bodipy-cholesterol, suggesting that cholesterol may aberrantly accumulate in APOE4 oligodendrocytes (FIG. 2D).

Figure 8A:
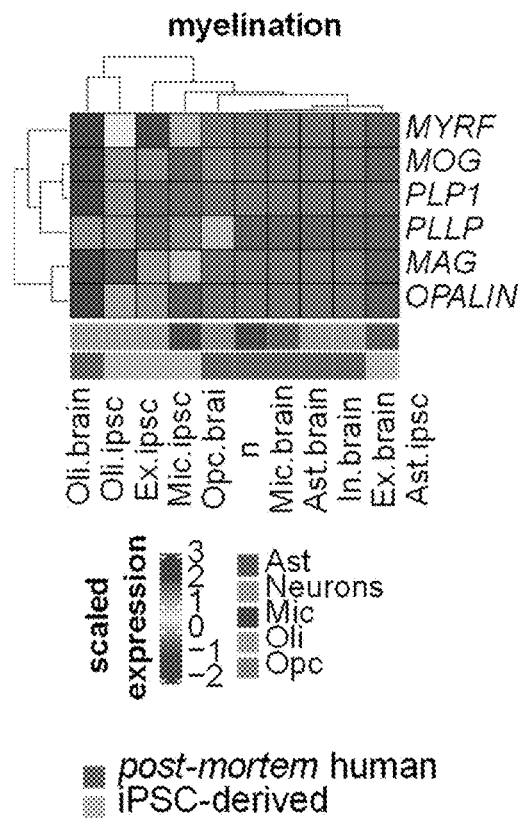
FIGS. 8A-8L: Comparison of post-mortem Oligodendrocytes and iPSC-derived oligodendroglia.
Figure 8B:
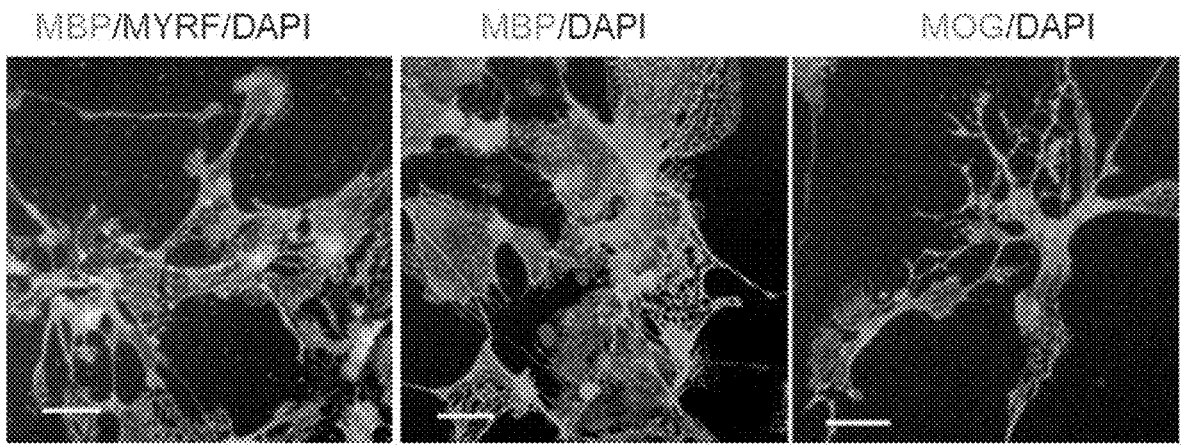
Figure 8C:
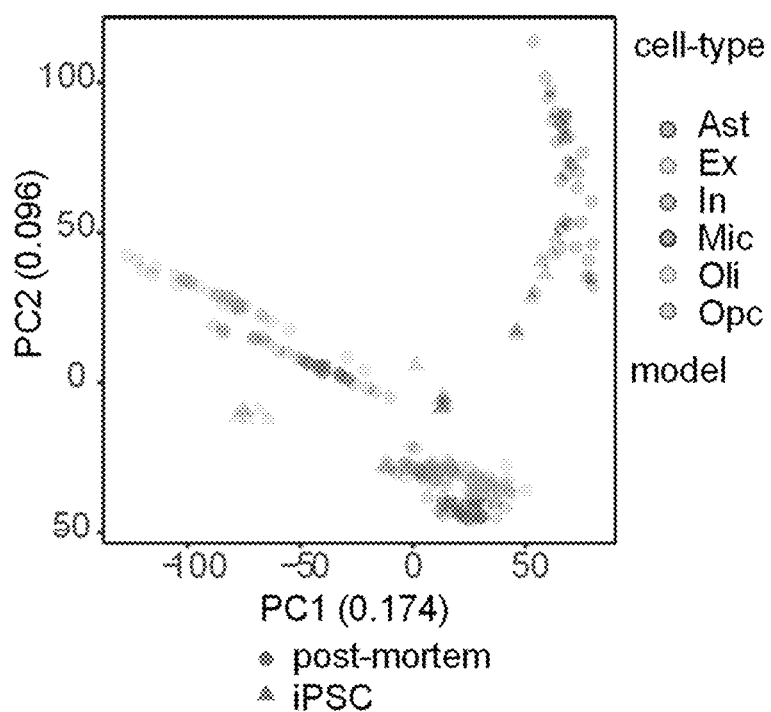
Figure 8D:
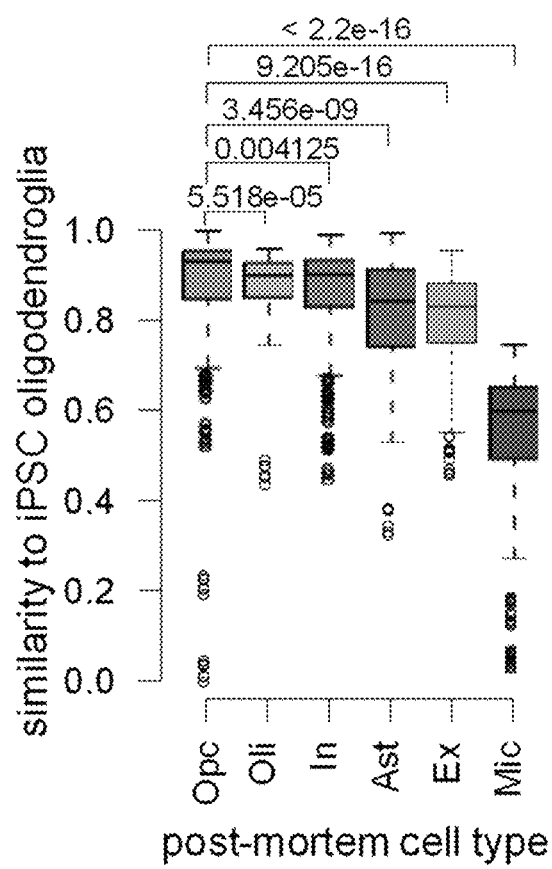
Figure 8E:
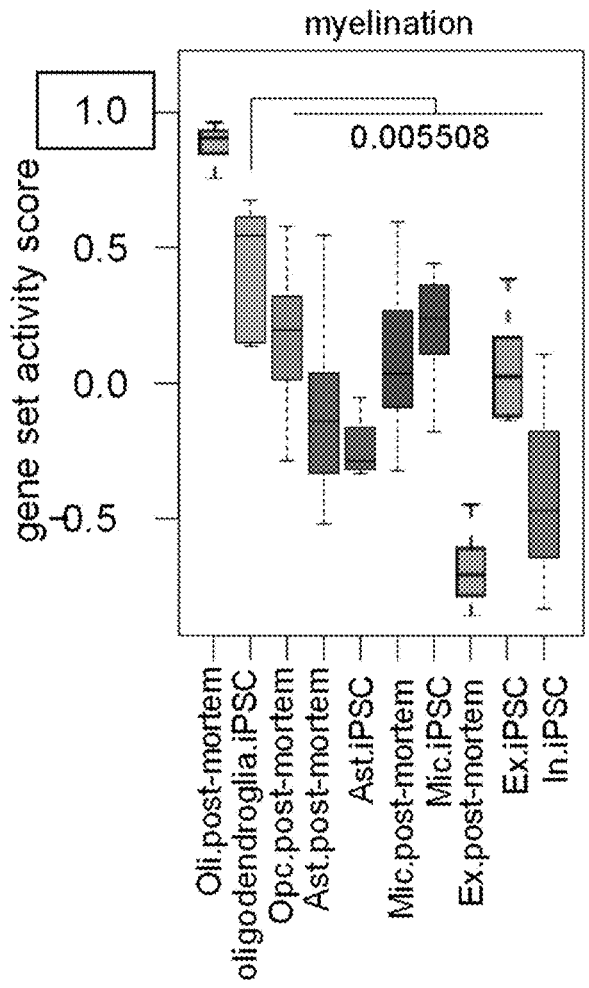
Figure 8F:
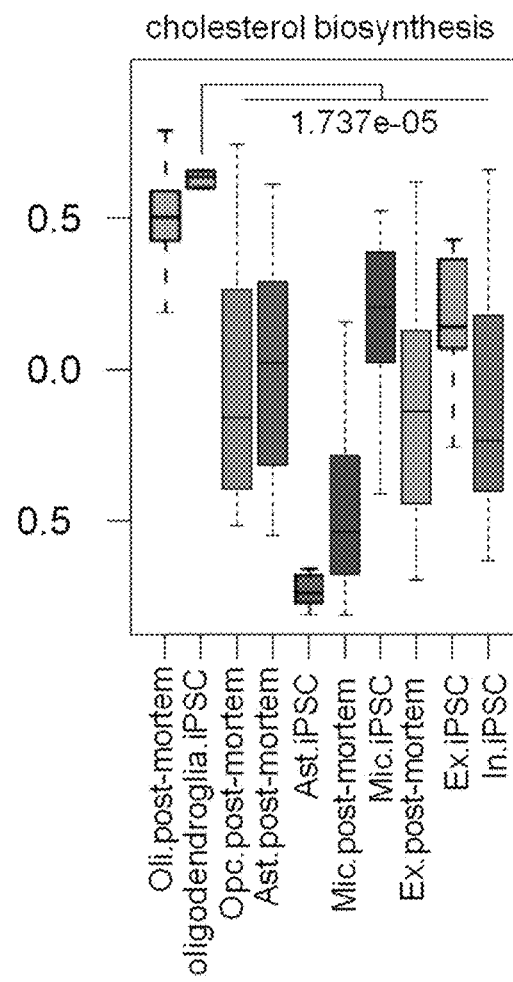
Figure 8G:
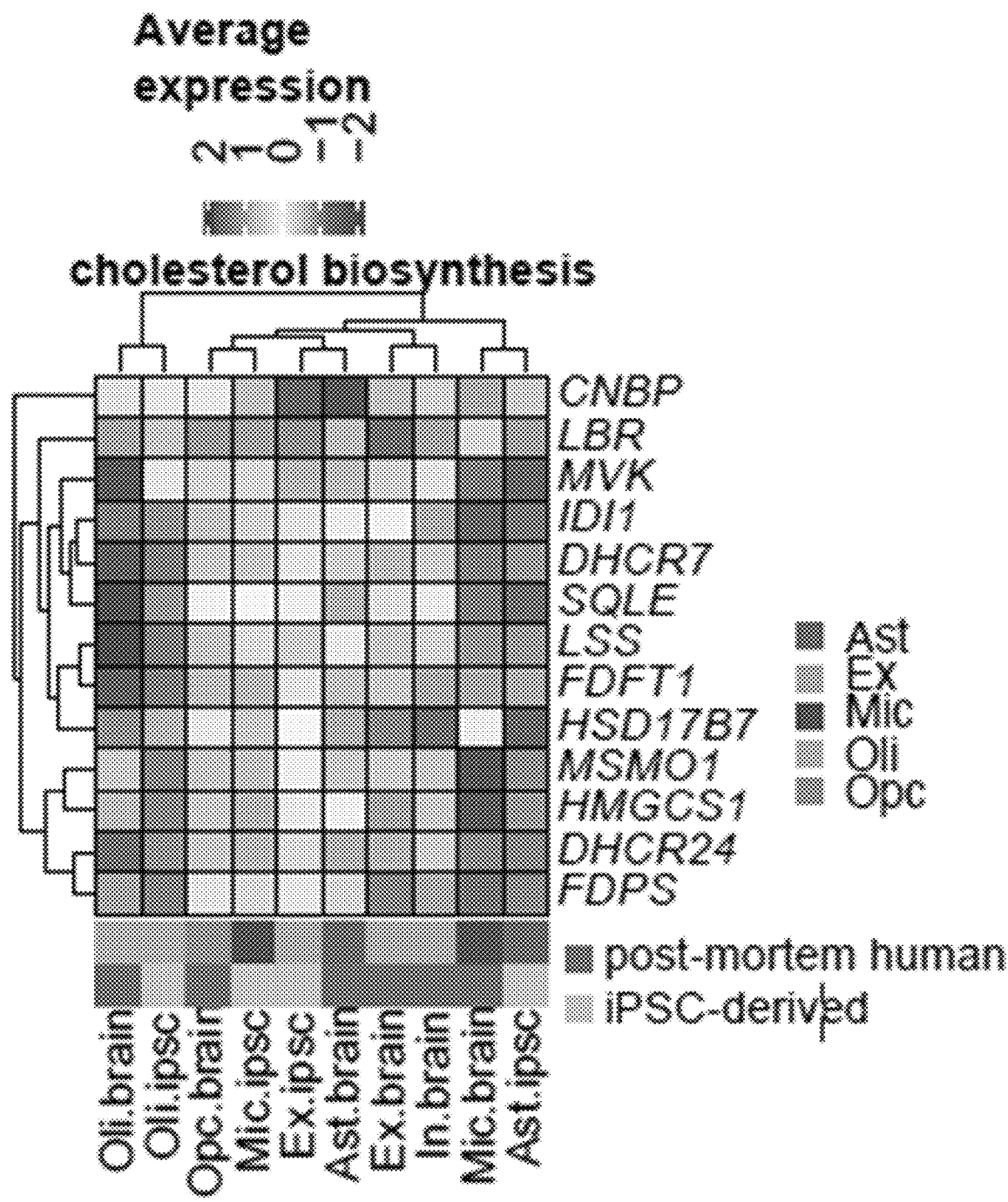
Figure 8H:
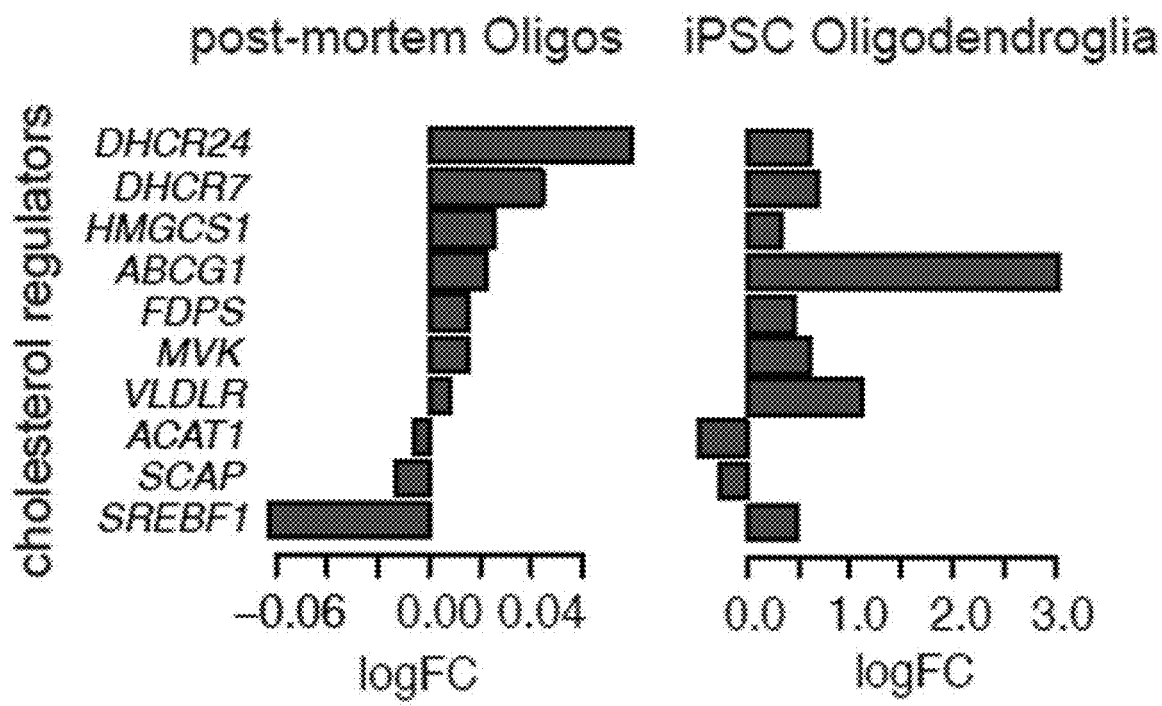
Figure 8I:
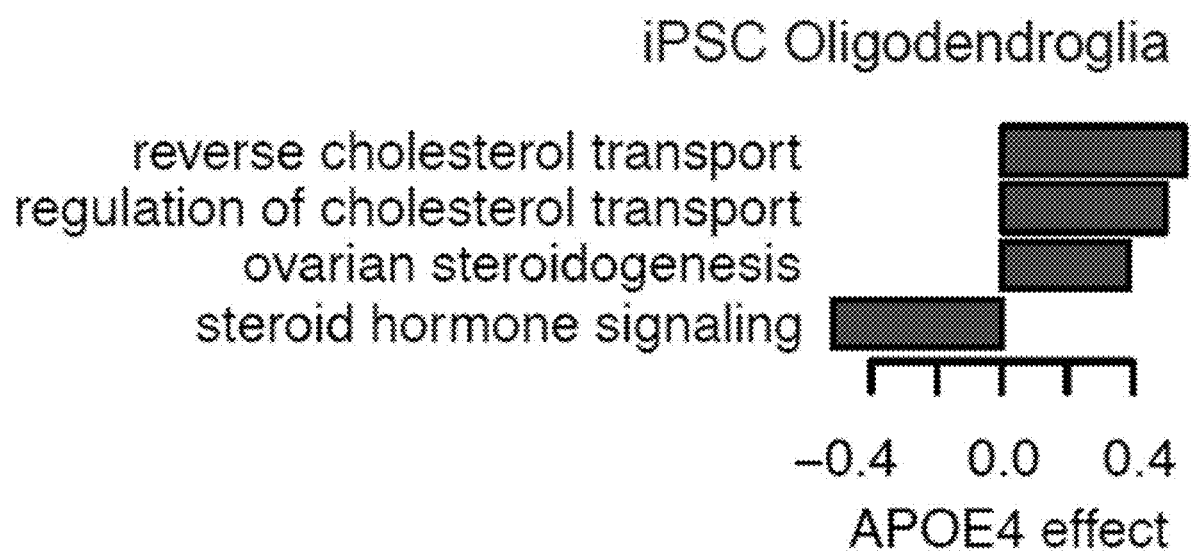

To further determine whether cholesterol accumulation in oligodendrocytes was a direct effect of APOE4, sets of APOE3/3 and APOE4/4 isogenic oligodendroglia differentiated from human CRISPR-edited induced pluripotent stem cells (iPSC) were used[48,49]. Similar to human post-mortem oligodendrocytes, iPSC-derived oligodendroglia expressed mRNAs and proteins specific to oligodendrocytes, including MOG, MBP, PLP1, and MYRF (FIGS. 8A-8B). Principal component analysis confirmed that iPSC-derived oligodendroglia exhibited a high degree of transcriptional similarity to in vivo human oligodendrocytes (FIGS. 8C-8D), including selective upregulation of myelin-associated pathways relative to other cell-types (FIG. 8E). Similar to human post-mortem oligodendrocytes, the expression of cholesterol-associated genes was highly enriched in iPSC-derived oligodendroglia relative to other cell types (FIGS. 8F-8G). In line with the post-mortem data, APOE4 significantly altered numerous cholesterol regulatory genes including DCHR25, DHCR7, HMGCS1, ABCG1, FDPS, MVK, VLVLR, ACAT1, SCAP, and SREBF1, and pathways in iPSC-derived oligodendroglia, compared to isogenic APOE3 oligodendroglia (FIGS. 8H-8I), suggesting iPSC-derived oligodendroglia are a reliable proxy for investigating the effect of APOE4 on human oligodendrocytes.

Figure 2E:
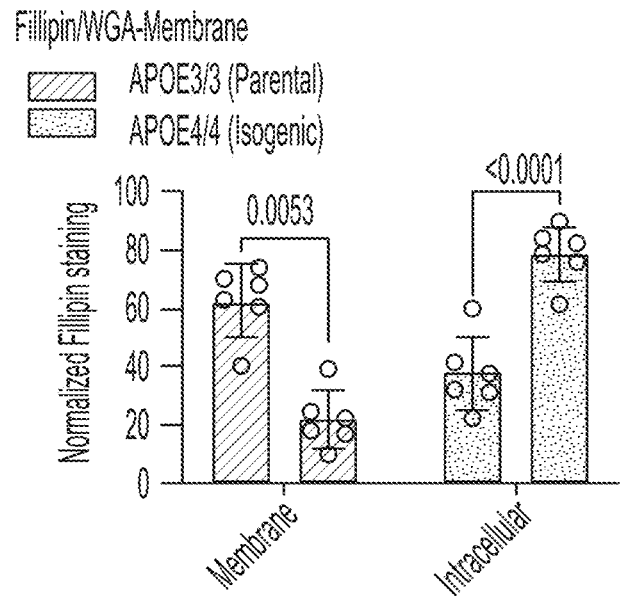
Figure 2F:
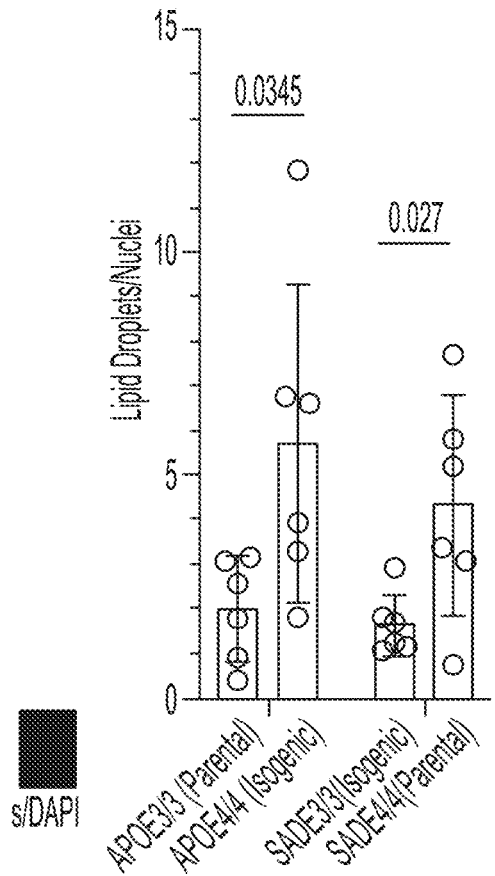

To further investigate APOE4-mediated cholesterol dysregulation, the cholesterol dye filipin was first used to stain isogenic pairs of APOE oligodendroglia and determine the subcellular localization of cholesterol. In APOE3 oligodendroglia, the majority (62.547%+/−12.019) of filipin staining accumulated around the membrane, co-localizing with WGA-membrane stain (FIG. 2E). The remaining filipin signal (37.335%+/−12.675) accumulated intracellularly in APOE3 oligodendroglia (FIG. 2E). In contrast, isogenic APOE4 oligodendroglia exhibited the opposite staining pattern, with significantly increased intracellular (p<0.0001) and decreased membrane (p=0.0053) staining compared to APOE3 oligodendroglia. In APOE4 oligodendroglia 21.702%+/−9.7 of filipin staining localized to the membrane and the majority (78.581%+/−9.561) accumulated intracellularly within APOE4 oligodendroglia (FIG. 2E). The number of lipid droplets was quantified using bodipy staining for two different isogenic sets of oligodendroglia. Compared to their isogenic control APOE3 oligodendroglia, APOE4 oligodendroglia from two different individuals contained significantly (p=0.0345 and 0.027) more bodipy droplets per cell, suggesting that APOE4 oligodendroglia contain an increased number of lipid droplets (FIG. 2F).

Figure 8J:
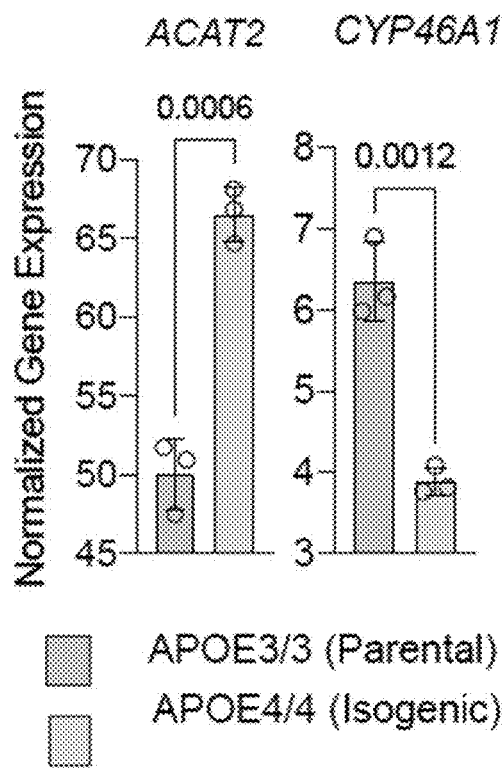
Figure 8K:
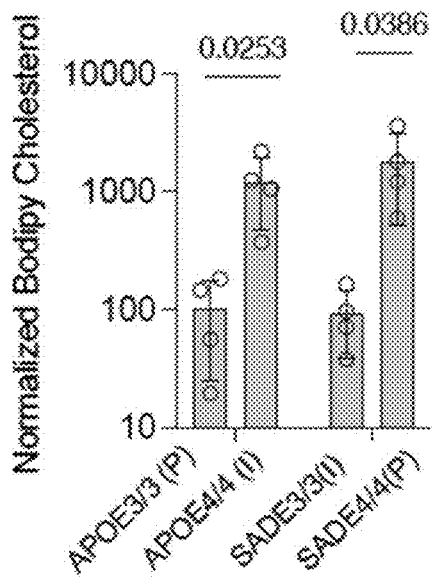
Figure 8L:
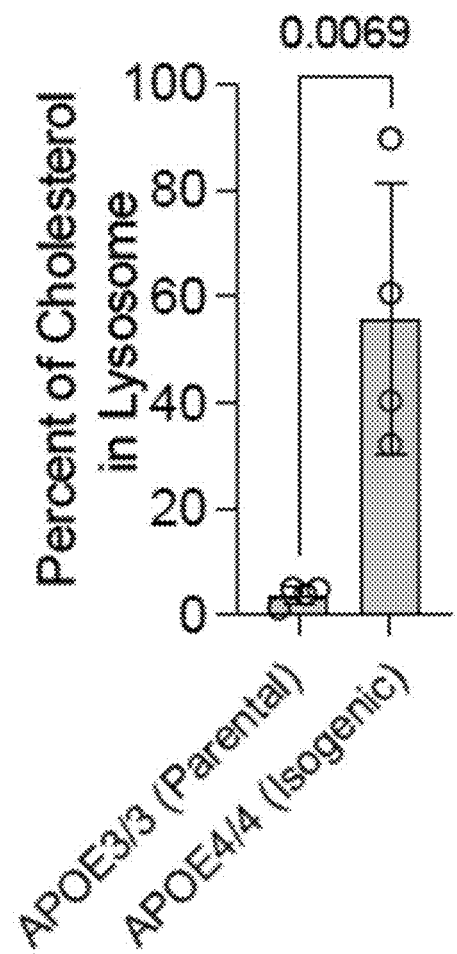

Covalent modifications target cholesterol to specific organelles, with the enzymes ACAT1 and ACAT2 responsible for generating cholesteryl esters that are largely stored in lipid droplets[50]. Consistent with increased levels of intracellular cholesterol in APOE4 oligodendroglia, it was found that ACAT2 expression was significantly (p=0.0006) upregulated in APOE4 oligodendroglia relative to APOE3 (FIG. 8J). CYP46A1 encodes an enzyme primarily responsible for hydroxylating cholesterol in the brain and facilitating its trafficking to the plasma membrane. In agreement with reduced membrane filipin staining (FIG. 2E), APOE4 oligodendroglia expressed significantly (p=0.0012) lower levels of CYP46A1 compared to isogenic APOE3 controls suggesting that cholesterol membrane trafficking in APOE4 oligodendroglia is reduced (FIG. 8J)[51]. To further investigate cholesterol localization, bodipy-cholesterol was added to the cell culture media of live APOE4 and APOE3 oligodendroglia, enabling visualization of cholesterol uptake and intracellular trafficking. Across two different isogenic sets of oligodendroglia generated from different individuals, APOE4 oligodendroglia exhibited significantly elevated (p=0.0253 and 0.0386) bodipy-cholesterol staining, approximately 10-fold higher than their isogenic APOE3 controls. This again suggested that cholesterol aberrantly builds up in APOE4 oligodendroglia (FIG. 8K). Interestingly, approximately 50% of bodipy-cholesterol co-localized with Lysotracker-Red staining, implying a large fraction of cholesterol in APOE4 oligodendroglia is associated with the lysosome (FIG. 8L). Notably, APOE4 oligodendroglia exhibited significantly (p=0.0040) more lysosomal staining (55.66%), consistent with APOE4 mediating inflammatory phenotypes (FIG. 8L)[52].

Figure 2G:
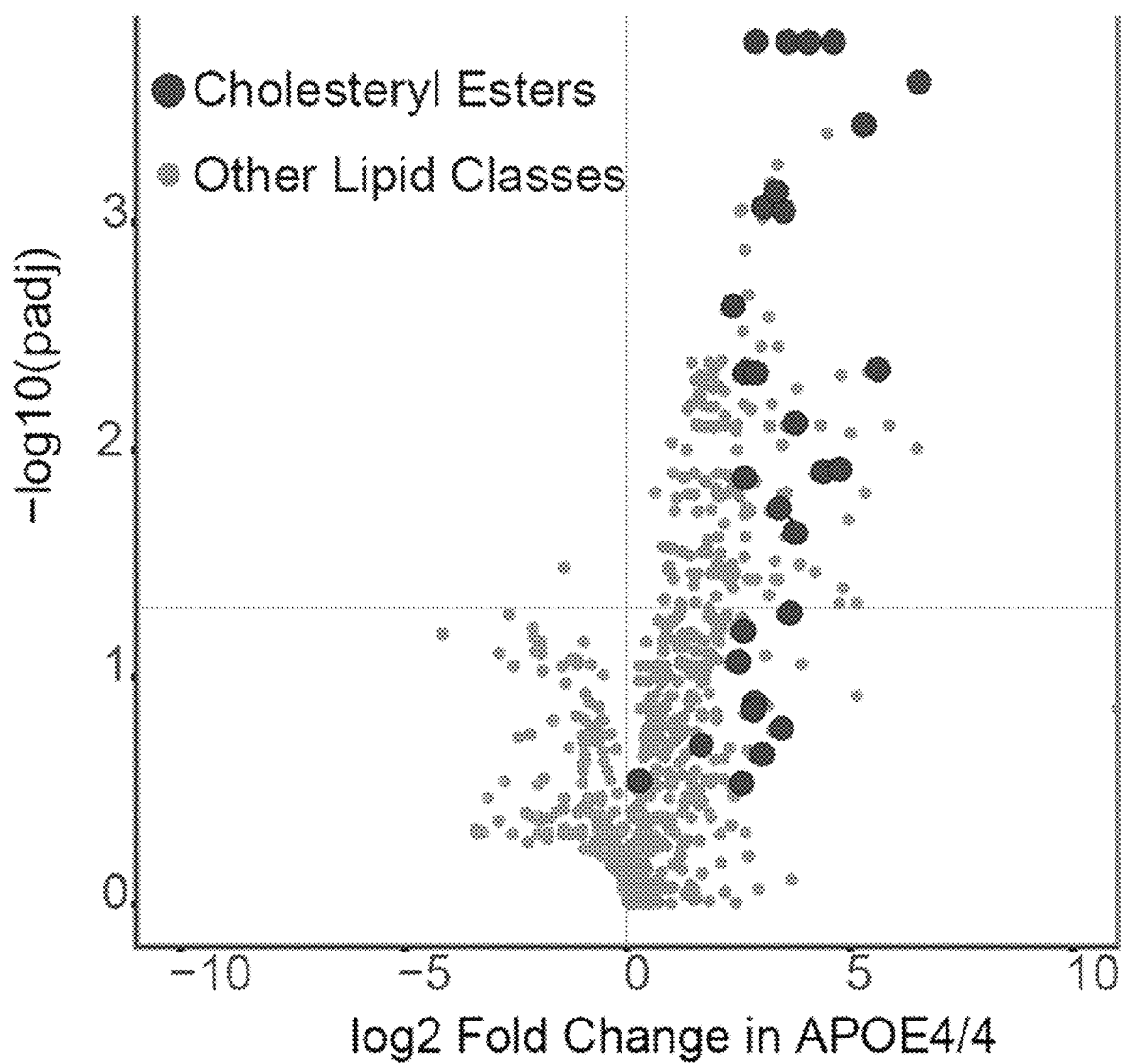
Figure 2H:
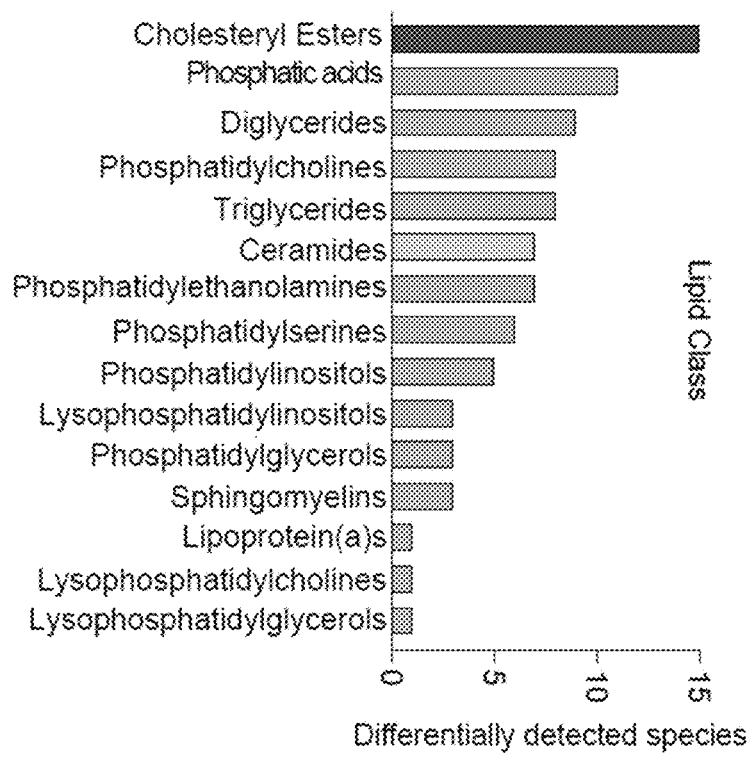
Figure 2I:
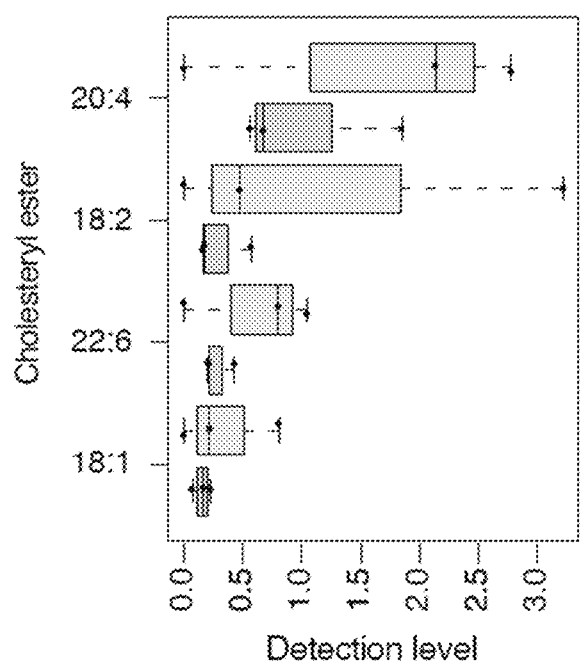

Non-targeted mass-spectrometry-based lipidomic profiling was next performed to determine differences in lipid species composition between APOE3 and APOE4 iPSC-derived oligodendroglia. Consistent with the transcriptional data predicting broad dysregulation of lipid-associated processes in APOE4 cells, 88 differentially (p<0.01) upregulated lipid species were detected in APOE4 oligodendroglia compared to APOE3 controls, with only one species decreased in APOE4 (FIG. 2G; FIG. 5). Each lipid species was next categorized based on class. In agreement with upregulation of the cholesterol esterifying enzyme ACAT2 and increased cholesterol droplets in APOE4 oligodendroglia, it was found that cholesteryl esters were the most altered lipid class, with 15 different species significantly (p<0.01) increased in APOE4 oligodendroglia compared to APOE3 (FIG. 2H) Interestingly, an increase in lysophosphatidylcholine (LPC), a lipid class known to provoke demyelination and subsequent inflammation by integrating into the myelin sheath[53], was also observed. A derivative of LPC, lysophosphatidic acid (LPA), was also highly increased, consistent with APOE4 promoting cellular inflammation[54]. To assess whether the increased abundance of cholesteryl esters reflected changes in the human brain mediated by APOE4, a similar lipidomic profiling was performed of corpus callosum tissue from APOE4-carriers (n=3) compared to non-carriers (n=3). Post-mortem corpus callosum from human APOE4-carriers (APOE4/4, all female) exhibited a trend towards higher levels of all four detected cholesteryl ester species relative to non-carriers (APOE3/3, all female), suggesting that cholesteryl ester species may be elevated in myelinated brain tissue of APOE4 carriers (FIG. 2I). Together, these results demonstrate that APOE4 causes reduced localization of cholesterol in the plasma membrane of iPS-derived, mouse, and human post-mortem oligodendrocytes, and increased abundance of cholesteryl esters, associated with intracellular storage of cholesterol as lipid droplets.

Figure 3A:
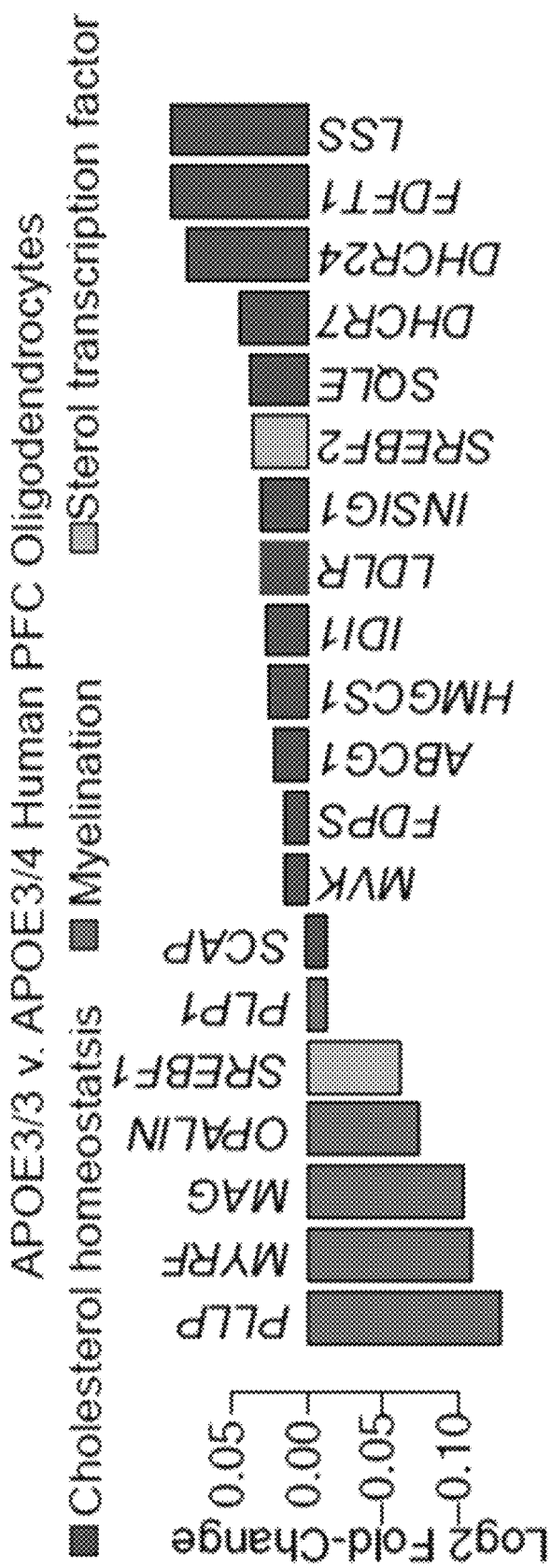
FIGS. 3A-3G: APOE4 leads to impaired myelination.
Figure 3B:
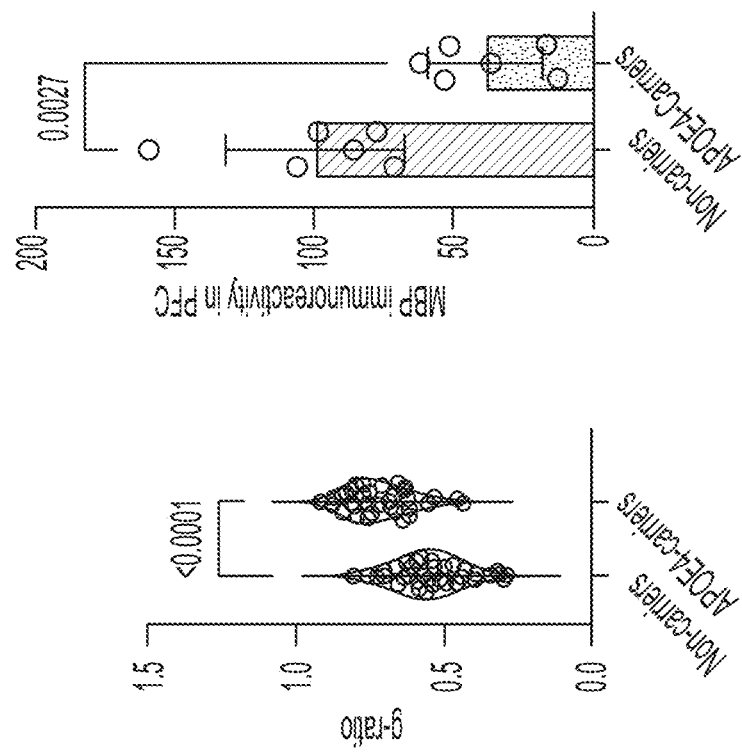
Figure 10A:
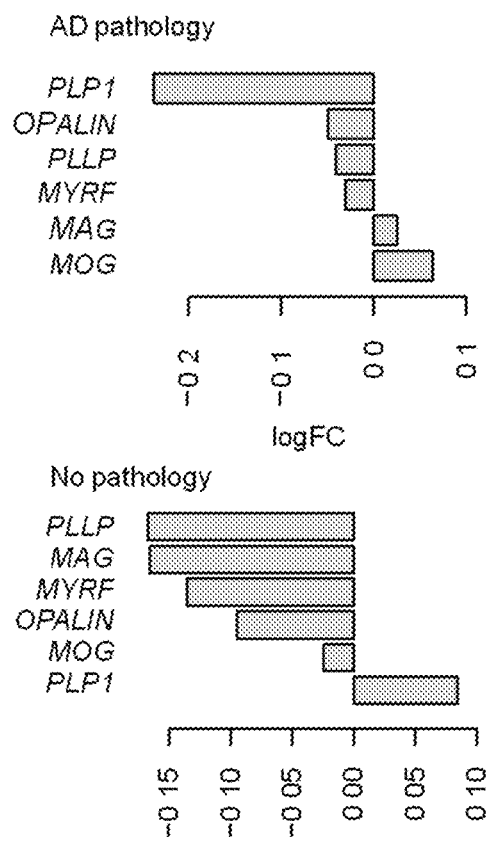
FIG. 10A-10G.

Altered Cholesterol Synthesis in APOE4 Oligodendrocytes is Associated with Reduced Myelination Oligodendrocytes are responsible for generating and maintaining myelin sheaths in the central nervous system. Cholesterol is an essential lipid in myelin, and its bioavailability is a rate-limiting step in the formation and maintenance of myelin sheaths[55]. Therefore, it was reasoned that dysregulated cholesterol localization and homeostasis in APOE4 oligodendrocytes may impair myelination. To test this hypothesis, the relationship between myelin and cholesterol-associated genes in human post-mortem APOE4 oligodendrocytes was first examined using the single-nucleus transcriptomics dataset. Compared to non-carriers, APOE4 post-mortem human oligodendrocytes exhibited a significant downregulation of several myelin-associated genes (including PLLP, MYRF, MAG, OPALIN, and PLP1) when stratified by AD pathology (FIG. 3A; FIG. 10A). Concomitant with decreased myelin gene expression, human post-mortem APOE4 oligodendrocytes exhibited an upregulation of genes associated with cholesterol homeostasis, including MVK, FDPS, ABCG1, IDI1, LDLR, INSIG1, SREBF2, SQLE, DHCR7, DHCR24, FDFT1, and LSS compared to APOE3 oligodendrocytes (FIG. 3A). To examine whether reduced myelin gene expression in APOE4-carriers translated to a reduction of myelin-related proteins, PFC tissue was next immunostained from both APOE genotypes. In PFC white matter regions from APOE3/3-carriers, MBP staining was robustly present and closely associated with neurofilament-positive axons. In contrast, PFC white matter regions from APOE4-carriers exhibited significantly (p=0.0027) decreased MBP staining compared to non-carriers, with fewer MBP regions surrounding neurofilament-positive axons. This suggests that myelin levels may be reduced in APOE4-carriers in vivo (FIG. 3B).

Figure 3C:
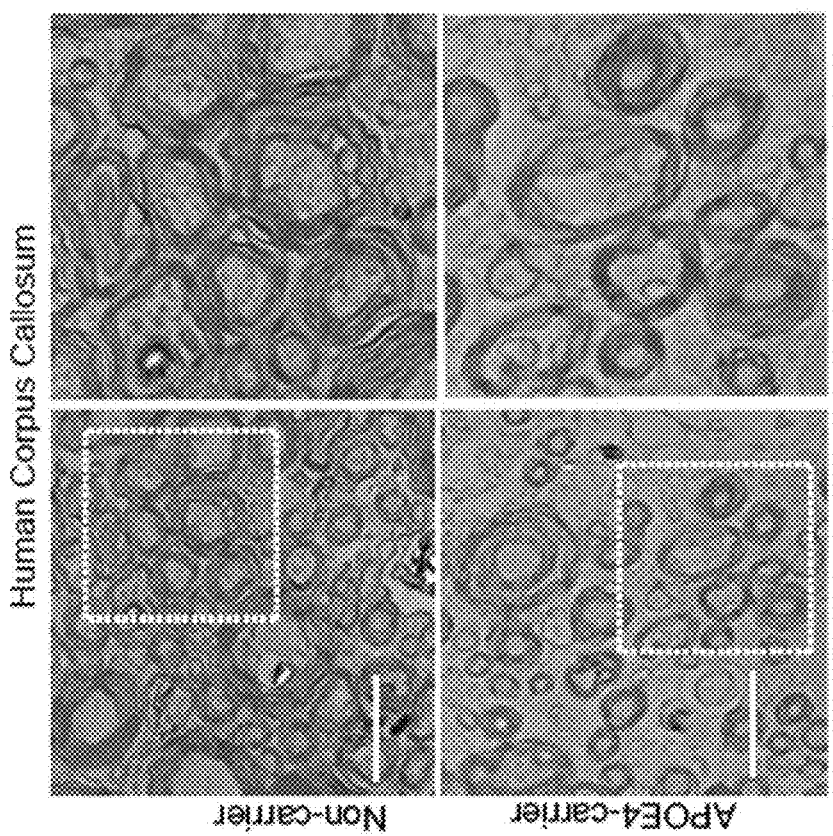
Figure 3D:
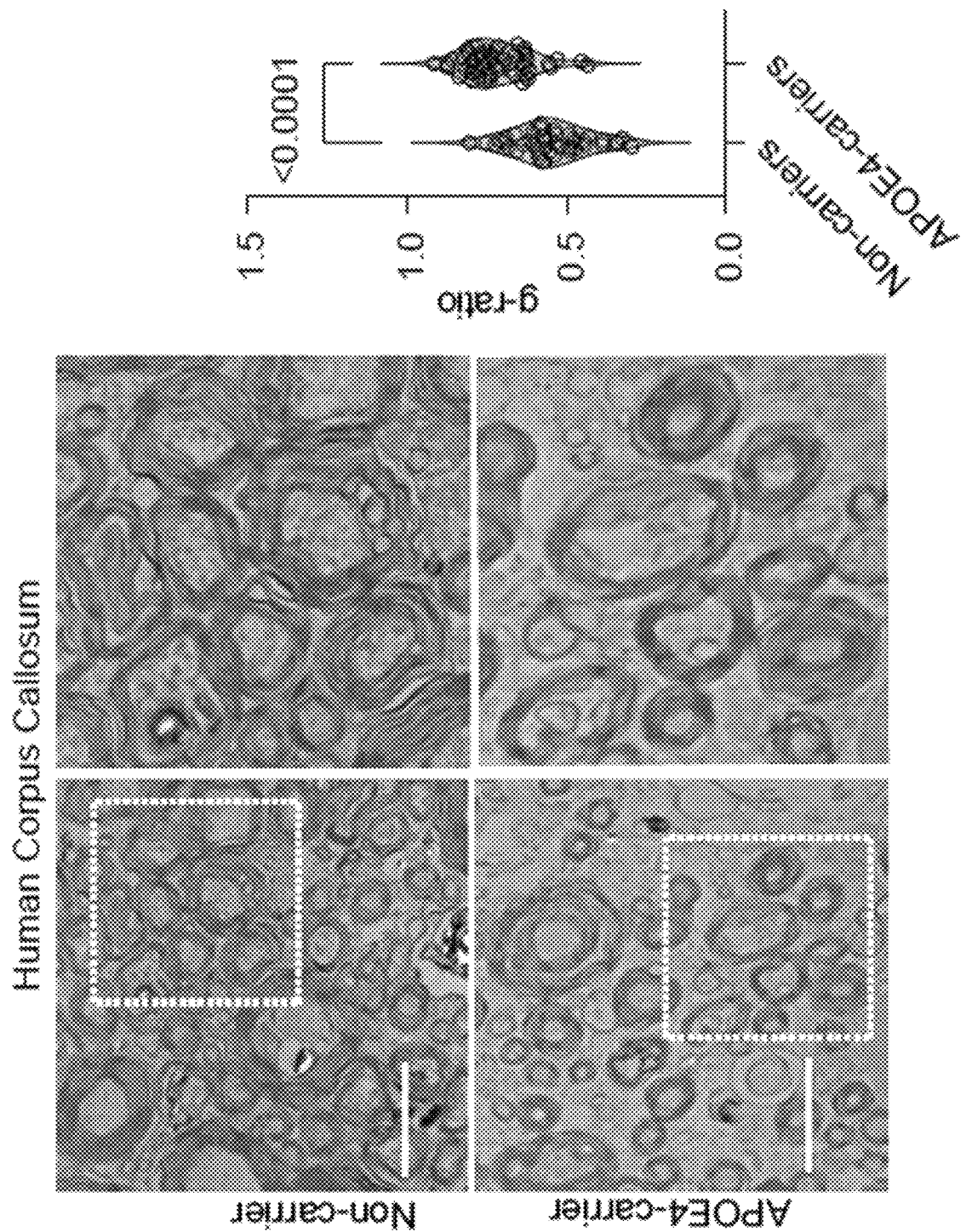
Figure 10B:
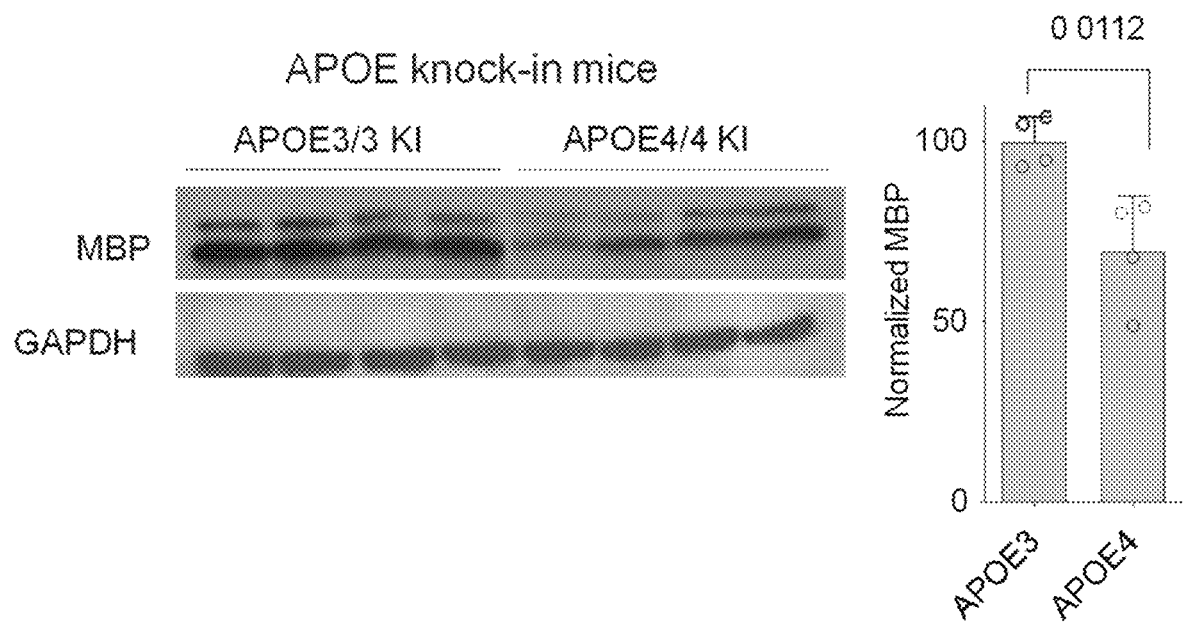
Figure 10C:
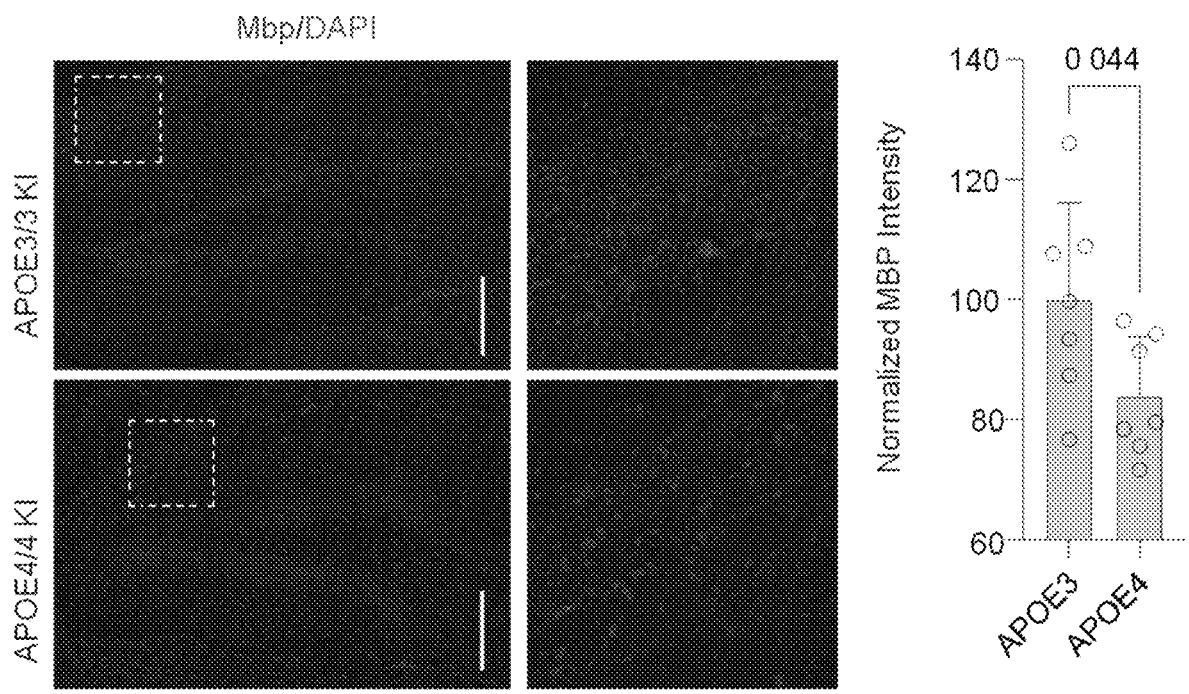

To assess myelin volume and integrity at an ultrastructural level, transmission electron microscopy (TEM) was next performed on human post-mortem corpus callosum samples from 3 APOE4-carriers and 3 non-carriers. Relative to non-carriers, sections from APOE4-carriers appeared to have reduced levels of axonal myelination indicated by fewer and thinner dark-electron dense bands encircling neuronal axons (FIG. 3C). The g-ratio (outer myelin sheath/inner axonal diameter) for 150 neurons for each condition was calculated, which provided a quantitative assessment of the relative myelin levels for each axon. APOE4-carriers had significantly (p<0.0001) higher g-ratios suggesting that corpus callosum from aged APOE4-carriers contains fewer myelinated axons and thinner overall myelin sheath compared to non-carriers. To exclude the possibility that uncontrolled genetic or environmental variables inherent in human samples were influencing myelin phenotypes, myelin levels were next quantified in inbred APOE3 and APOE4 knock-in mice (n=4). In the cortex of APOE4KI mice, total Mbp protein levels were significantly (p=0.0112) reduced compared to aged-matched APOE3KI mice measured by western blotting (FIG. 10B). Likewise, the hippocampus of APOE4KI mice also exhibited significantly less (p=0.044) Mbp immunoreactivity, suggesting that myelin levels may be reduced in APOE4KI compared to APOE3KI mice (FIG. 10C). Ultra-structural imaging of the corpus callosum from 6-month-old knock-in mice revealed that the majority of axons in APOE3 knock-in mice were encircled with dense myelin bands (FIG. 3D). In contrast, corpus callosum from aged-matched APOE4KI mice appeared to contain fewer myelin bands around axons. Relative myelin levels were quantified again using the g-ratio (n=150 neurons for each genotype). APOE4KI mice had significantly (p<0.0001) higher g-ratios compared to APOE3KI mice indicating that relative to APOE3KI mice, APOE4KI mice have thinner myelin sheaths and more unmyelinated axons (n=4 animals per genotype, FIG. 3D). These results demonstrate that APOE4 causes reduced myelination in vivo.

Figure 3E:
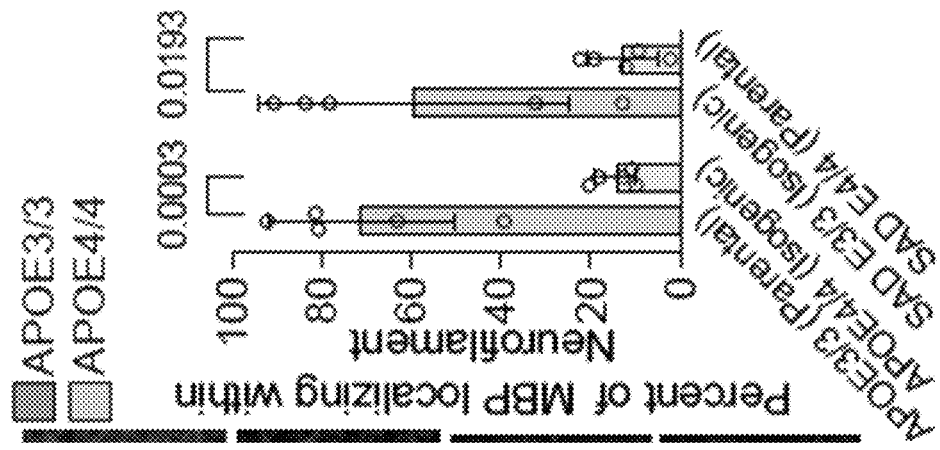
Figure 10D:
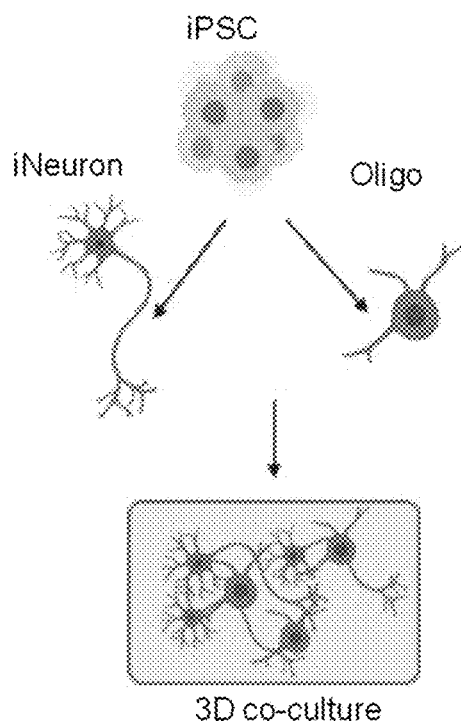
Figure 10E:
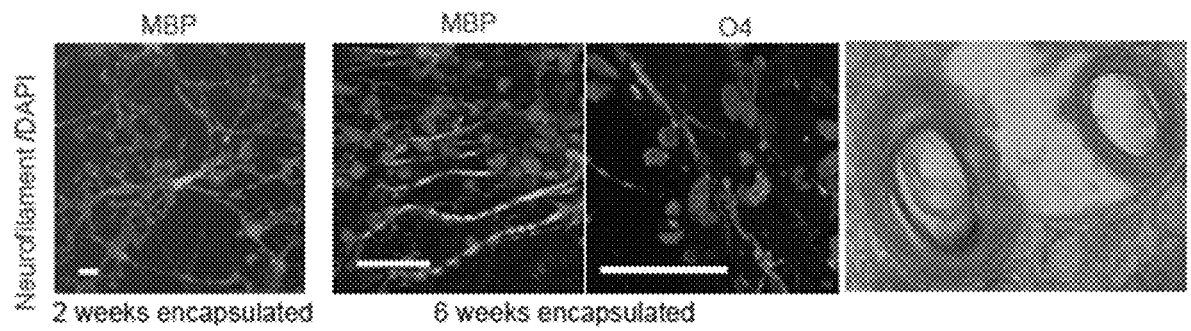
Figure 10F:
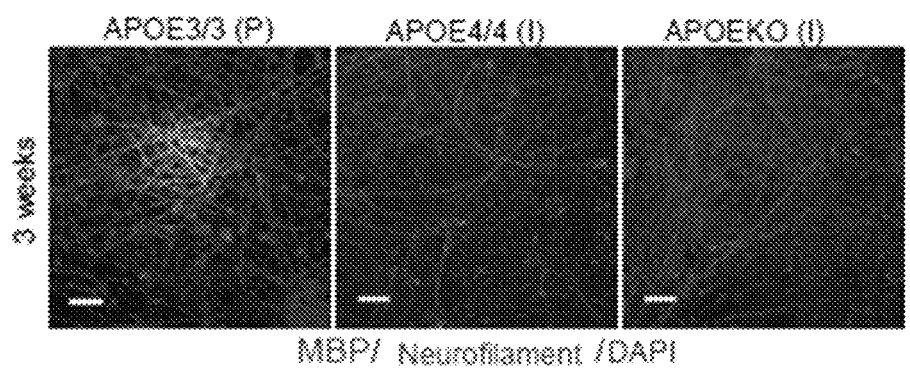
Figure 10G:
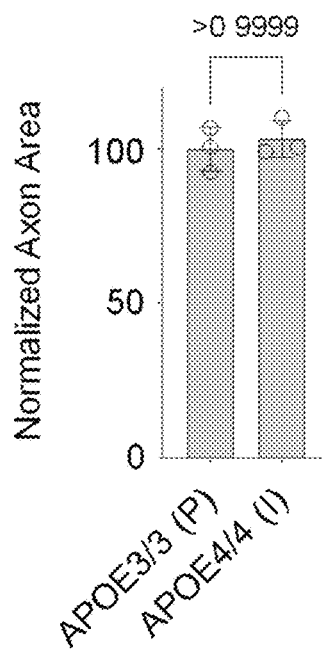

To further investigate the effect of APOE4 on myelination an in vitro model of myelination was developed that employs the genetically controlled isogenic APOE cells derived from CRISPR-edited iPSCs. To achieve this, iPSC-derived oligodendroglia were co-cultured with neurons induced from iPSCs using NGN2 overexpression (iNeurons) in a three-dimensional extracellular matrix that allows each cell type to interact with other cells and self-assemble into tissue-like structures (FIG. 10D). After 2 weeks in these 3D co-cultures, MBP-positive oligodendroglia spread across the culture and engage neurofilament-positive axons (FIG. 10E). After 6 weeks in culture, myelin-associated proteins 04 and Mbp encircled numerous neurofilaments, mimicking biological processes critical to myelination (FIG. 10E). By ultrastructural transmission electron microscopy (TEM) axon segments were also observed ensheathed by electron-dense membrane rings at a low frequency, suggesting the presence of myelinated axons within these in vitro cultures (FIG. 10E). Therefore, it was sought to use this in vitro myelination assay to assess the effect of APOE4 on myelin-associated phenotypes in human cells. Consequently, oligodendroglia/iNeuron co-cultures from two different APOE4/4 and APOE3/3 isogenic sets of iPSC-derived cells were established. In APOE3/3 co-cultures MBP-immunoreactive areas began to sporadically appear after three weeks in vitro (FIG. 10F). After six weeks in vitro, both APOE3 and APOE4 co-cultures contained similar ($p>0.9999$) levels of neurofilament positive signal indicating a similar number of axons (FIG. 10G). However, APOE3 co-cultures exhibited robust MBP immunostaining with approximately 60% of MBP signal surrounding (within 1 um) neurofilament-positive axons (FIG. 3E). In contrast, both sets of isogenic APOE4 co-cultures, exhibited significantly ($p=0.0003$ and $0.0193$) less (<20%) MBP staining that localized with neurofilament suggesting that APOE4 oligodendrocytes were producing less MBP and engaging less with neuronal processes than isogenic APOE3 co-cultures (FIG. 3E).

Figure 3F:
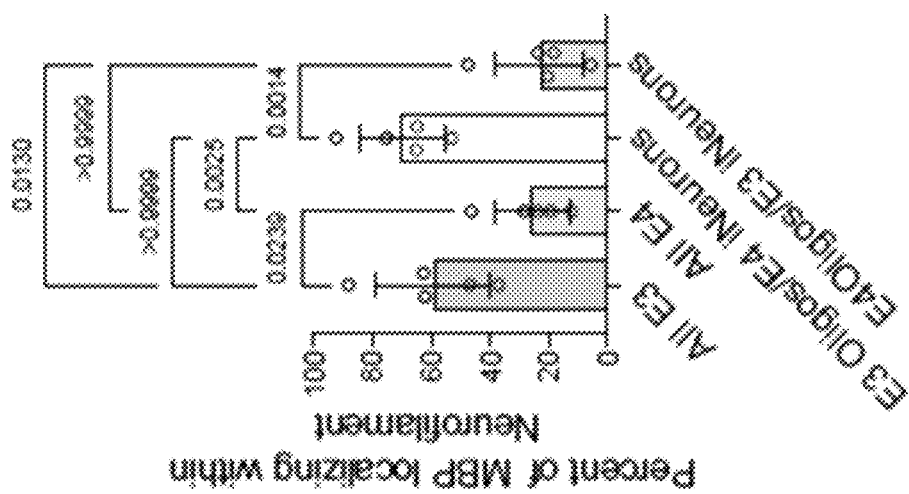
Figure 3G:
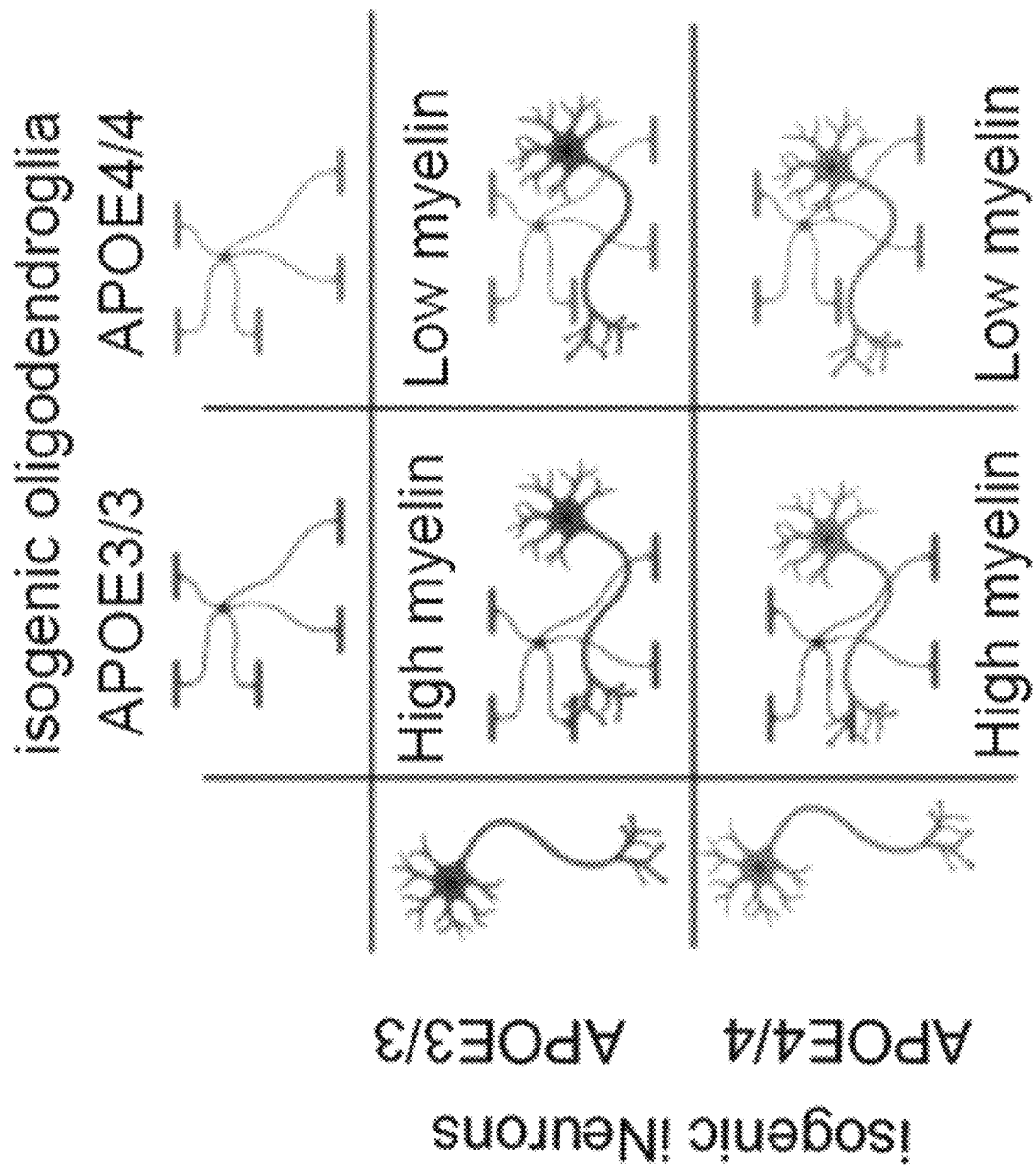

The reduction in myelination associated with APOE4 could arise from autonomous defects in oligodendrocytes, or more complex mechanisms involving paracrine signaling from neurons and other cell types. Therefore, to gain insight into the cell type-specific mechanisms of APOE4 on myelination, a combinatorial experiment was performed where APOE4 oligodendroglia was co-cultured with APOE3 iNeurons and vice versa. APOE3 oligodendroglia co-cultured with isogenic APOE4 iNeurons exhibited a similar ($p>0.9999$) level of MBP staining localizing to neurofilaments as all APOE3 co-cultures, suggesting that APOE4 neurons do not impair the ability of APOE3 oligodendroglia to produce MBP or engage neuronal axons (FIG. 3F). In contrast, APOE4 oligodendroglia co-cultured with APOE3 iNeurons exhibited significantly ($p=0.0130$) reduced MBP staining that localized with neurofilament staining. The levels of MBP surrounding neurofilament in APOE4 oligodendroglia co-cultured with APOE3 iNeurons were similar ($p>0.9999$) to all-APOE4 co-cultures, with only ~20% of neurofilament-positive axons surrounded by MBP staining (FIGS. 3F-3G). This suggests that APOE4 expression in oligodendroglia is sufficient to impair the ability of oligodendroglia to produce MBP and engage neuronal processes critical to myelination. Taken together, these results demonstrate that increased intracellular localization of cholesterol in APOE4 oligodendrocytes correlates with reduced expression of myelin-associated genes, proteins, and axonal myelination in both humans and mice.

Figure 4A:
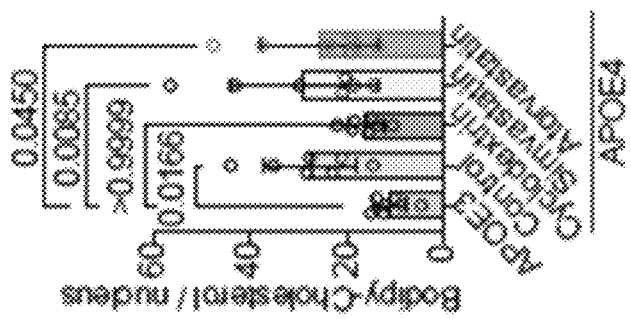
FIGS. 4A-4G: Cyclodextrin treatment rescues myelination defects.
Figure 4B:
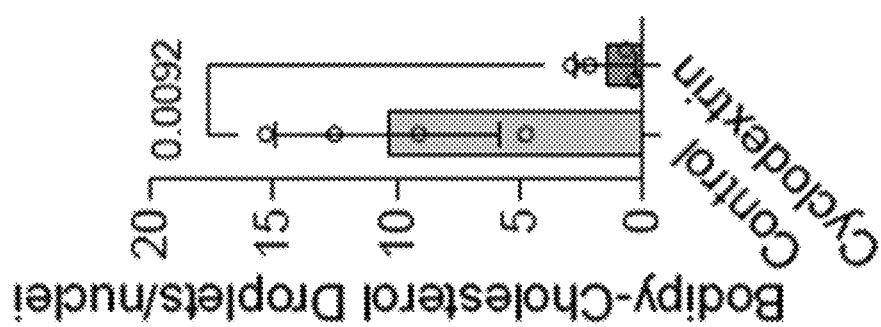

Reducing Intracellular Cholesterol in APOE4 Oligodendrocytes Improves Myelination In Vitro and In Vivo APOE4 expression in oligodendrocytes causes both cholesterol accumulation and impaired myelination. It was reasoned that inhibiting cholesterol biosynthesis and/or facilitating cholesterol transport in APOE4 oligodendrocytes may reduce intracellular accumulation and improve myelination. To test this hypothesis, small molecules that inhibit cholesterol biosynthesis (simvastatin and atorvastatin) and 2-hydroxypropyl-β-cyclodextrin (cyclodextrin), a cholesterol-solubilizing agent known to facilitate cholesterol transport and reduce intracellular cholesterol accumulation associated with Niemann-Pick disease type $C^{56}$, were employed. It was first assessed whether simvastatin, atorvastatin, or cyclodextrin could reduce intracellular cholesterol by treating APOE4 iPSC-derived oligodendroglia with each drug for two weeks and subsequently quantifying the total amount of bodipy-cholesterol staining per condition. APOE4 oligodendroglia cultured in the presence of either cholesterol biosynthesis inhibitors (either simvastatin or atorvastatin) exhibited elevated bodipy-cholesterol staining that was significantly ($p=0.0085$ and $0.0450$) higher than APOE3/3 oligodendroglia (FIG. 4A). However, APOE4 oligodendroglia treated with cyclodextrin exhibited reduced bodipy-cholesterol staining that was not significantly different ($p>0.9999$) from that in APOE3 oligodendroglia (FIG. 4A). In cyclodextrin-treated APOE4 oligodendroglia, a significant ($p=0.0092$) reduction of the number of intracellular droplets of bodipy-cholesterol was observed as well as a significant ($p<0.0001$) reduction of neutral lipid droplets measured by bodipy staining, suggesting that cyclodextrin reduced both intracellular cholesterol and neutral lipid accumulation such as triacylglycerides (FIG. 4B and FIG. 9A). Cyclodextrin treatment also led to significant ($p=0.0011$) upregulation of expression CYP46A1 (FIG. 9B), the primary enzyme that hydroxylates cholesterol in the brain, which facilitates cholesterol trafficking and clearance[51]. In APOE4 oligodendroglia treated with atorvastatin or simvastatin expression of CYP46A1 was not significantly different ($p=0.4324$; $0.0571$) from untreated APOE4 controls (FIG. 9B).

Figure 4C:
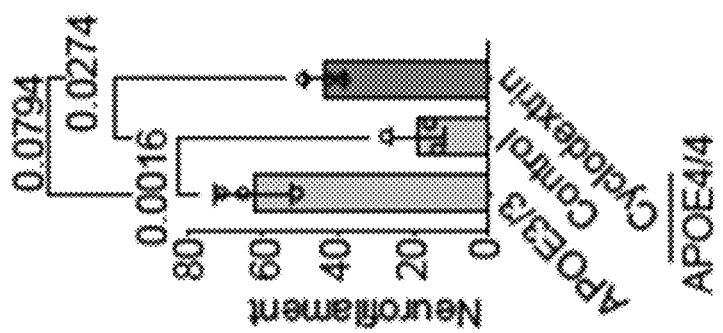

To determine whether cyclodextrin-induced cholesterol reduction in APOE4 oligodendroglia affected myelination, APOE4 oligodendroglia/iNeuron co-cultures were treated with cyclodextrin for 6 weeks and then assessed myelination phenotypes (FIG. 4C). Similar to previous experiments, in all APOE3 co-cultures approximately 60% (62.42%+/−10.304) of MBP staining localized within 1 μm of neurofilament staining (FIG. 4C). In contrast, in untreated APOE4 co-cultures, less than 20% (18.89%+/−7.366) of MBP staining localized with neurofilament staining (FIG. 4C). However, APOE4 co-cultures treated with cyclodextrin had significantly ($p=0.0274$) more (43.44%+/−5.382) MBP staining localized along neurofilament staining (FIG. 4C). The levels of MBP localization with neurofilament in APOE4 cyclodextrin treated cultures were not significantly ($p=0.0794$) different from APOE3 co-cultures (FIG. 4C). This suggests that pharmacologically reducing intracellular cholesterol accumulation in APOE4 oligodendrocytes may facilitate increased myelination in APOE4-carriers in vivo.

Figures 4D, 4E:
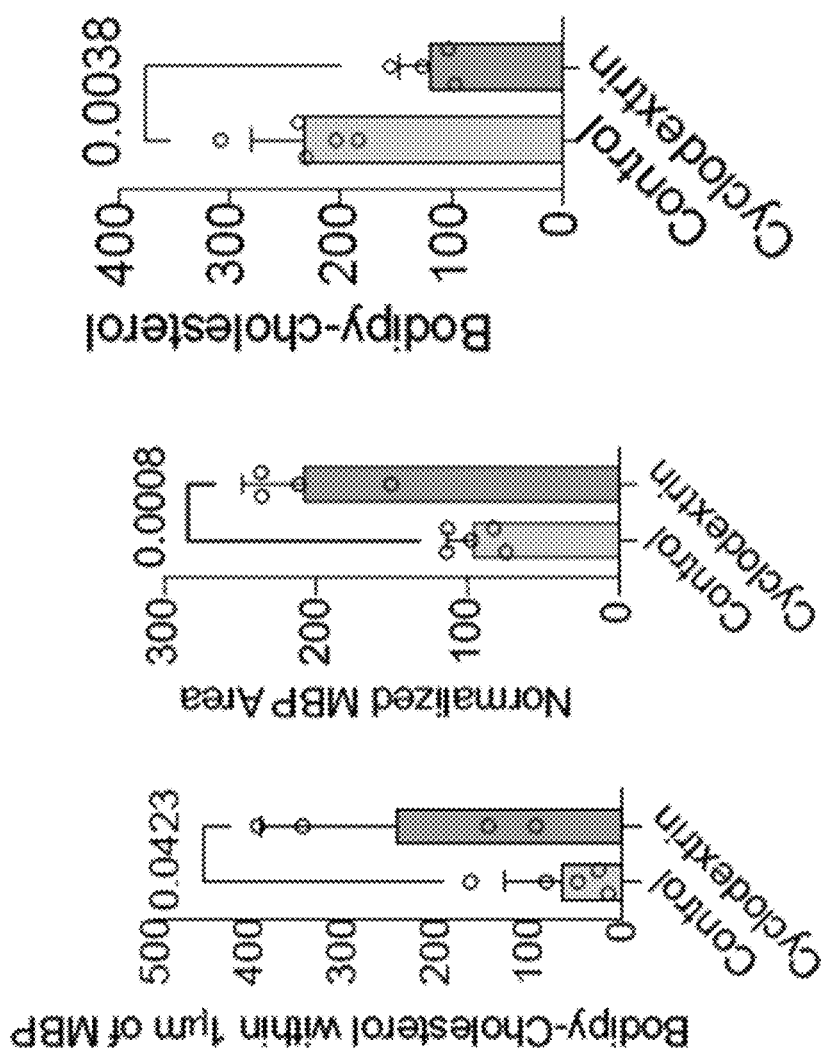
Figure 4F:
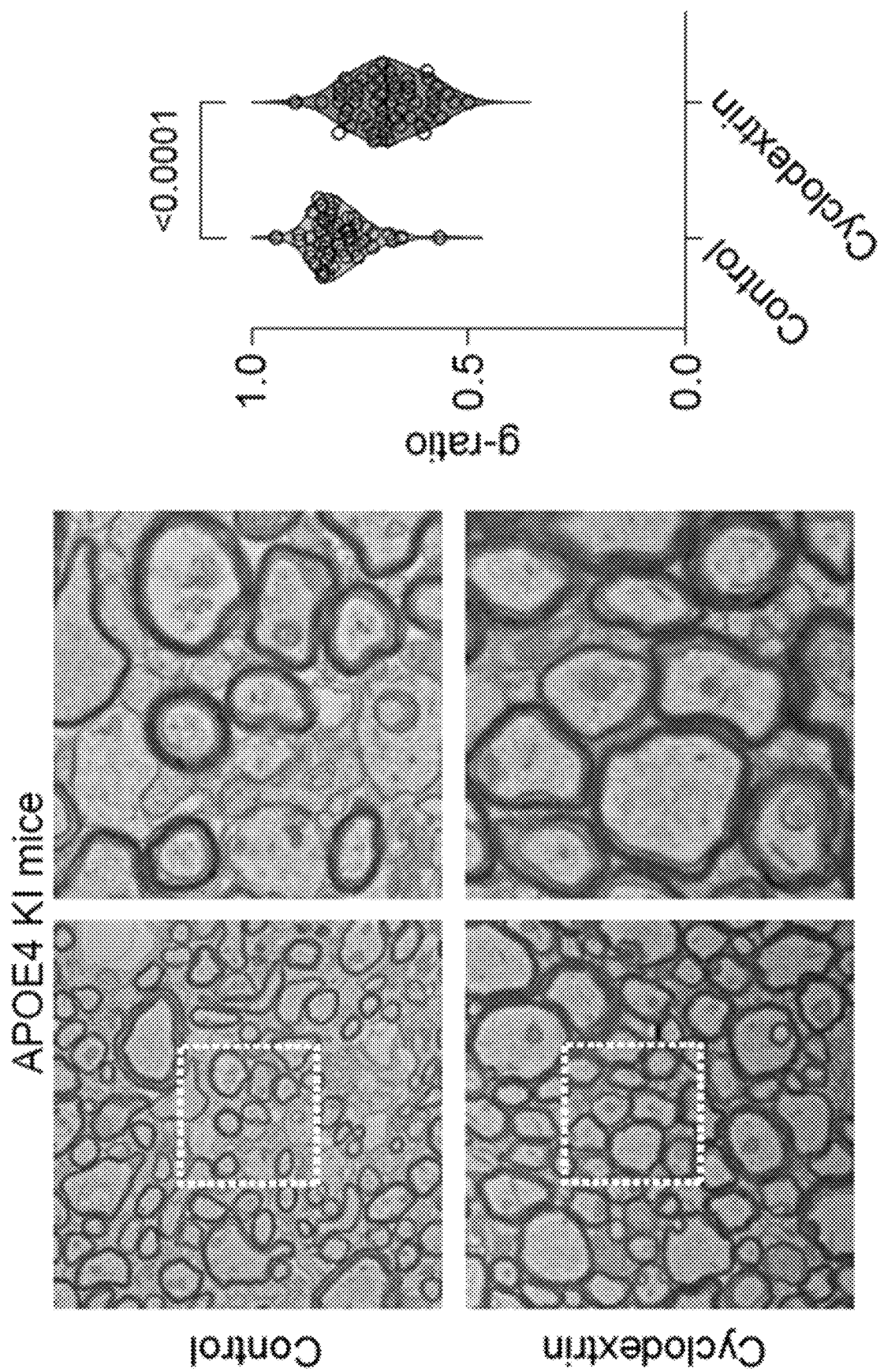

It was next assessed whether cyclodextrin could reduce aberrant cholesterol accumulation in oligodendrocytes and promote increased myelination in APOE4KI mice in vivo. APOE4KI mice were treated with subcutaneous injections of cyclodextrin or saline (control) for eight weeks (n=5 control and 4 cyclodextrin treated mice). In the post-mortem human brain from APOE4-carriers, increased cholesterol accumulations surrounding Olig2-positive nuclei was observed (FIGS. 2C-2D). In the hippocampus of APOE4KI mice treated with cyclodextrin, bodipy-cholesterol staining that accumulated around Olig2-positive nuclei was significantly (p=0.0038) reduced compared to control mice (FIG. 4D). Moreover, in cyclodextrin-treated mice, a significant (p=0.0423) increase in bodipy-cholesterol staining co-localizing within 1 µm of Mbp staining was observed, indicating that cyclodextrin facilitates increased trafficking of cholesterol to the myelin sheath (FIG. 4E). Encouragingly APOE4KI mice treated with cyclodextrin-treated mice exhibited significantly (p=0.0008) increased Mbp staining, suggesting that cyclodextrin may increase myelin levels in APOE4 mice (FIG. 4E). To more directly assess myelination in cyclodextrin treated APOE4 mice, TEM-based ultrastructural analysis was performed. APOE4 mice treated with cyclodextrin had a significantly (p<0.0001) lower g-ratio (n=150 neurons for each genotype) than control mice indicating an increased number of myelinated axons and thicker myelin sheaths in cyclodextrin treated mice (FIG. 4F). Collectively, this data demonstrates that pharmacologically enhancing cholesterol transport in APOE4-carriers can increase myelination.

Figure 4G:
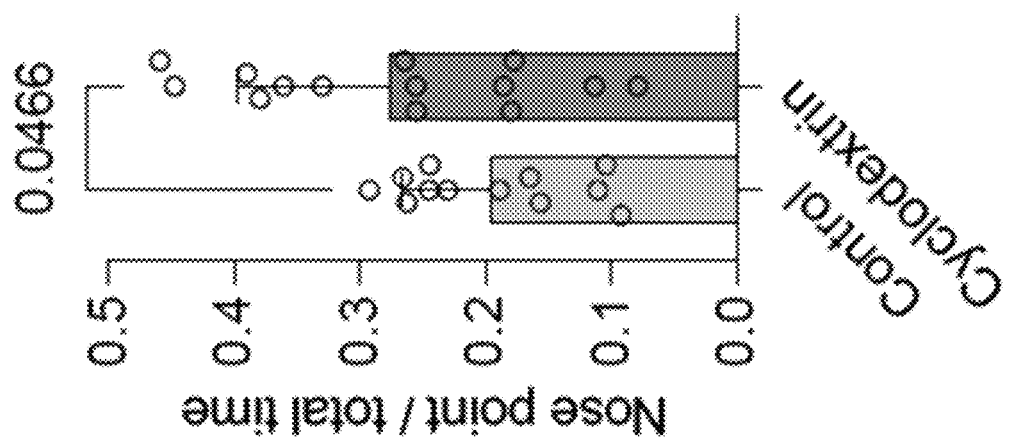
Figure 4G:
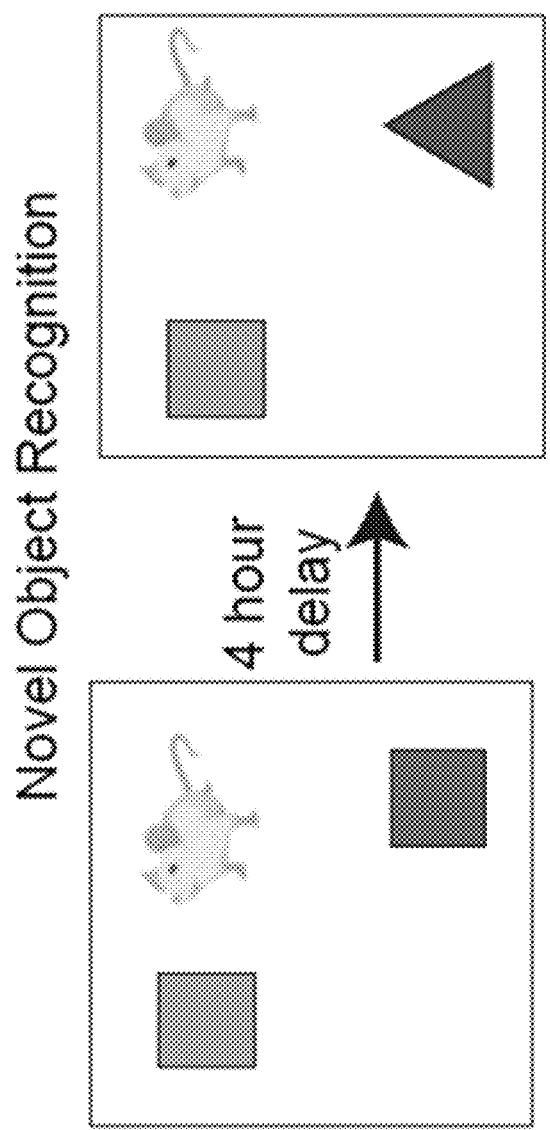
Figure 9C:
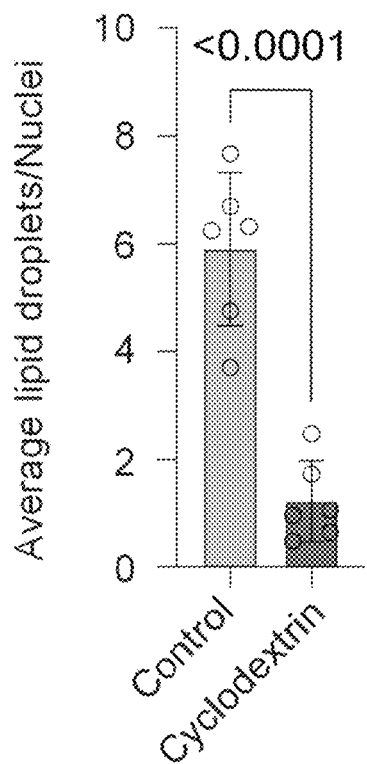
Figure 9C:
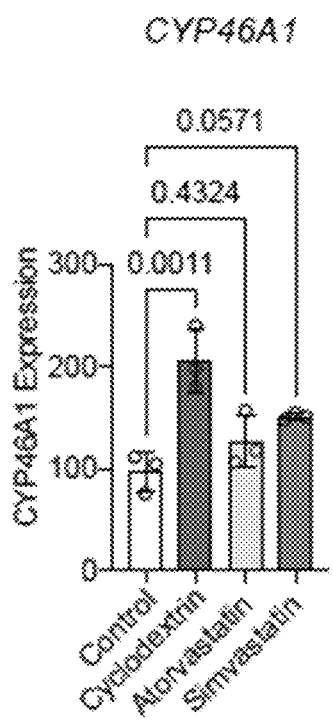
Figure 9C:
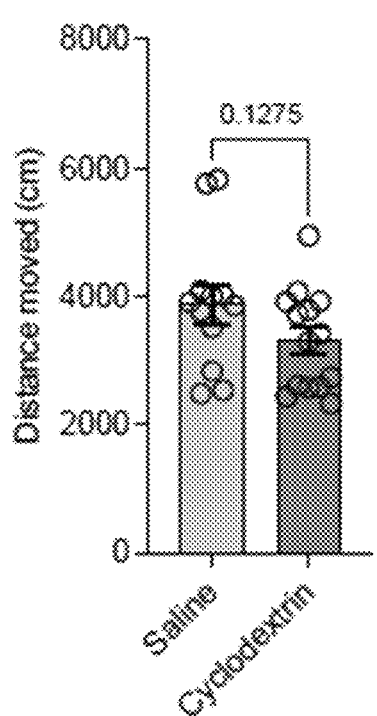
Figure 9C:
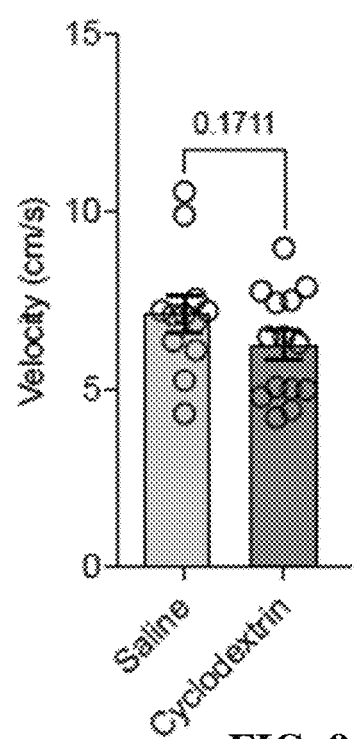
Figure 9C:
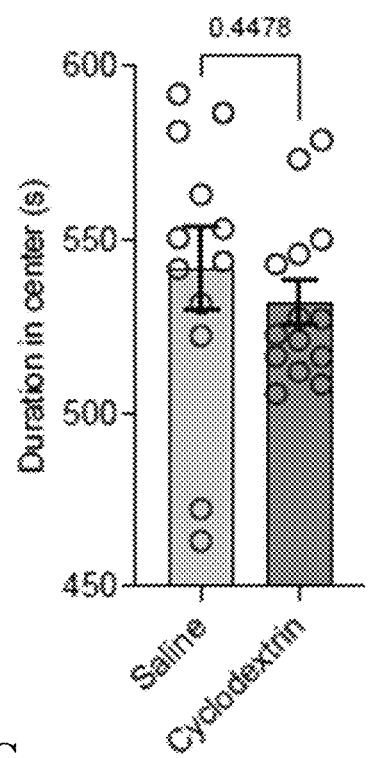

To investigate whether the increased myelination observed in cyclodextrin treated APOE4KI mice could promote functional improvements, the novel object recognition assay was performed to evaluate learning and memory (FIG. 4G)[57]. During an open field task, control (n=12) and cyclodextrin-treated (n=14) APOE4KI mice exhibited similar total distance moved (p=0.1275), velocity (p=0.1711), and duration in the center of the cages (p=0.4478), suggesting cyclodextrin treatment did not affect locomotor or anxiety phenotypes (FIG. 9C). However, when exposed to a novel object, APOE4KI mice treated with cyclodextrin had a significantly (p=0.0466) increased preference for interacting with the novel object than control APOE4KI mice, suggesting that cyclodextrin treatment may improve learning and memory (FIG. 4G).

Discussion

Taken together, these results demonstrate that APOE4 alters cholesterol homeostasis across multiple cell types in the human brain. Cholesterol is most prominently dysregulated in oligodendrocytes, leading to impaired myelination. Pharmacologically promoting cholesterol efflux causes increased myelination in vitro and in vivo and improved cognition in APOE4KI mice. These results establish a causal connection between cholesterol dysregulation and myelination in APOE4-carriers, which may influence cognitive outcomes in humans with AD. Collectively, this Example establishes a new pathological mechanism in AD and uncovers therapeutic strategies for reversing APOE4-associated cognitive impairments.

AD is primarily considered a grey-matter disorder with the accumulation of neuritic plaques and neurofibrillary tangles causing neuronal injury and loss. However, cholesterol and lipid-related pathologies have long been observed in the post-mortem brains of AD patients since the first described case[25]. Likewise, reduced myelin volumes and integrity have been documented in AD patients[58-60]. MRI studies have observed white matter changes and myelin damage present in many individuals before the onset of AD symptoms[61]. These studies even find reduced myelin volume in the fourth and fifth decade of life predicts a higher probability of cognitive impairments decades later[62]. In addition, a recent single-cell transcriptomics study identified oligodendrocytes as one of the most dysregulated cell types in the post-mortem human AD brain[29,63]. Despite these associations, cholesterol, lipid, and myelin abnormalities have largely been considered secondary symptomatic events with a limited causal role in AD pathogenesis.

This Example is the first to demonstrate that APOE4, the strongest genetic risk factor for AD, directly impairs cholesterol trafficking and localization in the human brain causing a reduction of total myelin. APOE is highly expressed in subpopulations of human oligodendrocytes[64]. Neuroimaging studies have identified that human infants carrying APOE4 have reduced myelin volumes and altered cognitive maturation trajectories relative to APOE3/3 individuals[65,66]. Both amyloid and aggregated tau are cytotoxic to oligodendrocytes and their progenitors[67]. OPCs exhibit a senescent phenotype in response to amyloid plaques, indicating that progenitor pools necessary to replenish and support oligodendrocytes and myelin are often compromised in AD[68]. Myelin is critical for neuronal processes including long-range connectivity, fast electrical transmission, and precise spike timing, all critical to high-level cognitive functions such as learning and memory[69-72]. Therefore, it is interesting to speculate that in APOE4-carriers, dysregulation of cholesterol-related processes causes a reduction in myelin levels early in life that make APOE4-carriers particularly vulnerable to amyloid and tau-mediated neurotoxicity that accumulate in the aged brain. This would suggest that pharmacological, dietary, or lifestyle interventions focused on increasing myelin volume could increase cognitive reserves in APOE4 individuals.

These mouse studies demonstrate that pharmacologically facilitating cholesterol trafficking can improve performance in behavioral tasks associated with learning and memory. It was also found that expression of genes associated with cholesterol metabolism and regulation correlate with cognitive scores at the end of life in both APOE4 (FIG. 2B) and APOE3 carriers (data not shown). Therefore, there appears to be a causal link between dysregulated cholesterol pathway and cognitive function. Moreover, cholesterol dysregulation is increasingly recognized as a hallmark of AD capable of regulating amyloid and tau pathologies[73,74]. Therapeutic efforts to target cholesterol abnormalities in AD have largely focused on inhibiting cholesterol biosynthesis using statins[73]. However, cholesterol biosynthesis inhibitors have had inconsistent results in AD, with some studies reporting cognitive improvements and others finding no or even detrimental effects[75,76]. It was found that statins failed to mitigate cholesterol abnormalities in APOE4 oligodendrocytes whereas targeting cholesterol trafficking reduced cholesterol abnormalities, and improved cognitive function in APOE4 mice. These results imply that a direct effect of APOE4 is aberrant cholesterol trafficking whereas upregulation of cholesterol biosynthesis likely occurs downstream, potentially as a compensatory mechanism to counter impaired cholesterol trafficking by APOE4. This demonstrates that, while cholesterol has a central role in cognitive outcomes, approaches targeting cholesterol likely need to consider APOE genotype to optimize therapeutic strategies.

This Example leverages a multi-modal approach that integrates single-cell transcriptomics and lipidomic analysis of post-mortem human brains with functional studies employing isogenic stem cell lines and knock-in mouse studies. This enables comprehensive mapping of the transcriptional effects of APOE4 on each cell type and also investigation of the mechanisms underlying and leading up to end-stage transcriptomic and pathological signatures observed in the post-mortem human brain. Ultimately, this integrative approach pinpoints for the first time that impaired cholesterol trafficking contributes to myelin defects in the APOE4 brain, opening new avenues for diagnosing and treating AD.

Methods

ROSMAP Subject Selection.

A total of 32 individuals were selected from the Religious Orders Study or the Rush Memory and Aging Project (ROSMAP), two harmonized longitudinal cohort studies of ageing and dementia that includes extensive post-mortem pathological evaluations and clinical data collected annually, as previously described[34]. Details of clinical and pathological data collection methods have been previously reported[77]. To assess APOE4 effects in the context of AD pathology, 6 control subjects with no or very low pathology (no-pathology) and 6 age-matched subjects with severe β-amyloid, tau pathology, and cognitive decline (AD-group) were selected independently for APOE3/3 and APOE3/4 carriers. For APOE3/3 and APOE3/4 carriers, subjects were balanced between sexes (12 each) and matched for age (median=84.63 APOE3/3; median=85.19 APOE3/4). Informed consent and an Anatomic Gift Act were obtained from each subject, and the Religious Orders Study and Rush Memory and Aging Project were approved by an Institutional Review Board (IRB) of Rush University Medical Center. All subjects signed a repository consent that allowed their data and biospecimens to be shared.

Isolation of Nuclei from Frozen Post-Mortem Brain Tissue.

The protocol for the isolation of nuclei from frozen post-mortem brain tissue was adapted from a previous study[25]. All procedures were carried out on ice or at 4° C. In brief, post-mortem brain tissue was homogenized in 700 µl homogenization buffer (320 mM sucrose, 5 mM $CaCl_2$, 3 mM $Mg(CH_3COO)_2$, 10 mM Tris HCl pH 7.8, 0.1 mM EDTA pH 8.0, 0.1% IGEPAL CA-630, 1 mM β-mercaptoethanol, and 0.4 U/µl recombinant RNase inhibitor (Clontech)) using a Wheaton Dounce tissue grinder (15 strokes with the loose pestle). Then the homogenized tissue was filtered through a 40 µm cell strainer, mixed with an equal volume of working solution (50% OptiPrep density gradient medium (Sigma-Aldrich), 5 mM $CaCl_2$, 3 mM $Mg(CH_3COO)_2$, 10 mM Tris HCl pH 7.8, 0.1 mM EDTA pH 8.0, and 1 mM β-mercaptoethanol) and loaded on top of an OptiPrep density gradient (750 µl 30% OptiPrep solution (30% OptiPrep density gradient medium, 134 mM sucrose, 5 mM $CaCl_2$, 3 mM $Mg(CH_3COO)_2$, 10 mM Tris HCl pH 7.8, 0.1 mM EDTA pH 8.0, 1 mM β-mercaptoethanol, 0.04% IGEPAL CA-630, and 0.17 U/µl recombinant RNase inhibitor) on top of 300 µl 40% OptiPrep solution (40% OptiPrep density gradient medium, 96 mM sucrose, 5 mM $CaCl_2$, 3 mM $Mg(CH_3COO)_2$, 10 mM Tris HCl pH 7.8, 0.1 mM EDTA pH 8.0, 1 mM β-mercaptoethanol, 0.03% IGEPAL CA-630, and 0.12 U/µl recombinant RNase inhibitor). The nuclei were separated by centrifugation (5 min, 10,000 g, 4° C.). A total of 100 µl of nuclei was collected from the 30%/40% interphase and washed with 1 ml of PBS containing 0.04% BSA. The nuclei were centrifuged at 300 g for 3 min (4° C.) and washed with 1 ml of PBS containing 0.04% BSA. Then the nuclei were centrifuged at 300 g for 3 min (4° C.) and re-suspended in 100 µl PBS containing 0.04% BSA. The nuclei were counted and diluted to a concentration of 1,000 nuclei per microliter in PBS containing 0.04% BSA.

Droplet-Based snRNA-Seq.

For droplet-based snRNA-seq, libraries were prepared using the Chromium Single Cell 3' Reagent Kits v3 according to the manufacturer's protocol (10× Genomics). The generated snRNA-seq libraries were sequenced using NextSeq 500/550 High Output v2 kits (150 cycles) or NovaSeq 6000 S2 Reagent Kits.

snRNA-Seq Data Preprocessing.

Gene counts were obtained by aligning reads to the GRCh38 genome using Cell Ranger software (v.3.0.2) (10× Genomics). To account for unspliced nuclear transcripts, reads mapping to pre-mRNA were counted. After quantification of pre-mRNA using the Cell Ranger count pipeline, the Cell Ranger aggr pipeline was used to aggregate all libraries (without equalizing the read depth between groups) to generate a gene-count matrix. The Cell Ranger 3.0 default parameters were used to call cell barcodes.

Cell Inclusion Criteria.

Outlier cells with less than 500 or more than 10,000 genes detected were excluded, and only genes detected in at least 10 cells were considered. The following quality measures were quantified for each cell: (1) the number of genes for which at least one read was mapped (indicative of library complexity); (2) the total number of counts; and (3) the percentage of reads mapped to mitochondrial genes (used to approximate the relative amount of endogenous RNA and commonly used as a measure of cell quality). Cells with a discriminatively high ratio of mitochondrial to non-mitochondrial read counts were excluded using unbiased k-means clustering-based binarization (k=2). Nuclear-encoded protein coding genes were considered for downstream analyses. After applying QC filtering steps, the dataset included 17,915 genes profiled in 164,741 nuclei.

Clustering Analysis.

All dimensionality reduction, clustering, and visualization analyses were performed using the computational analysis framework ACTIONet reported in [70] and available at (github.com/shmohammadi86/ACTIONet, version ACTIONet-Legacy). Briefly, for each round of clustering, single value decomposition is performed for feature (gene) dimensionality reduction, and multiple rounds of matrix decomposition are performed to identify a lower dimensional cell state representation for each individual cell. This cell state representation is operationalized as a set of variables quantifying the relative contribution of latent cell state patterns learned from data to optimally describe the transcriptional heterogeneity of the whole dataset. This representation is used to build a cell network or embedding whose structure captures transcriptomic state relationships at single-cell level. Discrete groups of cells with similar transcriptomes (cell clusters) were identified by applying the Leiden graph-based clustering algorithm[78] to the resulting network.

Pathway Analysis.

1. Databases.

Both the APOE-associated and lipid-associated pathway databases were curated by filtering the union of pathways from GO, KEGG, and HGNC gene families (the union of which was used in full for the analysis in FIGS. 6A-6B) for gene sets that contain, respectively, at least one gene in the set A={'APOE','LRP1','LRP2','LRP4','LRP5','LRP6', 'LRP8','LRP1B','LDLR','VLDLR','SORL1'} or for gene sets whose name contains at least one of the following terms B={'sterol','athero','cholest','LDL','HDL','lipoprotein', 'triglyceride','TAG','DAG','lipid','steroid','fatty acid'}

2. Pathway Activity Scores.

Individual-cell type level gene expression profile averages were first computed, followed by calculation of pathway activity scores, as previously implemented in the R package GSVA[79]. Briefly, GSVA first estimates gene-wise (non-parametric) Gaussian cumulative density functions based on normalized sample expression values. A KS-like random walk statistic is computed for every gene set and the enrichment score is calculated as the difference between the largest positive and negative random walk deviation from zero, which ensures that the scores follow the standard normal distribution and meet the assumptions for linear modeling. The following parameters were used to evaluate the GSVA function: mx.diff=TRUE, kcdf=c("Gaussian"), min. sz=10. Activity scores computed this way accurately recovered cell type signatures not recovered by equally-sized randomly sampled genesets (FIG. 6I), suggesting that this approach captures transcriptomically-encoded biological signals in snRNA-sequencing data.

3. Cell Type Specificity of APOE-Associated Pathways.

GSVA was used to compute pathway activity profiles for APOE-associated genesets across major cell types. The average gene expression across all cells of a given type was used as a measure of expression for that cell type. GSVA scores were computed over the resulting average cell type profiles. To define cell type specificity, the relative pathway activity across cell types was measured using a z-score, and each pathway was assigned to the cell type with maximum activity. Correspondence between cell type assignments and relative pathways activity scores was verified empirically by hierarchical clustering and heatmap plot visualization.

4. Differential Pathway Activity Analysis.

First, GSVA was used to compute pathway activity scores on individual-level average expression profiles in each cell type of interest. To minimize the discovery of false positive effects, activity scores were computed only for unique gene sets (i.e. unique combinations of genes) after filtering out genes that were not expressed in a given cell type (defined as a nonzero detection rate $\geq 10\%$). For each pathway-cell type combination, pathway activity scores were modeled using a multivariate linear model as follows:

Pathway activity=$\beta 0$*APOE4+$\beta 1$*amyloid+$\beta 2$*$nft$+
$\beta 3$*age_death+$\beta 4$*sex+$\beta 5$*pmi Here, APOE4 is a binary variable, encoding the presence of at least one E4 allele. Amyloid and nft are averages of continuous measurements of pathology across 8 and 5 brain regions, respectively, as evaluated and reported by ROS-MAP. Age_death is a continuous measurement indicating age at death, pmi represents the post-mortem-interval (a continuous measurement), and sex is a binary variable encoding biological sex. $\beta 0$ represents the additive effect (maximum likelihood estimate) of APOE4 ($\geq 1$ allele) on pathway activity, when accounting for other confounding variables that might be correlated with, and thus explain, a portion of the variation observed in the activity of a pathway of interest.

5. Pathway Annotations and Counting.

For the APOE-associated and lipid-associated perturbed gene sets, pathways were annotated manually and renamed a subset for clarity. Overrepresentation of terms of interest among top-perturbed pathways ('lipids' or 'cholesterol/sterol' for the APOE-associated and lipid-associated analyses, respectively) were estimated by cell type using a hypergeometric statistical test (i.e. sampling without replacement) with the following parameters:

q=# of significant perturbed 'lipids' or 'cholesterol/sterol' pathways
k=# of significantly perturbed pathways overall
m=# of 'lipids' or 'cholesterol/sterol' pathways in the database
n=# of total pathways in the respective database Where the density distribution is given by:

$$Pr(X = q) = \frac{\binom{m}{q} + \binom{n-m}{k-q}}{\binom{n}{k}}$$

provides the expected probability of enrichment under the null, random model. Computations were performed using the phyper( ) function in R, with lower.tail=FALSE.

Lipid-related pathways were defined as having at least one term in set L as part of their gene set name.
L={'sterol','athero','cholest','LDL','HDL','lipoprotein', 'triglyceride','TAG','DAG','lipid','steroid','fatty acid'} and cholesterol/sterol-related pathways were defined as having at least one term in set C as part of their gene set name.
C={'sterol','cholesterol','steroid'}

6. Differential Gene Expression by NBMM.

Per-gene expression levels per cell type were modeled as a negative binomial model with random effects that model both within-individual and between-individual effects, as implemented in the R package NEBULA[80]. Briefly, NEBULA models counts for each gene as sampled from a negative binomial distribution, parameterized by a mean and variance. The mean parameter is modeled as an exponential scaled by a scaling factor (total library count per cell). The exponent is modeled as a linear combination of fixed and random effects (individual of origin), where the fixed effects are a linear combination of predictors:

fixed effects=$\beta 0$*APOE4+$\beta 1$*AD+$\beta 2$*$nft$+
$\beta 3$*age$_{death}$$\beta 4$*sex+$\beta 5$*pmi Where the $\beta 0$ and p-value were computed with respect to the APOE4 variable of interest, when controlling for the remaining variables.

7. Pathway Dysregulation by Gene Set Enrichment Analysis (GSEA).

For a subset of highly relevant pathways, a second statistical analysis was performed to validate that the findings are reproducible across methods. To this end, Nebula (above) was used to model gene expression changes associated with APOE4 in oligodendrocytes.

Next, for each gene, the following score s was computed:

$s$=−log 10($p$−value)*sign($\beta 0$)

Genes were rank ordered based on the score s. An R implementation of gene set enrichment analysis (fgsea) was used to estimate the statistical overrepresentation of Gene Ontology gene sets within high-scoring, differentially expressed genes. Cholesterol/sterol-related processes with a significant (p-adjusted<0.05) APOE4 effect are shown in FIG. 3G.

8. Pathway Activity Distribution.

To quantify the degree of cell-type-specific transcriptional activity related to cholesterol, the union of pathways from GO, KEGG, and HGNC gene families was filtered for pathways whose name contains the term 'cholest'. Pathway-level activity scores were computed on cell-type-level averages and their distributions plotted.

Single-Cell Differential Gene Expression.

Differential gene expression between groups of individual cells was estimated using a Wilcoxon rank sum test, as implemented in the R package presto (github.com/immunogenomics/presto). Differential effects were computed exclusively on APOE3/3 vs APOE3/4 cells with an equal number AD and non-AD individuals per group, unless otherwise specified.

Comparative Analysis of iPSC and Post-Mortem Transcriptomes.

To assess whether corresponding cell types in the iPSC and post-mortem data showed consistent transcriptomic signatures relative to remaining cell types, while accounting for sequencing and batch effects, scaled gene expression values (mean-centered, standard deviation=1) were first independently computed for each dataset and then concatenated into a normalized expression matrix. Pathway activity scores were computed on this concatenated matrix using GSVA. Principal component analysis was performed on the concatenated matrix of gene-by-individual (or replicates for iPSC). Pairwise distances between individual-level cell type averages from post-mortem tissue and iPSC-derived were computed in scaled mean-centered gene space.

Analysis of Bulk RNA-Sequencing Data from APOE3 and APOE4 Isogenic iPSC-Derived Oligodendroglia.

Raw FASTQ data were quasi-mapped to a reference transcriptome derived from the GRCh38 human genome assembly and quantified using Salmon. Differential gene expression testing was performed with DESeq2 with median-ratio count normalization, parametric dispersion estimation, and additional count normalization by variance-stabilizing transformation. GSVA was used to compute differential pathway activity scores on replicate-level bulk sequencing profiles. A simple linear model, with APOE status as the single predictor, was used to compute effect sizes and confidence intervals.

Analysis of Bulk RNA-Sequencing Data from Drug-Treated Isogenic iPSC-Derived Oligodendroglia.

Paired-end reads were aligned to the human genome reference GRCh37.p13 using the BWA v0.7.16a. Mapped reads were summarized to gene level counts using the feature Counts function of Rsubread (bioconductor.org/packages/release/bioc/html/Rsubread.html), considering gencode v19 gene annotation for gene reference.

APOE Oligodendroglia Drug Treatment.

Cells were plated onto a Millipore eight-chamber glass slide, at a density of 250,000 cells per well. Cells were then cultured in Neurobasal media, supplemented with PDGFR-α, NT3 and β-FGF. Cells were treated with either Atorvastatin [1 μM], Simvastatin [1 μM], or Cyclodextrin [10 mM] for two weeks. Cells were fixed with 4% PFA, and stained for Bodipy-cholesterol, WGA-555 and DAPI.

APOE Oligodendroglia Bulk RNA-Sequencing.

700 μL of EtOH and Trizol were added at a 1:1 ratio to each well, and cells were collected into tubes. Samples were spun for 1 minute at 1300 gs. The procedure was then followed according to Qiagen's RNeasy Plus Kit instructions. 500 ng/ul of RNA was recovered per sample (n=3 biological replicates per condition). Sample library prep and bulk sequencing was performed by the BioMicro Center at MIT's Department of Biology, using the NextSeq Illumina platform.

APOE Oligodendroglia Lipidomics.

Cell pellets from oligodendrocytes were extracted by adding 600 μL MeOH, 300 μL H20, and 400 μL chloroform. Samples were vortexed for 10 minutes and centrifuged for 10 minutes at 10,000×g at 4° C. The nonpolar layer was transferred to a glass vial and dried under a stream of N2 gas and samples were stored at −80° C. Dried lipids were resuspended with 200 μL of 1:1:1 MeOH:Acetonitrile:2-propanol and 10 μL was injected for analysis by mass spectrometry. The LC-MS system uses an Accela UPLC pump (Thermo Scientific, San Jose, CA) and an Exactive orbitrap mass spectrometer (Thermo Fisher Scientific, San Jose, CA). Chromatography was performed using a Luna C8 reversed-phase column (150×2.0 mm, 3 μm particle size, 100 Å poresize, Phenomenex, Torrance, CA) with a binary gradient (solvent A: 97:3 water/methanol with 10 mM tributylamine and 15 mM acetic acid (pH 4.5), and solvent B: 100% methanol). The gradient ran linearly from 80-99% B from 0 to 20 min, remaining at 99% B from 20 to 40 min, from 99% B to 80% B to 41 min, and remaining steady at 80% B to 50 min to re-equilibrate the column at a flow rate of 200 μL/min. The autosampler temperature was held at 4° C., injection volume 10 μl, and column temperature 25° C. The mass spectrometer was operated in negative and positive ionization modes. The electrospray ionization (ESI) settings were: sheath gas flow rate 30 (arbitrary units), auxiliary gas flow rate 10 (arbitrary units), sweep gas flow rate 5 (arbitrary units), spray voltage 3 kV, capillary temperature 325° C., capillary voltage −50 V, tube lens voltage 100 V, and skimmer voltage −25 V. The mass spec resolution was set to 100,000 resolving power at m/z 200 and the automatic gain control (ACG) was set to high dynamic range with a maximum injection time of 100 ms. The scan range was 200-400 m/z in the first 20 min and 300-575 m/z in the subsequent 30 min. Resulting mass spectrometry data was analyzed using El-Maven (Elucidata.io) and compounds were identified using m/z or using a library of standards with known retention times[81].

Immunohistochemistry.

Animals were anaesthetized via exposure to gaseous isoflurane, and transcardially perfused with ice-cold PBS. The brains were dissected out, one hemisphere frozen in dry ice, and one hemisphere drop-fixed in 4% paraformaldehyde. The post-fixed hemisphere was sliced at a thickness of 40 μm using a Leica vibratome. Slices were blocked with a buffer containing 0.3% Triton-X and 10% normal donkey serum for two hours at room temperature, before being incubated with primary antibody overnight at 4° C. Slices were then washed with PBS and incubated with secondary antibody for two hours at room temperature, washed with PBS again, and mounted. Slides were imaged using a Zeiss LSM 880 microscope, and analyzed using the ImageJ "FIJI" or Imaris softwares. Human brain tissue slices were further incubated with TrueBlack for five minutes prior to mounting, to reduce auto-fluorescence.

Transmission Electron Microscopy.

Animals were anaesthetized via exposure to gaseous isoflurane. The head was submerged under EM-grade fixative, and the brain removed without exposure to air. The corpus callosum was dissected out, and post-fixed in EM-grade fixative for 72 hours. Tissue preparation and transmission electron microscopy was performed at the Harvard TEM core.

Western Blot.

Protein concentration of each sample was measured using the Bradford Protein Assay. Volumes corresponding to 50 μg of protein for each sample were loaded into wells, and a current of 100V was applied for 45 minutes. The gel was transferred to a membrane for 30 minutes, blocked in 3% milk in TBST for two hours at room temperature, and incubated with primary antibody overnight at four degrees. Membranes were washed with TBST, incubated with an antibody-conjugated horseradish peroxidase for two hours at RT, and a chemiluminescence activator.

Cyclodextrin Treatment.

APOE4KI female mice were injected subcutaneously with either 200 µL Cyclodextrin (2 g/kg) or 200 µL saline, twice a week for eight weeks.

Novel Object Recognition Task.

Mice were placed in an open field arena and allowed to move freely for ten minutes. The total distance moved and time mice spent in the center of the arena was tracked using the EthoVision XT software from Noldus. 24 hours later, mice were then placed into the same arena containing two objects and allowed to freely investigate both for a period of eight minutes. After an interval of four hours, mice were then placed back in the chamber with one novel object and one familiar object. The preference index was calculated by determining how much time an animal spent with its nose interacting with the novel object, divided by the total time an animal spent interacting with either object.

Example 2. Lipid Accumulation Induced by APOE4 Impairs Microglial Surveillance of Neuronal-Network Activity Introduction Although many glia cell-types may modulate and sculpt neuronal circuits, it is unclear how disease-associated genetic drivers enriched in glia, such as single nucleotide polymorphisms (SNPs), impact neuronal network dynamics. As brain-resident macrophages, microglia are highly reactive to disturbances within the brain microenvironment. This imposes limitations on the viral techniques that are typically employed in systems neuroscience to assess neuron-microglia communication. While the generation of transgenic mouse models harboring disease-associated alleles circumvents this technical challenge, the rapid pace of human genomic studies far outpaces the low throughput nature of deriving transgenic murine lines. This underscores the need for the development of human-based models to interrogate disease-associated genomic variants in complex multicellular platforms. Furthermore, these systems must be tractable for genome editing with reproducible phenotypic read-outs. Cellular studies utilizing patient-derived induced pluripotent stem cells (iPSCs) to examine the bi-directional communication between neurons and glia with iPSCs are still lacking. Using CRISPR-edited APOE isogenic cell lines, it was possible to test the impact of AD-associated variants on the cellular communication between neurons and microglia using an iPS-based platform.

Results iPSC-derived Microglia-like Cells (iMGLs) Respond to Soluble Factors Secreted by Neurons in an Activity-Dependent Manner. Purinergic signaling is a powerful modulator of microglia chemotaxis, phagocytosis, and pro-inflammatory cytokine production. Within the brain, the purinergic receptor P2RY12 is highly and predominantly expressed by microglia, allowing for microglia to rapidly sense extracellular adenosine di- or tri-phosphate (ADP or ATP) secreted by neurons under physiological (i.e. co-released with neurotransmitters) or pathological conditions (i.e. upon infliction of cellular damage). In addition, many soluble neuronal factors maintain microglia in an inactivated surveillance state, such as the CX3CL1-CX3CR1 signaling axis. Interestingly, microglia also express numerous neurotransmitter receptors, including glutamate receptors such as AMPA, NMDA and mGLURs, suggesting that microglia can sense glutamatergic neuronal communication. We sought to determine if microglia derived from iPSCs expressed receptors thought to mediate neuron-microglia communication. We began by generating iMGLs using established protocols that have been characterized to yield cells of similar transcriptional composition to microglia isolated from human brains. After 4 weeks of differentiation from iPS-derived primitive hematopoietic progenitors, iMGLs in culture exhibited ramified morphology, stained positive for microglial specific-markers such as IBA1 and P2RY12, and displayed mature electrophysiological properties typical of ex vivo microglia in culture via whole cell patch-clamp analysis. Additionally, immunostaining of iMGLs revealed the expression of canonical ion channels P2X1 and THIK-1, critical regulators of microglial homeostasis. We also detected expression of the voltage-gated potassium channel KCNE3, and the voltage-gated calcium channel CACNA2D4, in addition to the metabotropic glutamate receptor, GLUR7. Collectively these findings suggest that iMGL recapitulate expression patterns of receptors governing surveillance of neuronal activity.

To better characterize the functional properties of these transmembrane channels, we examined calcium signaling in iMGLs in response to extracellular cues. Receptor-mediated $Ca^{2+}$ signals are a common transduction mechanism in microglia, particularly downstream of ligand-gated calcium-permeable purinergic receptors. In addition, the activation of metabotropic receptors is known to trigger the release of intracellular $Ca^{2+}$ stores in microglia, making calcium imaging an attractive tool to examine microglial response to neuronal soluble cues. Given microglia response to viral infections, we reasoned that non-viral mediated approaches to visualize calcium transients may be better suited to avoid evoking microglial activation. Thus, we labeled monocultures of iMGLs with the membrane-permeant calcium indicator, Fluo-4 AM. At baseline, we observed sparse microglial calcium transients, which were characterized by their high amplitude (greater than 1 $\Delta F/F$; change in fluorescence over baseline) and prolonged periods (nearly 4 minutes in duration). Since iMGLs have been shown to respond in culture to extracellular ATP and ADP in a P2RY12-dependent manner, we next attempted to evoke calcium transients by pharmacologically exposing iMGLs to ATP. We used a biologically inactive analog of ATP that can be photostimulated with ultraviolet light for rapid activation (Caged ATP Vs. Uncaged ATP) to track the cellular response of the same cell over the course of 10 minutes. ATP uncaging elicited a robust increase in calcium transients in iMGLs. In addition, we also determined that iMGLs sensed extracellular ATP with whole-cell patch-clamp analysis. Since microglia are known to respond to excitatory neurotransmitters in vivo (Eyo et al., 2014), we sought to determine if calcium transients in iMGLs were elevated upon glutamate exposure. Using a similar drug application strategy to caged-ATP, we found that uncaging NMDA, an amino acid derivative that acts as an NMDA receptor agonist, or glutamate, both increase the amplitude of calcium transients, suggesting that iMGLs may sense secreted neuronal soluble factors, such as nucleotides or neurotransmitters.

To test the possibility that iMGLs could respond to a more physiological neuronal stimulus, we next generated forebrain spheroids that were mainly composed of excitatory neurons. Spheroids are smaller in size than brain organoids (only 1-2 mm in diameter) and circumvent the nutrient-poor inner core of large organoids that result in necrotic hotspots. Extended culture times of greater than 120 days yield a small, but growing population of GFAP-positive astrocytes amongst MAP2-positive neurons. Although astrocyte-derived soluble cues have been shown to be critical signaling nodes of the brain microenvironment, we exclusively conducted our studies on spheroids between 60-90 days to restrict our findings to neuronal factors. Since a high level of neuronal activity is associated with a larger number and higher amplitude of microglial calcium transients in vivo, we postulated that pacing spheroids with electrical pulses would stimulate greater release of neuronal soluble factors. We adapted paddle carbon electrodes built onto a tissue culture multi-well plate typically employed over the course of several days to enhance the maturation of iPSC-derived cardiomyocytes. To optimize the pacing of spheroids, we infected 3D cultures with Adeno-Associated Virus (AAV) carrying the genetic calcium indicator GcaMP6f under the neuron-restricted synapsin promoter (AAV pSYN-GcaMP6f). Penetration of AAV into these cultures successfully labeled a subset of surface level neurons. Stimulation with paddle electrodes evoked a robust and sustained neuronal response as quantified by the change in pre-stimulation vs. the post-stimulation GCaMP fluorescence.

To determine if iMGLs responded to neuronal secreted factors in an activity-dependent manner, we performed media carry-over experiments in four experimental groups. Unspent neuronal media evoked no response in iMGLs after 2 hours of incubation, while neuronal media conditioned for 24 hours with forebrain spheroids significantly increased the number of calcium transients, as indicated by the elevated mean amplitude in $\Delta F/F$. When we treated iMGL with conditioned media from spheroids that had been stimulated with paddle electrodes for 1 hour, we observed increased calcium transients of iMGLs. Importantly, when the stimulation was performed in the presence of tetrodotoxin (TTX), a potent inhibitor of neuronal activity, the increase in iMGL calcium transients mediated by stimulated spheroid media was reduced to levels of non-stimulated spheroid media. To avoid carrying-over TTX to the microglia, stimulation was followed by three washes in warm media and a complete media switch free of TTX that was allowed to condition for 24 hours. Non TTX-treated stimulated controls were handled identically to control for drug washout manipulation. Collectively, these experiments demonstrate that iMGLs can sense neuronal soluble cues in an activity-dependent manner and establish an experimental platform to interrogate the impact of AD-associated risk factors on neuron-microglia cellular communication.

Modeling Neuron-Microglia Communication with CRISPR-Edited APOE3 and APOE4 iMGLs.

We envisioned that combinatorial experiments mixing and matching forebrain spheroids and iMGLs derived from CRISPR-edited isogenic iPSC lines harboring either APOE3 or APOE4 alleles could be a powerful approach to determine the functional impact of APOE4 on neuron-microglia communication. iMGLs were generated from APOE3 and APOE4 iPSCs and characterizing their calcium transients with Fluo-4 AM. At baseline, we did not observe any differences in the levels of spontaneous calcium transients between genotypes. To determine if iMGLs responded differently to application of neuronal soluble factors, we applied APOE3 spheroid conditioned media (CM) to monocultures of APOE3 or APOE4 iMGLs and measured calcium transients over the same recording window. Interestingly, neuronal conditioned media evoked fewer calcium transients in APOE4 than APOE3 iGMLs. In addition, upon ATP uncaging, APOE4 iMGLs displayed a blunted response compared to APOE3 iMGL controls. iMGLs derived from a distinct donor parental line showed similar responses suggesting that this phenotype is independent of isogenic cell line derivation. Although the blunted response observed in APOE4 iMGLs exposed to neuronal CM could indicate a deficit in a number of signaling systems, ATP uncaging experiments indicate that APOE4 iMGLs are particularly impaired in purinergic signaling. These results suggest that APOE4 iMGLs are weakly attuned to neuronal activity. Moreover, given that downregulation of purinergic receptors, namely P2RY12, is associated with microglial activation status, we reasoned that homeostatic surveillance state is shifted in APOE4 iMGLs.

Neuronal Conditioned Media Evokes Distinct Transcriptional Responses in APOE3 Vs.

APOE4 iMGLs. We probed the transcriptional profile of these cells at baseline and in response to spheroid conditioned media. After 4 weeks in culture, APOE3 or APOE4 iMGLs pre-conditioned in unspent neuronal media for 24 hrs were further incubated with spheroid conditioned neuronal media for 2 hours. Cells were lysed and harvested for RNA extraction, library preparation and bulk sequencing. Biological triplicates were analyzed for 4 groups: APOE3 vs APOE4 iMGLs with or without exposure to APOE3 spheroid conditioned media (+CM). Principal component analysis (PCA) revealed that samples clustered most by genotype and conditioned media exposure. Comparison of APOE3 to APOE4 iMGLs revealed 4,167 differentially expressed genes (DEGs) (APOE3 vs APOE4 iMGLs; False Discovery Rate (FDR) corrected p-value<0.05).

To understand how spheroid conditioned media affects iMGL transcription at baseline, we first performed differential analysis comparing APOE3 to APOE3+CM. We identified 604 downregulated and 884 upregulated DEGs in APOE3+CM iMGLs. Gene ontology (GO) analysis of CM-evoked transcripts in APOE3 iMGLs revealed a strong signature of secondary signaling cascades including cAMP signaling (FDR $7.19 \times 10^{-3}$), Phospholipase D signaling (FDR $9.14 \times 10^{-4}$), MAPK signaling (FDR $1.33 \times 10^{-4}$) and the regulation of actin cytoskeleton (FDR $1.29 \times 10^{-2}$). In fact, one of the most highly enriched genes induced by conditioned media was the cAMP response element modulator, CREM (APOE3 vs. CM; FDR $4.08 \times 10^{-67}$). Increased cAMP-mediated signal transduction in microglia is associated with the rapid generation of actin-dependent filopodia which allows for fast nanoscale surveillance within discrete regions of the brain parenchyma. In contrast, APOE4 iMGL exposure to spheroid conditioned media evoked a larger transcriptional response with 1,305 down and 1,702 upregulated DEGs. APOE4+CM iMGLs were significantly enriched for HIF-1 signaling (FDR $2.26 \times 10^{-2}$), JAK-STAT signaling (FDR $2.15 \times 10^{-2}$), Cytokine-cytokine receptor interaction (FDR $2.59 \times 10^{-3}$), and Phagosome (FDR $1.54 \times 10^{-3}$) suggesting a strong pro-inflammatory response. Similar to APOE3 iMGLs however, spheroid conditioned media also evoked upregulation of cAMP-mediated transcripts in APOE4 iMGLs, including CREM, although to a lesser extent. In fact, we observed decreased induction of several targets of intracellular $Ca^{2+}$ signaling in APOE4 iMGLs+CM in direct comparison to APOE3 iMGLs+CM, including calmodulins (e.g. CALM2 and CALM3), mitogen-activated protein kinases (e.g. MAPK1 and MAPK9), and calcium/calmodulin-dependent protein kinases (e.g. CAMK2D and CAMK1), congruent with our observation of decreased calcium transients in APOE4 iMGLs in spheroid conditioned media.

Our initial differential expression analysis revealed that both APOE3 and APOE4 iMGLs upregulate Ca2+ signaling pathways in response to spheroid conditioned media, although this pathway enrichment is muted in APOE4 iMGLs. Additionally, APOE4 iMGLs seem to activate more inflammatory pathways in response to spheroid conditioned media than APOE3 iMGLs. To further dissect the differences between APOE3 and APOE4 iMGLs in response to conditioned media, we directly compared their transcriptional profiles (APOE3+CM vs. APOE4+CM). Emerging genetic mechanisms have linked the mobilization of intracellular $Ca^{2+}$ with downstream lipid signaling, particularly through the induction of lipid secondary messengers such as phosphatidylinositol 3-kinases (PI3Ks). In microglia, PI3K-AKT signaling regulates many cellular functions, including the production of cytokines in response to pro-inflammatory stimuli. Although we detected moderate enrichment of the PI3K-AKT signaling pathway in APOE3 iMGLs exposed to spheroid conditioned media (APOE3 vs. APOE3+CM), we observed a comparable increase in the induction levels of AKT serine/threonine kinase 1 (AKT1) in APOE4 iMGLs+CM in comparison to APOE3 iMGLs+CM. Regarding the relationship between calcium influx and lipid signaling is the upregulation of ARL4C (Also known as ARL7), the most overall enriched DEG we identified in CM-evoked transcripts in APOE3 ($Log_2$ fold-change=1.87, FDR $4.05 \times 10^{-71}$) and even more so in APOE4 ($Log_2$ fold-change=2.43, FDR $6.20 \times 10^{-191}$). The ADP-ribosylation factor-like 4C or ARL4C, is a direct target induced by the activation of liver X receptor (LXR) and has been shown to transport cholesterol to the membrane for ABCA1-associated removal in macrophages. The results implicate lipid metabolic and inflammatory gene programs in the response of iMGLs to conditioned media.

To dissect the regulatory landscape that governs the distinct lipid metabolic and inflammatory transcriptional response by APOE4 iMGLs to spheroid conditioned media, we identified transcription factors (TFs) significantly enriched in either APOE3 iMGLs, APOE4 iMGLs, or both genotypes upon exposure to spheroid conditioned media. Commonly evoked TFs included several master regulators of inflammation, including the nuclear factor kappa B subunit 1 (NFKB1), and the signal transducer and activator of transcription 4 (STAT4). We observed a distinct set of inducible TFs that bifurcated on the known role to mitigate or exacerbate inflammatory processes in a genotype-dependent manner. For instance, neuronal media induced expression in APOE3 iMGLs of the proto-oncogene CBL which has been shown to repress pro-inflammatory activation pathways in immune cells, and also PRDM1 (Positive Regulatory Domain 1, also known as BLIMP1) which was identified as a repressor of interferon gene expression, with depletion of PRDM1 being associated with aberrant and exacerbated activation of inflammatory reactions. The induction of these inflammatory repressors by APOE3 iMGLs (i.e. CBL, PRDM1 and ELKS) in response to spheroid conditioned media may act as an immune checkpoint to mitigate downstream inflammatory responses despite the induction of immune master regulators. Failure to evoke these inducible-TFs suggests that this immune checkpoint is left unchecked in APOE4 iMGLs, perhaps leading to overactivation of downstream immune effectors. Although our data suggests that APOE3 and APOE4 iMGLs responded similarly to changes in their microenvironment (i.e. acute exposure to neuronal soluble cues), we observed a dichotomy in the execution of inflammatory responses between APOE4 and APOE3 iMGLs.

Microglial activation is defined by dramatic changes to cell morphology and to purinergic signaling. Since our assays indicated that the capacity of APOE4 iMGLs to sense ATP or broader neuronal-secreted soluble factors were decreased, we next examined the levels of P2RY12 across APOE3 and APOE4 iMGLs. APOE4 iMGLs expressed significantly lower levels of P2RY12 than APOE3 iMGLs. While exposure to spheroid conditioned media for 2 hours significantly decreased levels of P2RY12 in both genotypes, P2RY6 expression levels increased only in APOE3 iMGLs. Upregulation of P2RY6 in microglia is associated with a hypervigilant microglial activation state that acts as a primer for the phagocytosis of dead cells or debris. Interestingly, despite these deficits in purinergic receptor expression, APOE4 iMGLs dramatically increased the expression levels of adenosine receptor A2A (encoded by the gene ADORA2A). In the brain, ATP can be rapidly hydrolyzed into adenosine which is a potent activator of microglia pro-inflammatory phenotype. Upregulation of A2A receptor is associated with the shift from ramified to amoeboid microglial morphology during brain inflammation. In agreement with this observation, we detected a reduction in multiple homeostatic microglia genes, including CX3CR1 and CSF1R which have been reported to be downregulated in activated microglia.

Microglial Energetics and Lipid Processing are Altered in APOE4 iMGLs.

We sought to identify the cellular mechanism by which APOE4 genotype shifts microglial status away from homeostatic surveillance. At baseline and upon spheroid conditioned media, we observed a dramatic decrease in DEGs relating to mitochondrial oxidative phosphorylation (OXPHOS) in APOE4 iMGLs. Deficits in mitochondrial metabolism that yield a low energy cellular state have been previously reported in APOE4 human subjects, as well as in mice and iPSC-derived glia harboring APOE4 alleles. It was observed that a small but significant upregulation of the glucose transporter GLUT3 in APOE4 iMGLs ($Log_2$ fold-change=0.37, FDR 0.0315), while GLUT1 dramatically increased in expression ($Log_2$ fold-change=6.01, FDR $1.67 \times 10^{-23}$) relative to APOE3 iMGLs. The upregulation of GLUT1 in pro-inflammatory microglia increases glucose uptake and promotes glycolysis. Moreover, through our transcriptional analysis we observed that HIF-1 signaling is enriched in APOE4 iMGLs. HIF-1α is a master transcriptional regulator of glycolysis, and is induced by AKT through phosphorylation of mammalian target of rapamycin (mTOR). Metabolic reprogramming of microglia from OXPHOS to glycolysis by pro-inflammatory stimuli is dependent on the AKT-mTOR-HIF-1α pathway. These results suggest that APOE4 expression in microglia induces a metabolic reprogramming in energy production that is associated with a pro-inflammatory state.

Mitochondrial oxidation of free fatty acids is a critical mechanism by which lipids are broken-down as energy substrates. Energy depletion and impairment of fatty acid oxidation has been associated with intracellular lipid accumulation in activated microglia. As such, concurrent with downregulation of genes related to OXPHOS, we also observe a dramatic decrease in DEGs related to lipid catabolic processes in APOE4 iMGLs in relation to APOE3, independent of conditioned media application. Moreover, we also detected a significant downregulation of the membrane fatty-acid transporter CD36 (Also known as FAT) in APOE4 iMGLs in comparison to APOE3 iMGLs. Since the uptake of fatty acids are associated with its metabolic demand to fuel lipid oxidation, our transcriptional profiling reveals a molecular program leading to the accumulation of lipids via disrupted mitochondrial function. Interestingly, upon exposure to neuronal conditioned media we further detected the differential upregulation of a subset of genes in APOE4 iMGLs involved in the de novo production of lipids or in the regulation of its cellular storage, with the Acyl-Coa synthethase ACSL1, showing the most robust enrichment. We determined the abundance of intracellular lipids in APOE4 iMGLs, as well as their ability to buffer, or uptake, extracellular free fatty acids. Indeed, staining for intracellular neutral lipid stores known as lipid droplets with the fluorescent dye BODIPY (counter stained with the microglia-specific marker IBA1) reveals significantly greater lipid droplet content in APOE4 iMGLs in comparison to APOE3 iMGLs. In addition, incubation of iMGLs with the green-fluorescent fatty-acid Cu BODIPY (C12 BODIPY) reveals decreased uptake by APOE4 iMGLs, indicative of a functional deficit in fatty acid uptake.

In addition to fueling lipid oxidation, fatty acid uptake by glia is particularly important in preventing neurodegeneration. Neurons have minimal capacity to catabolize fatty acids or store lipids and therefore rely on glial mitochondrial oxidation for lipid consumption by transferring fatty acids via APOE-associated particles. Interestingly, the metabolic coupling of neurons and astrocytes is disrupted by APOE4 leading to impaired neuronal synaptic maturation. Although metabolic coupling with neurons have been predominantly studied in the context of astrocytes, microglia and astrocytes have both been shown to accumulate lipid droplets in vivo upon neuronal excitotoxic injury. Yet, the functional repercussions of a lipid burdened microglial state to the activity of neuronal circuits remains unknown.

APOE4 Microglia Impair the Highly Coordinated Neuronal Activity of APOE3 Spheroids.

It remains unclear if disease-associated genetic risk variants expressed by microglia disrupt the cellular processes. To assess how APOE4 iMGLs impact the activity of neurons, we began by dissociating spheroids grown in 3D after 60 days into a single-cell suspension and plating these cultures onto coverslips. After 4 weeks in culture, we found that dissociated spheroids displayed mature neuronal morphology with extensive neurite networks in 2D and were free of GFAP-positive cells. Dissociated spheroids were efficiently infected by AAV virus as shown by the expression of EGFP under the neuronal specific promotor Synapsin (AAV pSynapsin-EGFP) 2 weeks post-transduction. This is contrary to previous observations in 3D spheroids where successful viral transduction was limited to a small population of neurons near its outer surface. To track microglia in mixed cultures with neurons, we pre-labeled iMGLs with the microglia-specific dye Isolectin IB$_4$). We found that iMGLs persisted in these mixed cultures for at least 4 weeks, with a subset of these cells adopting highly ramified morphologies shown by immunostaining with the microglial marker IBA1

We next derived cortical spheroids and iMGLs in parallel from APOE3 or APOE4 isogenic iPSCs for combinatorial experiments to mix and match APOE genotypes. Dissociated spheroids from APOE3 or APOE4 were transduced with AAV pSyn-GCaMP6f for 2 weeks, and calcium dynamics visualized. We observed vastly different baseline calcium dynamics between APOE3 and APOE4 neurons; while APOE3 neurons displayed highly synchronous network events, calcium transients in APOE4 neurons were asynchronous and more frequent. Given the critical role of microglia in sculpting neural dynamics, we sought to determine the impact of APOE4 iMGLs to neuronal network activity. Isolectin-labeled APOE3 or APOE4 iMGLs were seeded with distinct cultures of APOE3 dissociated spheroids that had been pre-labeled with AAV pSyn-GCaMP6f prior to co-culture. By quantifying spontaneous calcium events of APOE3 neurons in co-culture for 1 week with either APOE3 or APOE4 iMGLs, we found that APOE4 iMGLs decreased the overall number of calcium transients in APOE3 spheroid cultures. Additionally, we observed that APOE4 iMGLs disrupted coordinated neuronal ensemble events in APOE3 neurons, as quantified by the number of spontaneous calcium transients with greater than 60% co-active cells. We did not detect differences in the number of synapses via immunostaining or Western blotting for the pan-presynaptic marker, synaptophysin, after 1 week of co-culture. Since we observe changes to neuronal calcium dynamics at a point in which we do not detect robust changes to synaptic number, we postulated that a non-phagocytic mechanism may mediate the contribution of APOE4 iMGLs to impaired neuronal network dynamics.

Imbalance in the Net Flux of Lipids by APOE4 iMGLs.

Microglia secrete a vast array of immunological factors that can modulate the survival and proliferation of cells residing in neurogenic niches. To investigate if microglial secreted factors impact neuronal activity, we next decided to conduct media carry-over experiments from APOE3 or APOE4 iMGL monocultures to APOE3 spheroid cultures labeled with AAV pSyn-GCaMP6f. iMGLs were incubated in unspent neuronal media for 24 hours before media was collected to ensure media carry-over would be the least disruptive to neuronal cultures, and neurons were then allowed to incubate in iMGL conditioned media for an additional 24 hours. We observed a robust decrease in neuronal calcium transients in cultures that were exposed to APOE4 iMGL conditioned media, while cultures treated with APOE3 iMGL conditioned media continued to display highly synchronized calcium transients. The magnitude of the neuronal activity suppression appeared to be much larger than prior studies. This might be potentially due to the acute nature of the experimental design, as neurons in co-culture with microglia for several days may adapt to enriched microglial-secreted factors by modulating the expression of surface receptors. Nevertheless, we reasoned that we could take advantage of this system to dissect the mechanism by which APOE4 iMGLs differentially impact neuronal activity.

Our transcriptional profiling revealed a dramatic difference in lipid metabolism between APOE3 and APOE4 iMGLs that was associated with an activated state distinct from homeostatic surveillance. As the major transporter of cholesterol in the brain, APOE mediates the delivery of cholesterol and other lipids between neurons and glia. Thus, we decided to examine levels of APOE and cholesterol in the supernatant of APOE3 and APOE4 iMGL monocultures. We found that the supernatant of APOE4 iMGL cultures were enriched in both APOE and cholesterol in relation to APOE3. We repeated this experiment using the fluorescent cholesterol analog BODIPY-cholesterol, which also revealed an increase in cholesterol in the media of APOE4 iMGL. Extracellular lipid accumulation could also be the net product of a relatively greater deficit in lipid influx. To test this idea, we exposed APOE3 or APOE4 iMGLs to low-density lipoprotein (LDL) isolated from human plasma. Along with APOE, lipoproteins like LDL make up the structural outer surface of lipid cores that are secreted from glia and transported to neurons via lipoprotein binding receptors. We observed a dramatic reduction in cellular uptake of LDL by APOE4 iMGLs in comparison to APOE3 controls. These results are consistent with our transcriptional profiling, in which the low-density lipoprotein receptor (LRP1) is significantly down-regulated in APOE4 iMGLs. We concluded that extracellular lipid accumulation is likely a reflection of a greater impairment in lipid influx than efflux in APOE4 iMGLs already burdened by high intracellular lipid content.

To define how microglial lipid metabolism might regulate neural network dynamics, we next turned to neurons seeded onto multielectrode arrays (MEA). Seeding intact APOE3 spheroids onto MEAs yielded a robust readout of neuronal activity. Exposing intact APOE3 spheroids to APOE4 iMGL conditioned media for 24 hours significantly decreased the overall number of neuronal spikes and bursts relative to cells exposed to APOE3 iMGL conditioned media. Interestingly, APOE3 spheroids can partially recover after withdrawal of APOE4 iMGL conditioned media, suggesting neuronal activity is actively suppressed by soluble factors in the media.

Neuronal Accumulation of Cholesterol-Enriched Membrane Microdomains Modify K+ Currents.

Cholesterol is essential for proper neuronal physiology, and cholesterol depletion is known to impair neurotransmission. Since we detect extracellular accumulation of cholesterol in APOE4 iMGLs, we wondered what the impact of exogenous cholesterol treatment would be to these neuronal cultures. Due to the extended culture times of spheroids, we opted to conduct these studies with excitatory neurons generated by the rapid induction of NGN2 expression. Treatment of neurons seeded onto MEAs with water-soluble cholesterol phenocopied our observation of treatment with APOE4 iMGL conditioned media. To further dissect the physiological process that renders neurons less excitable upon treatment with exogenous cholesterol, we next assessed iPSC-derived neurons by patch-clamp electrophysiology. We decided to do this work with dissociated spheroid cultures since they displayed mature neuronal calcium dynamics, perhaps due to the extended culture time in 3D before dissociation. Indeed, current-clamp and voltage-clamp recordings demonstrated physiological properties akin to mature neurons in these cultures. We found that addition of exogenous cholesterol significantly hyperpolarized the resting membrane potential (RMP) of cholesterol-treated neurons. Moreover, we also observed a change in the I-V (Current-Voltage) curve of non-treated versus cholesterol treated neurons, indicative of greater inwardly-rectifying potassium ($K_{ir}$) currents. Potentiation of $K_{ir}$ currents is aligned with our observation in cells recorded on MEA, as strong inwardly-rectifying potassium currents are known to hyperpolarize resting membrane potentials and decrease neuronal excitability. In fact, overexpression of the inwardly-rectifying $K^+$ channel, $K_{IR}2.1$, has been used extensively in neuroscience to genetically inhibit neuronal activity.

Nevertheless, members of the $K_{ir}$-family of channels span across 7 subfamilies ($K_{ir}$1-7), and their expression and function remain uncharacterized in forebrain spheroids. We decided to isolate mRNA from APOE3 spheroids and APOE3 spheroids exposed to APOE4 iMGL conditioned media for 24 hours for bulk RNA-sequencing to define the expression of $K_{ir}$ channels. We detected transcripts for 14 out of the 15 annotated genes that encode $K_{ir}$ channel members in our forebrain spheroids, with the most abundantly expressed member being $K_{ir}3.3$ (encoded by the gene KCNJ9). $K_{ir}3.3$ is a G protein-gated inwardly rectifying $K^+$ channel (GIRK3) that regulate neuronal excitability similarly to other $K_{ir}$ channels, with gain of function reducing neuronal activity and loss of function increasing neuronal activity. Notably, GIRK channels are known to be lipid-gated as K+ flux is dependent on binding of the phospholipid phosphatidylinositol (4,5)P2 (PIP2). Based on our RNA-seq analysis, APOE4 iMGL conditioned media significantly upregulated transcript levels of GIRK3 in spheroids, while GIRK1, GIRK2 and GIRK4 remained unchanged. To determine if GIRK3 upregulation was APOE genotype-dependent, we next assessed expression of GIRK3 in APOE3 spheroids exposed to either APOE3 or APOE4 iMGL conditioned media by immunostaining. Protein levels of GIRK3 (normalized for total neuronal content imaged with the pan-neuronal marker TUJ1) was significantly increased in spheroid neurons treated with APOE4 iMGL conditioned media, suggesting greater surface expression levels. Interestingly, GIRK channels are known to localize to cholesterol-rich microdomains at neuronal membranes, often referred to as lipid rafts. It is thought that localization of receptors to lipid rafts can influence the potency of receptor-activated signaling cascades. Congruent with our observation of increased GIRK3 in neurons treated with APOE4 iMGL conditioned media, we detect an increased prevalence of cholesterol-rich lipid rafts in contrast to neurons treated with APOE3 iMGL conditioned media.

To determine if the potentiation of GIRK3 is necessary for the suppression of neuronal activity in APOE4 iMGL conditioned media treated cultures, we next targeted GIRK3 with CRISPR-interference (CRISPRi). We derived spheroids from iPSCs edited to harbor a catalytically dead CAS9 (dCAS9) fused to the transcriptional Kruppel-associate box (KRAB) repressor within the safe harbor locus, CLYBL. Gene repression in iPSC-derived neurons with this CRISPRi vector has been previously reported, and iPSC line edited to carry this construct was acquired from the Allen Institute Cell Collection. We determined the APOE genotype of this iPS donor to be homozygote for APOE3 in-house. Neurons derived from these cultures were seeded onto MEAs and transduced with a lentiviral vector carrying sgRNA and a red fluorescent protein tag (TagRFP). APOE3 neurons infected with a lentiviral pool of 3 distinct sgRNAs targeting KCNJ9 (Gene that encodes GIRK3) after 3 weeks were exposed to APOE4 iMGL conditioned media. We determined by qPCR for KCNJ9 that this viral pool repressed KCNJ9 expression by 66%±13.9% S.E.M relative to control (vector free of targeting sgRNAs was used as control). Interestingly, we observed that GIRK3 knock-down prevented the repression of neuronal bursts by APOE4 iMGL condition media. Of note, we did not observe a significant rescue in the number of spikes between GIRK3 knock-down and control (unpaired t-test, p-value=0.1758), suggesting GIRK currents may be particularly important to regulate neuronal burst firing properties as previously demonstrated to be the case in pacemaker neurons. Collectively, these results demonstrate that extracellular cholesterol accumulation, at least in part due to poor lipid re-uptake by APOE4 iMGLs, can suppress neuronal activity via potentiation of GIRK currents.

Modulation of Intracellular Lipid Content can Reversibly Drive Purinergic Signaling in Microglia.

To determine if APOE4-induced lipid accumulation is necessary and sufficient to drive microglia activation status away from homeostatic surveillance, we attempted to bidirectionally modulate lipid content in APOE3 or APOE4 iMGLs. We began by inducing lipid droplet accumulation in APOE3 iMGLs by exposing the cells to the mono-unsaturated fatty acid, oleic acid (OA) for 16 hours. Fatty acid overload is a potent inducer of lipid droplet formation, and as such IBA1-positive cells treated with OA accumulated intracellular BODIPY-positive lipid droplets. The rise in lipid droplet content was also linked with a decrease in the cell size of iMGLs, which resembles ameboid-like morphologies adopted by activated microglia. In fact, profiling OA-treated iMGLs by qPCR for the pro-inflammatory MHC-II marker, CD74, reveals upregulation of this gene which more closely resembled basal levels observed in non-treated APOE4 iMGLs. To determine if OA-treated iMGLs exhibited deficits in purinergic signaling that phenocopied APOE4 iMGLs, we turned to calcium imaging upon ATP uncaging. OA treatment was sufficient to blunt calcium transients evoked by ATP uncaging relative to untreated APOE3 iMGLs. A key mechanism mediating lipid storage into intracellular droplets is the activation of fatty-acids by the Acyl-Coa synthethase, ACSL1. ACSL1 expression has been reported to be modulated by lipogenic conditions, and as such we observed that OA significantly induced the expression of ACSL1. This is of particular interest, since we also uncovered ACSL1 as the most enriched gene governing lipogenesis in APOE4 iMGLs through our RNA-seq analysis. Collectively, these results suggest that increasing lipid accumulation is sufficient to shift microglia away from homeostatic surveillance, and phenocopies key aspects of the APOE4 iMGL state.

Having induced lipid formation in APOE3 iMGLs, we next attempted to deplete APOE4 iMGLs of lipid droplets to test whether this would alleviate APOE4 phenotypes. We turned to the ACSL1 inhibitor Triacsin C (TrC). Treatment of APOE4 iMGLs with TrC for 16 hours was sufficient to dramatically reduce BODIPY-positive lipid droplets relative to DMSO-treated control cells. Furthermore, purinergic signaling was restored after lipid droplet depletion in APOE4 IMGLs. Since TrC has also been reported to inhibit cholesterol biosynthesis and increase microglial phagocytosis, we decided to test if the extracellular accumulation of cholesterol in APOE4 iMGLs could be reduced by TrC treatment. After 16 hours, DMSO-treated controls or TrC-treated APOE4 iMGLs were washed off the drug treatment and allowed to condition the media for an additional 24 hours. Indeed, we observed a significant decrease in the levels of accumulated cholesterol in the media via ELISA. We reasoned that a decrease in extracellular cholesterol accumulation in APOE4 iMGLs cultures treated with TrC was likely to also relieve the suppression of neuronal activity under APOE4 iMGL conditioned media. NGN2-induced neurons from APOE3 or APOE4 iPS lines were seeded onto MEAs and allowed to mature for 3 weeks before being recorded 24 hours after exposure to conditioned media from APOE3 iMGLs, APOE4 iMGLs, or APOE4 iMGL treated with TrC. While APOE4 iMGL conditioned media decreased neuronal bursts, pre-treatment of APOE4 iMGLs with TrC increased neural activity to the level of neurons treated with APOE3 iMGL media. These results establish that the maintenance of lipid homeostasis in microglia sustains surveillance homeostatic states required to support proper neuronal network function. We therefore define cholesterol metabolism as a critical link between the immunometabolism of microglia and the regulation of neuronal activity.

Methods

Cell Lines and Differentiation from iPSCs

All human iPSCs were maintained in feeder-free conditions in mTeSR1 medium (STEMCELL Technologies) on Matrigel-coated plates (Corning; hESC-Qualified Matrix) iPSCs were passaged at 60-80% confluence using ReLeSR (STEMCELL Technologies) and reseeded 1:6 onto Matrigel-coated plates. APOE isogenic lines derived from a 75 year old female (AGO9173) with APOE3/3 genotype edited to harbor APOE4/4. A second distinct APOE isogenic line was derived from a 70 year old female sporadic AD patient (AG10788) with APOE4/4 genetoype (sADE4/4) and CRISPR-edited to APOE3/3 (sADE3/3). The iPSC lines were generated by the Picower Institute for Learning and Memory iPSC Facility. CRISPRi iPSCs were acquired via the Allen Institute for Cell Science https://www.allencell.org, and maintained similarly as described above. APOE genotype for the CRISPRi line was determine by amplifying the APOE locus.

Spheroid Induction Protocol

Dorsal forebrain spheroids were generated using an adapted iPS seeding strategy. Briefly, confluent iPSCs were dissociated into a single-cell suspension after incubation in ReLeSR (STEMCELL Technologies) for 2 minutes at room temperature followed by a dry incubation at 37 C for 5 more minutes. iPSC colonies were then scraped in mTeSR1 medium (STEMCELL Technologies) and dissociated into a single-cell suspension by mechanical pipetting. Cell suspension was centrifuged at 300 g for 5 minutes, resuspended in 1 ml of mTeSR1 medium supplemented with ROCK inhibitor (Rockout, BioVision) and counted with an automated cell counter (Countess, Invitrogen). $3 \times 10^6$ cells were then plated onto microwells (AggreWell 800, STEMCELL technologies) for embryoid body induction. After 48 hours, embryoid bodies were moved onto non-tissue culture treated petri dishes (Falcon, Corning) neural induction following forebrain spheroid differentiation protocol.

Spheroid Dissociation and 2D Plating

After growing in suspension for at least 60 days, spheroids were dissociated into a single cell suspension for plating onto coverslips to generate 2D cultures. Adapting a previously described protocol, spheroids were incubated in Accutase (StemPro, Life Technologies) for 30 minutes at 37 C. Following Accutase aspiration, spheroids were mechanically dissociated by pipetting in Hank's Balanced Salt Solution containing 10% FBS (HBSS, Thermo Scientific). Cell suspension was centrifuged at 300×g, washed in warm Neurobasal media (Gibco) supplemented with B-27 (Gibco) and N-2 (Gibco) (Neuronal Media), passed through a 70 μM strainer (VWR International), and plated in 24-well Poly-D-Lysine (Sigma-Aldrich) coated No. 0 glass coverslips in 6-well MatTek plates (MatTek) at a ratio of 1 spheroid per 3 wells. Cells were allowed to recover for 1 month prior to experiments in neuronal media, half-feeding every 3-4 days.

Microglia Induction Protocol

Embryoid bodies (EBs) were generated using the same protocol as described for spheroid differentiation and seeded onto Matrigel-coated 6-well tissue culture plates at a density of 15-30 EBs per wells. EBs were first differentiated into hematopoietic progenitor cells (HPCs) using the STEMdiff Hematopoietic Kit (STEMCELL Technologies). Non-adherent HPCs were collected, centrifuged at 300×g, and resuspended in 1 mL of microglia differentiation media (MDM) containing a mixed composition of DMEM/F12 and Neurobasal (half/half) (Gibco) supplemented with IL-34 and m-CSF (Peprotech. Cells were plated in 6-well tissue culture plates at 200,000 cells per well and maintained in MDM for at least two weeks prior to use in experiments.

Microglia-Neuron Co-Cultures

Dissociated neuronal cultures were switched from Neuronal Media to BrainPhys Neuronal Medium (STEMCELL Technologies) 1 month after dissociation and prior to iMGL seeding. Neurons were infected with 12 μl of AAV9 hSYN-EGFP (Addgene #50465-AAV9) at titer $\geq 7 \times 10^{12}$ vg/mL or 12 μl AAV1 SYN-GCaMP6f-WPRE-SV40 (Addgene #100837-AAV1) at titer $\leq 1 \times 10^{13}$ vg/mL per 24 wells. Brainphys media was reduced to 300 μl overnight during transduction. The following day, fresh media was added to reach a final culture volume of 500 μL Upon harvesting and adding iMGLs, in suspension, to neuronal cultures, Brainphys was supplemented with m-CSF. Co-cultures were half-fed every 3-4 days and were ready to be used for experiments after a minimum of 1 week.

Immunofluorescence

Spheroids, dissociated neuronal cultures, and iMGLs were fixed with 4% paraformaldehyde (Electron Microscopy Sciences) at room temperature for 20 minutes followed by three washes in Dulbecco's PBS (Gibco). Spheroids were incubated in 30% sucrose overnight and imbedded in Tissue-Tek OTC (Sakura) for cryosectioning at 40 μm slices on a cryostat (Leica CM3050s). Fixed cells or slide-mounted spheroid slices were incubated with gentle agitation for 1 hour in blocking buffer (5% BSA, 1% NGS, 0.3% Triton-X in DPBS) at room temperature. Primary antibodies were incubated in blocking buffer overnight at 4 C. Secondary antibodies conjugated to Alexa-488, -555, -594, or 647 were applied at 1:1,000 for 1 hour at room temperature. Cells were incubated in Hoechst 33342 (Thermo Scientific) diluted 1:10,000 in DPBS for 5 minutes prior to mounting and imaging.

Microscopy was performed using a Zeiss LSM880 confocal system and fluorescent Z-stack images were quantified using IMARIS (Oxford Instruments).

Calcium Imaging

Live-imagining was performed with Zeiss LSM900 equipped with a heated chamber kept at 37° C. with humidity and $CO_2$ control. For Fluo-4 AM labeled iMGLs, images were acquired at 488 nm and compound uncaging done at 405 nm for 30 seconds post baseline acquisition followed immediately by post-stimulation image acquisition. For uncaging experiments, cells were pre-incubated in 1 mM Caged ATP (DMNPE-Caged ATP; Fisher Scientific #1049), 1 mM Caged NMDA (MNI-Caged NMDA; Tocris #2224) or 1 mM Caged Glutamate (MNI-Caged L-glutamate; Tocris #1490). Images were first stabilized to account for drift in the x-y direction, we used the ImageJ plugin "Linear Stack Alignment with SIFT". Calcium traces from motion-corrected time series were manually segmented on ImageJ into individual cells based on threshold intensity, variance, and upper and lower limits for cell size. Image segmentation results were separately inspected for quality control. Fluorescence signal time series ($\Delta F/F$: change in fluorescence divided by baseline fluorescence) were calculated for each individual segment whereby the baseline fluorescence for each cell was determined as the minimum fluorescence signal in baseline recording epoch. For GCaMP-tagged neurons, the onset of a calcium transient was identified as occurring when $\Delta F/F$ exceeded two standard deviations above the baseline fluorescence, and the termination of a calcium transient was identified as occurring when $\Delta F/F$ fell below 0.5 standard deviation above the baseline fluorescence. To test for changes in functional connectivity between cells in the presence of APOE3 versus APOE4 microglia, we quantified multicellular ensembles. A multicellular ensemble event was identified as occurring when the number of simultaneously active cells exceeded 60% of all cells. For neuronal calcium dynamics, data was generated from distinct cultures recorded in separate experiments and plotted as averages per group, while for iMGLs data was plotted from individual cells in one experiment, although the experiments were repeated at least three times. Heatmaps were generated using GraphPad Prism (GraphPad Software).

Electrophysiology

Whole-cell patch-clamp recordings of neurons were performed at 6 to 8 weeks after spheroid dissociation and 2D plating, or for iMGLs after 2 to 4 weeks of iMGL differentiation. Intracellular recordings were performed at room temperature using an Axon CV-7B headstage, Multiclamp 700B amplifier, and Digidata 1440A digitizer (Molecular Devices). Electrode pipettes were pulled from borosilicate glass (World Precision Instruments) on a Model P-97 Flaming/Brown micropipette puller (Sutter Instrument) and typically ranged between 4-7 MΩ resistance. Intrinsic neuronal properties were studied using the following solutions (in mM): Extracellular: 125 NaCl, 2.5 KCl, 1.2 $NaH_2PO_42H_2O$, 1.2 $MgCl_26H_2O$, 2.4 $CaCl_22H_2O$, 26 $NaHCO_3$, 11 glucose (pH 7.4). Intracellular: 135 K-gluconate, 5 KCl, 2 $MgCl_26H_2O$, 10 HEPES, 2 Mg-ATP, 0.2 $Na_2GTP$ (pH 7.2). Membrane potentials were typically kept between −50 mV to −70 mV depending on whether neurons or iMGLs were being recorded. In voltage-clamp mode, currents were recorded with voltage steps ranging from −160 mV to +80 mV. In current-clamp mode, action potentials were elicited by injection of step currents from −50 pA to +50 pA. For experiments aimed at determining the impact of cholesterol on neuronal properties, 1 mM cholesterol (Cholesterol Water-Soluble, Sigma-Aldrich #C4951) was supplemented to the external solution. ATP-evoked currents were recorded by local application of 100 μM (Sigma-Aldrich; #A9187). Data were first collected and analyzed using pCLAMP 11 software (Molecular Devices). Further analysis was done in GraphPad Prism (GraphPad Software).

Spheroid Electrical Stimulation

Culture pacing system (C-Pace EM, IONOPTIX) equipped with 6-well carbon electrode dishe (C-Dish, IONOPTIX) was used to deliver electrostimulation to spheroids at 12V with a biphasic pulse train frequency of 40 Hz. Paddle carbon electrodes were scrubbed clean with ethanol following manufacturer's recommended procedure and allowed to fully dry before use. To prevent effect of media hydrolysis, washes and full media switches immediately followed stimulation.

MEA

Dissociated spheroids or NGN2-induced neurons were plated as a 10 μl droplet in Poly-D-Lysine (Sigma-Aldrich) coated wells of a CytoView MEA 48-well plate (Axion BioSystems; M768-tMEA-48B). Typically 50,000-75,000 cells were plated per well that each contained 16 low-impedance PEDOT electrodes 50 μm in diameter and arranged at a pitch of 350 μm. Intact spheroids were plated and covered in a Matrigel droplet (Corning; hESC-Qualified Matrix) to anchor the spheroid. After 15-30 minutes in 37° C., droplets were flooded with warm Brainphys media (STEMCELL Technologies) and allowed to recover for at least 4 weeks before recording sessions. For conditioned media carry-over experiments, a recording session preceded the media treatment, denoted as baseline recording. iMGL media was added to compose half of the final volume of the well and allowed to incubate for 24 hours before a second recording was performed. All extracellular recordings were performed using the Axion Maestro Pro MEA system (Axion Biosystems). Spontaneous neural activity was recorded for 30 minutes at a sampling rate of 12.5 kHz and an adaptive threshold set at 5.5 times the standard deviation of baseline noise was used for spike detection. Bursts were detected at each electrode using an inter-spike interval (ISI) threshold set to at least 5 spikes with a maximum ISI of 100 ms. Electrodes were defined as active if neuronal firing occurred at a minimal rate of 5 spikes/min. For MEA data analysis, only wells containing a minimum of 3 active electrodes were included. Neuronal firing metrics were exported as the averages from each well from Axion Biosystems' Neural Metrics Tool and plotted with Prism Graphpad (GraphPad Software).

Drug Treatment

To block voltage-gated sodium channels, 1 µM Tetrodotoxin (Trocris, #1078) was applied to media before electrostimulation of spheroids. 20 µM Oleic Acid (Sigma-Aldrich; #03008) was applied overnight to iMGLs to induce lipid accumulation. Control cells were treated with 0.1% BSA as vehicle. 1 µM Triacsin C (Cayman Chemical; Ser. No. 10007448) was applied to iMGLs overnight to deplete lipid accumulation. Control cells were treated with DMSO as vehicle.

Western Blot

Spheroids that had been transplanted with APOE3 or APOE4 iMGLs for 10 days were washed once with cold 1×PBS and homogenized in RIPA lysis buffer (Sigma-Aldrich, #R0278) containing Halt protease/phosphatase inhibitor cocktail and EDTA (ThermoFisher, #78440). Supernatants were collected after centrifugation at 14,500 RPM for 15 min at 4° C. and stored at −80° C. for later use. Total protein levels were quantified using the Pierce BCA Protein Assay Kit (Thermo Scientific), and 5 µg of protein were loaded from each sample per lane onto precast 4-20% polyacrylamide gels (Bio-Rad, #4561094). Denatured/reduced samples were run at 150V for 75 minutes, after which proteins were transferred from the gel to 0.2 µm nitrocellulose membranes (Bio-Rad, #1704159) using the Trans Blot Turbo Transfer System (Bio-Rad) set to the mixed molecular weight program. Membranes were stained with Ponceau S (CST, #59803) and subsequently blocked with 5% non-fat milk in 1×TBST (10 mM Tris-HCl pH 8.0, 150 mM NaCl, 0.05% Tween-20) for 1 hour before incubating with primary antibody. Membranes were incubated with rabbit anti-synaptophysin (CST #36406, 1:1000) overnight at 4° C., and secondary antibody was later incubated at room temperature for 2 hours. Wash buffer was 1×TBST. Proteins were detected by WesternBright Quantum HRP substrate (Advansta, #K-12042) and visualized using the ChemiDoc MP Imaging System (Bio-Rad). Western blot densitometry was conducted using ImageJ. Synaptophysin levels were normalized to Ponceau S.

ELISA

Cholesterol levels from iMGLs in monoculture were measured using the Cholesterol Assay Kit (Abcam #ab65390) following manufacturer's instructions for fluorometric detection. Cells were grown in 6-well plates, and samples were either assayed immediately or frozen at −80° C. Celsius and thawed once for cholesterol measurements. To obtain total cholesterol levels, cholesterol esterase was added to samples. For free cholesterol measurements, samples were used directly without the addition of enzyme. Measurements were made using an EnSpire plate reader (Perkin Elmer). APOE levels were similarly processed and quantified from iMGL conditioned media using Apolipoprotein E Human ELISA kit (Invitrogen; #EHAPOE).

Lipid Cellular Assays

The fluorescently tagged cholesterol analog, BODIPY-Cholesterol (Cholesterol with BODIPY at carbon-24 of the side chain) (Cayman Chemical; #24618) was used to assay the extracellular accumulation of cholesterol in monocultures of APOE3 or APOE4 iMGLs. Cells were incubated with BODIPY-Cholesterol for 48 hours to saturate cellular uptake, washed 3 times and further incubated for an additional 24 hours before media was collected, centrifuged at 300 g for 5 minutes and assayed for fluorescence at 488 nm with EnSpire plate reader (Perkin Elmer). Low Density Lipoprotein (LDL) from human plasma complexed to pHrodo red (pHrodo-LDL) (Invitrogen; #L34356) was used to determine LDL uptake in APOE3 and APOE4 iMGLs. Monocultures were treated with 5 µg/ml of pHrodo-LDL and incubated for 1 hour before live cells were imaged with an EVOS cell imaging system (Thermo Scientific). Images were processed in IMARIS (Oxford Instruments) to reconstruct cellular boundaries and quantify intracellular content as mean fluorescence intensity.

RNA Analysis of iMGLs and Spheroids

RNA extraction from biological replicates (n=3) for the isogenic pair (APOE3 and APOE4) of iMGLs exposed to spheroid conditioned media or unspent neuronal media was achieved with RNeasy Plus Mini Kit (Qiagen). RNA integrity number (RIN) scores were determined to be above 9 before library preparation. MIT BioMicro Center prepared libraries using the NEBNext Ultra II RNA Library Prep Kit (New England Biolabs) and performed 75 bases single-end run NextSeq 500 Illumina sequencing. FASTQ reads were aligned using STAR (v.2.6.1a) to GRCh37 reference genome (GENCODE 19) (Dobin et al., 2013). Transcripts were quantified using HTSeq, data was normalized utilizing RUV-seq and differential gene expression analysis was performed through DESeq2 as previously described (Meharena et al., 2022). Significant differentially expressed genes (DEGs) were called with an FDR<0.05 with unrestricted log 2 fold-change cut-offs. Gene ontology analysis was performed using http://bioinformatic.sdstate.edu/go/ and EnrichR Appyter https://maayanlab.cloud/Enrichr/. RNA extraction for qPCR analysis was performed similarly, and reverse transcription performed with RNA to cDNA EcoDry Premix (Takara) according to manufacturer's instruction. Gene expression was analyzed with Real-Time PCR (Bio-Rad, CFX96) and SsoFast EvaGreen Supermix (Bio-Rad). Expression data was normalized to housekeeping gene GAPDH using the $2^{-\Delta\Delta CT}$ relative quantification method.

Plasmids, Cloning and Lentivirus Production

To target KCNJ9 (GIRK3) in CRISPRi iPS-derived neurons, three distinct gene target sequences were picked from the sgRNA/gene published library for CRISPRi (Horlbeck, eLife). Ligated product was transformed into stabl3 competent E. coli (New England Biolabs) and transformed screened for insert via sanger sequencing with U6 forward universal primer (GeneWiz Azenta) and aligned to plasmid (SnaGene software). Clones were then transfected into HEK293 Ts together with lentiviral packaging and envelope vectors to generate lentivirus following the previously published protocol. Lentiviral supernatant was collected 48 hours after transfection and centrifuged for 2 hours by ultracentrifugation at 25,000 RPM at 4° C. (Beckman Coulter). Pellets were resuspended in DPBS and frozen in −80° C. until used. All three sgRNA viruses were mixed equally to deliver a pool totaling 12 ul per well of a 48-well MEA plate. Virus was top loaded and allowed to incubate overnight in neurons that had been seeded within the past 48 hours. Within 5-7 days tRFP (turbo Red Fluorescent Protein) expression was visible, and by 3 weeks the vast majority of cells in the culture expressed high levels of RFP.

REFERENCES

1. Dementia. who.int/news-room/fact-sheets/detail/dementia.
2. Gatz, M. et al. Role of genes and environments for explaining Alzheimer disease. *Arch. Gen. Psychiatry* 63, 168-174 (2006).
3. Kunkle, B. W. et al. Genetic meta-analysis of diagnosed Alzheimer's disease identifies new risk loci and implicates Aβ, tau, immunity and lipid processing. *Nat. Genet.* 51, 414-430 (2019).
4. Lambert, J. C. et al. Meta-analysis of 74,046 individuals identifies 11 new susceptibility loci for Alzheimer's disease. *Nat. Genet.* 45, 1452-1458 (2013).
5. Corder, E. H. et al. Gene dose of apolipoprotein E type 4 allele and the risk of Alzheimer's disease in late onset families. *Science* 261, 921-923 (1993).
6. Strittmatter, W. J. et al. Apolipoprotein E: high-avidity binding to beta-amyloid and increased frequency of type 4 allele in late-onset familial Alzheimer disease. *Proc. Natl. Acad. Sci. U.S.A* 90, 1977-1981 (1993).
7. Bertram, L., McQueen, M. B., Mullin, K., Blacker, D. & Tanzi, R. E. Systematic meta-analyses of Alzheimer disease genetic association studies: the AlzGene database. *Nat. Genet.* 39, 17-23 (2007).
8. Pimenova, A. A., Raj, T. & Goate, A. M. Untangling Genetic Risk for Alzheimer's Disease. *Biological Psychiatry* vol. 83 300-310 (2018).
9. Eisenberg, D. T. A., Kuzawa, C. W. & Geoffrey Hayes, M. Worldwide allele frequencies of the human apolipoprotein E gene: Climate, local adaptations, and evolutionary history. *American Journal of Physical Anthropology* vol. 143 100-111 (2010).
10. van der Flier, W. M. et al. Distribution of APOE Genotypes in a Memory Clinic Cohort. *Dement. Geriatr. Cogn. Disord.* 25, 433-438 (2008).
11. Jessen, F. et al. AD dementia risk in late MCI, in early MCI, and in subjective memory impairment. *Alzheimers. Dement.* 10, 76-83 (2014).
12. Wang, X., Wang, H., Li, H., Li, T. & Yu, X. Frequency of the apolipoprotein E ε4 allele in a memory clinic cohort in Beijing: a naturalistic descriptive study. *PLoS One* 9, e99130 (2014).
13. Cho, H. et al. Distribution and clinical impact of apolipoprotein E4 in subjective memory impairment and early mild cognitive impairment. *Sci. Rep.* 10, 13365 (2020).
14. Crean, S. et al. Apolipoprotein E ε4 Prevalence in Alzheimer's Disease Patients Varies across Global Populations: A Systematic Literature Review and Meta-Analysis. *Dementia and Geriatric Cognitive Disorders* vol. 31 20-30 (2011).
15. Liu, C.-C. et al. ApoE4 Accelerates Early Seeding of Amyloid Pathology. *Neuron* 96, 1024-1032.e3 (2017).
16. Shi, Y. et al. ApoE4 markedly exacerbates tau-mediated neurodegeneration in a mouse model of tauopathy. *Nature* vol. 549 523-527 (2017).
17. Verghese, P. B. et al. ApoE influences amyloid-β (Aβ) clearance despite minimal apoE/Aβ association in physiological conditions. *Proc. Natl. Acad. Sci. U.S.A* 110, E1807-16 (2013).
18. Castellano, J. M. et al. Human apoE isoforms differentially regulate brain amyloid-β peptide clearance. *Sci. Transl. Med.* 3, 89ra57 (2011).
19. Liu, C.-C., Liu, C.-C., Kanekiyo, T., Xu, H. & Bu, G. Apolipoprotein E and Alzheimer disease: risk, mechanisms and therapy. *Nat. Rev. Neurol.* 9, 106-118 (2013).
20. Rauch, J. LRP1 is a master regulator of tau uptake and spread. *The FASEB Journal* vol. 35 (2021).
21. Brecht, W. J. et al. Neuron-specific apolipoprotein e4 proteolysis is associated with increased tau phosphorylation in brains of transgenic mice. *J. Neurosci.* 24, 2527-2534 (2004).
22. Shi, Y. et al. ApoE4 markedly exacerbates tau-mediated neurodegeneration in a mouse model of tauopathy. *Nature* 549, 523-527 (2017).
23. Shi, Y. et al. Microglia drive APOE-dependent neurodegeneration in a tauopathy mouse model. *Journal of Experimental Medicine* vol. 216 2546-2561 (2019).
24. Hatters, D. M., Peters-Libeu, C. A. & Weisgraber, K. H. Apolipoprotein E structure: insights into function. *Trends Biochem. Sci.* 31, 445-454 (2006).
25. ALZHEIMER & A. Uber eine eigenartige Erkrankung der Hirnrinde. *Zentralbl. Nervenh. Psych.* 18, 177-179 (1907).
26. Sienski, G. et al. disrupts intracellular lipid homeostasis in human iPSC-derived glia. *Sci. Transl. Med.* 13, (2021).
27. Jeong, W., Lee, H., Cho, S. & Seo, J. ApoE4-Induced Cholesterol Dysregulation and Its Brain Cell Type-Specific Implications in the Pathogenesis of Alzheimer's Disease. *Mol. Cells* 42, 739-746 (2019).
28. Mathys, H. et al. Temporal Tracking of Microglia Activation in Neurodegeneration at Single-Cell Resolution. *Cell Reports* vol. 21 366-380 (2017).
29. Mathys, H. et al. Single-cell transcriptomic analysis of Alzheimer's disease. *Nature* 570, 332-337 (2019).
30. Keren-Shaul, H. et al. A Unique Microglia Type Associated with Restricting Development of Alzheimer's Disease. *Cell* 169, 1276-1290.e17 (2017).
31. Xu, Q. et al. Profile and regulation of apolipoprotein E (ApoE) expression in the CNS in mice with targeting of green fluorescent protein gene to the ApoE locus. *J. Neurosci.* 26, 4985-4994 (2006).
32. Mahley, R., Huang, Y. & Weisgraber, K. Detrimental Effects of Apolipoprotein E4: Potential Therapeutic Targets in Alzheimers Disease. *Current Alzheimer Research* vol. 4 537-540 (2007).
33. Lin, Y.-T. et al. APOE4 Causes Widespread Molecular and Cellular Alterations Associated with Alzheimer's Disease Phenotypes in Human iPSC-Derived Brain Cell Types. *Neuron* 98, 1141-1154.e7 (2018).
34. Bennett, D. A. et al. Religious Orders Study and Rush Memory and Aging Project. *Journal of Alzheimer's Disease* vol. 64 S161-S189 (2018).
35. Wang, D. et al. Comprehensive functional genomic resource and integrative model for the human brain. *Science* 362, (2018).
36. Franzen, O., Gan, L.-M. & Björkegren, J. L. M. PanglaoDB: a web server for exploration of mouse and human single-cell RNA sequencing data. *Database* 2019, (2019).
37. Kanekiyo, T., Xu, H. & Bu, G. ApoE and Aβ in Alzheimer's Disease: Accidental Encounters or Partners? *Neuron* vol. 81 740-754 (2014).
38. Yin, C. et al. ApoE attenuates unresolvable inflammation by complex formation with activated C1q. *Nat. Med.* 25, 496-506 (2019).
39. Roses, A. D., Weisgraber, K. H. & Christen, Y. *Apolipoprotein E and Alzheimer's Disease*. (Springer Science & Business Media, 2012).
40. Huang, Y.-W. A., Zhou, B., Wernig, M. & Südhof, T. C. ApoE2, ApoE3, and ApoE4 Differentially Stimulate APP Transcription and Aβ Secretion. *Cell* vol. 168 427-441.e21 (2017).

41. Moll, T., Shaw, P. J. & Cooper-Knock, J. Disrupted glycosylation of lipids and proteins is a cause of neurodegeneration. *Brain* 143, 1332-1340 (2020).
42. Ye, S. et al. Apolipoprotein (apo) E4 enhances amyloid β peptide production in cultured neuronal cells: ApoE structure as a potential therapeutic target. *Proc. Natl. Acad. Sci. U.S.A.* 102, 18700-18705 (2005).
43. Tachibana, M. et al. APOE4-mediated amyloid-β pathology depends on its neuronal receptor LRP1. *J. Clin. Invest.* 129, 1272-1277 (2019).
44. Shanbhag, N. M. et al. Early neuronal accumulation of DNA double strand breaks in Alzheimer's disease. *Acta Neuropathol Commun* 7, 77 (2019).
45. Mattsson, N. et al. Increased amyloidogenic APP processing in APOE ε4-negative individuals with cerebral β-amyloidosis. *Nat. Commun.* 7, 10918 (2016).
46. Zalocusky, K. A. et al. Neuronal ApoE upregulates MHC-I expression to drive selective neurodegeneration in Alzheimer's disease. *Nature Neuroscience* vol. 24 786-798 (2021).
47. Qi, G. et al. ApoE4 Impairs Neuron-Astrocyte Coupling of Fatty Acid Metabolism. *Cell Rep.* 34, 108572 (2021).
48. Douvaras, P. & Fossati, V. Generation and isolation of oligodendrocyte progenitor cells from human pluripotent stem cells. *Nat. Protoc.* 10, 1143-1154 (2015).
49. Douvaras, P. et al. Efficient generation of myelinating oligodendrocytes from primary progressive multiple sclerosis patients by induced pluripotent stem cells. *Stem Cell Reports* 3, 250-259 (2014).
50. Olzmann, J. A. & Carvalho, P. Dynamics and functions of lipid droplets. *Nat. Rev. Mol. Cell Biol.* 20, 137-155 (2019).
51. Lund, E. G., Guileyardo, J. M. & Russell, D. W. cDNA cloning of cholesterol 24-hydroxylase, a mediator of cholesterol homeostasis in the brain. *Proc. Natl. Acad. Sci. U.S.A.* 96, 7238-7243 (1999).
52. He, Y. et al. Identification of a Lysosomal Pathway That Modulates Glucocorticoid Signaling and the Inflammatory Response. *Science Signaling* vol. 4 ra44-ra44 (2011).
53. Plemel, J. R. et al. Mechanisms of lysophosphatidylcholine-induced demyelination: A primary lipid disrupting myelinopathy. *Glia* vol. 66 327-347 (2018).
54. Law, S.-H. et al. An Updated Review of Lysophosphatidylcholine Metabolism in Human Diseases. *Int. J. Mol. Sci.* 20, (2019).
55. Saher, G., Quintes, S. & Nave, K.-A. Cholesterol: a novel regulatory role in myelin formation. *Neuroscientist* 17, 79-93 (2011).
56. Ottinger, E. et al. Collaborative Development of 2-Hydroxypropyl-β-Cyclodextrin for the Treatment of Niemann-Pick Type C1 Disease. *Current Topics in Medicinal Chemistry* vol. 14 330-339 (2014).
57. Leger, M. et al. Object recognition test in mice. *Nat. Protoc.* 8, 2531-2537 (2013).
58. Brun, A. & Englund, E. A white matter disorder in dementia of the Alzheimer type: A pathoanatomical study. *Annals of Neurology* vol. 19 253-262 (1986).
59. Bartzokis, G. Age-related myelin breakdown: a developmental model of cognitive decline and Alzheimer's disease. *Neurobiol. Aging* 25, 5-18; author reply 49-62 (2004).
60. Behrendt, G. et al. Dynamic changes in myelin aberrations and oligodendrocyte generation in chronic amyloidosis in mice and men. *Glia* vol. 61 273-286 (2013).
61. Dean, D. C., 3rd et al. Association of Amyloid Pathology With Myelin Alteration in Preclinical Alzheimer Disease. *JAMA Neurol.* 74, 41-49 (2017).
62. Gold, B. T., Powell, D. K., Andersen, A. H. & Smith, C. D. Alterations in multiple measures of white matter integrity in normal women at high risk for Alzheimer's disease. *Neuroimage* 52, 1487-1494 (2010).
63. Leng, K. et al. Molecular characterization of selectively vulnerable neurons in Alzheimer's Disease. doi:10.1101/2020.04.04.025825.
64. Jäkel, S. et al. Altered human oligodendrocyte heterogeneity in multiple sclerosis. *Nature* vol. 566 543-547 (2019).
65. Remer, J. et al. Longitudinal white matter and cognitive development in pediatric carriers of the apolipoprotein ε4 allele. *Neuroimage* 222, 117243 (2020).
66. Dean, D. C., 3rd et al. Brain differences in infants at differential genetic risk for late-onset Alzheimer disease: a cross-sectional imaging study. *JAMA Neurol.* 71, 11-22 (2014).
67. Vanzulli, I. et al. Disruption of oligodendrocyte progenitor cells is an early sign of pathology in the triple transgenic mouse model of Alzheimer's disease. *Neurobiol. Aging* 94, 130-139 (2020).
68. Zhang, P. et al. Senolytic therapy alleviates Aβ-associated oligodendrocyte progenitor cell senescence and cognitive deficits in an Alzheimer's disease model. *Nature Neuroscience* vol. 22 719-728 (2019).
69. Gibson, E. M. et al. Neuronal activity promotes oligodendrogenesis and adaptive myelination in the mammalian brain. *Science* 344, 1252304 (2014).
70. Xin, W. & Chan, J. R. Myelin plasticity: sculpting circuits in learning and memory. *Nat. Rev. Neurosci.* 21, 682-694 (2020).
71. Wang, F. et al. Myelin degeneration and diminished myelin renewal contribute to age-related deficits in memory. *Nat. Neurosci.* 23, 481-486 (2020).
72. Yankner, B. A., Lu, T. & Loerch, P. The aging brain. *Annu. Rev. Pathol.* 3, 41-66 (2008).
73. Feringa, F. M. & van der Kant, R. Cholesterol and Alzheimer's Disease; From Risk Genes to Pathological Effects. *Frontiers in Aging Neuroscience* vol. 13 (2021).
74. Kant, R. van der et al. Cholesterol Metabolism Is a Druggable Axis that Independently Regulates Tau and Amyloid-β in iPSC-Derived Alzheimer's Disease Neurons. *Cell Stem Cell* vol. 24 363-375.e9 (2019).
75. Chu, C.-S. et al. Use of statins and the risk of dementia and mild cognitive impairment: A systematic review and meta-analysis. *Sci. Rep.* 8, 5804 (2018).
76. Schultz, B. G., Patten, D. K. & Berlau, D. J. The role of statins in both cognitive impairment and protection against dementia: a tale of two mechanisms. *Transl. Neurodegener.* 7, 5 (2018).
77. Bennett, D. A. et al. Neuropathology of older persons without cognitive impairment from two community-based studies. *Neurology* 66, 1837-1844 (2006).
78. Traag, V. A., Waltman, L. & van Eck, N. J. From Louvain to Leiden: guaranteeing well-connected communities. *Sci. Rep.* 9, 5233 (2019).
79. Hänzelmann, S., Castelo, R. & Guinney, J. GSVA: gene set variation analysis for microarray and RNA-Seq data. *BMC Bioinformatics* vol. 14 7 (2013).
80. He, L. et al. NEBULA is a fast negative binomial mixed model for differential or co-expression analysis of large-scale multi-subject single-cell data. *Communications Biology* vol. 4 (2021).
81. Kamphorst, J. J., Fan, J., Lu, W., White, E. & Rabinowitz, J. D. Liquid Chromatography—High Resolution Mass Spectrometry Analysis of Fatty Acid Metabolism. *Analytical Chemistry* vol. 83 9114-9122 (2011).

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method of reversing an APOE4-associated cholesterol phenotype in a subject comprising administering to the subject a cyclodextrin or pharmaceutically acceptable salt thereof in an effective amount to inhibit amyloid synthesis in the subject, wherein the subject is identified as being APOE4 positive.

2. The method of claim 1, wherein the APOE4-associated cholesterol phenotype is myelination degeneration.

3. The method of claim 1, wherein the subject has Alzheimer's Disease and the subject is administered an effective amount of the cyclodextrin to treat Alzheimer's disease.

4. The method of claim 3, wherein the Alzheimer's disease is mild to moderate Alzheimer's disease.

5. The method of claim 3, wherein the Alzheimer's disease is moderate to severe Alzheimer's disease.

6. The method of claim 1, wherein the subject has CAA.

7. The method of claim 1, wherein the subject has been diagnosed with Alzheimer's disease.

8. The method of claim 1, wherein the subject is administered a dose of between 1 and 50 mg cyclodextrin, and the dose is administered once daily.

9. The method of claim 1, wherein the cyclodextrin is administered as an immediate release formulation.

10. The method of claim 1, wherein the cyclodextrin is administered as an sustained release formulation.

11. The method of claim 1, further comprising administering another therapeutic agent.

12. The method of claim 1, wherein the subject has defect in learning and memory.

13. The method of claim 1, wherein the cyclodextrin is selected from a sulfonated cyclodextrin, an alpha-cyclodextrin, a beta-cyclodextrin, a gamma cyclodextrin, a methyl-beta-cyclodextrin, a hydroxypropyl beta-cyclodextrin, and a sulfobutylether beta-cyclodextrin.

14. A method of reversing hypomyelination pathologies associated with Alzheimer's Disease in a subject, comprising administering to the subject cyclodextrin, wherein the subject is identified as being APOE4 positive.

15. The method of claim 14, wherein the cyclodextrin is selected from a sulfonated cyclodextrin, an alpha-cyclodextrin, a beta-cyclodextrin, a gamma cyclodextrin, a methylbeta-cyclodextrin, a hydroxypropyl beta-cyclodextrin, and a sulfobutylether beta-cyclodextrin.

* * * * *